(12) United States Patent
Shinkai et al.

(10) Patent No.: US 6,410,561 B1
(45) Date of Patent: Jun. 25, 2002

(54) AMIDE DERIVATIVES AND NOCICEPTIN ANTAGONISTS

(75) Inventors: Hisashi Shinkai; Takao Ito; Hideki Yamada, all of Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 09/646,781

(22) PCT Filed: Mar. 23, 1999

(86) PCT No.: PCT/JP99/01462

§ 371 (c)(1),
(2), (4) Date: Sep. 22, 2000

(87) PCT Pub. No.: WO99/48492

PCT Pub. Date: Sep. 30, 1999

(30) Foreign Application Priority Data

Mar. 26, 1998 (JP) .......................................... 10-100029

(51) Int. Cl.⁷ ..................... A61K 31/47; C07D 215/38; C07D 215/16
(52) U.S. Cl. ...................... 514/313; 514/314; 546/159; 546/162; 546/178; 546/171
(58) Field of Search ................................ 514/313, 314; 546/162, 159, 178, 171

(56) References Cited

U.S. PATENT DOCUMENTS

| | | | |
|---|---|---|---|
| 4,293,549 A | 10/1981 | Rachlin et al. | 424/245 |
| 4,753,951 A | 6/1988 | Takada et al. | 514/293 |
| 4,839,366 A | 6/1989 | Quadro | 514/312 |
| 5,019,574 A | 5/1991 | Miura et al. | 514/235.2 |
| 5,104,884 A | 4/1992 | Kóródi et al. | 514/312 |

FOREIGN PATENT DOCUMENTS

| | | |
|---|---|---|
| EP | 0 277 794 | 2/1988 |
| EP | 0 381 422 | 1/1990 |
| EP | 0381422 | * 1/1990 |
| EP | 07252228 | * 1/1990 |
| JP | 54-73784 | 6/1979 |
| JP | 59-210084 | 11/1984 |
| JP | 62-503030 | 12/1987 |
| JP | 63-99069 | 4/1988 |
| JP | 2-167265 | 6/1990 |
| JP | 3 223278 A | 10/1991 |
| JP | 3-223278 | 10/1991 |
| JP | 7 252228 A | 10/1995 |
| JP | 7-252228 | 10/1995 |
| JP | 63-264460 | 11/1998 |
| WO | WO 96/11930 | 4/1996 |
| WO | WO 96/13485 | 5/1996 |
| WO | WO 97/14681 | 4/1997 |

OTHER PUBLICATIONS

Aries Robert, "Analgesic 3–methylsalicyloylanthranilates," Brevet D'invention, (Feb. 21, 1969; 3 pp.,) 1.557.928 (with abstract).

Aries Robert, Salicylamidoquinoline Analgesics, "Brevet D'invention", (Oct. 25, 1968; 3pp.) 1.543.405 (with abstract).

Dr. Heinrich Jensch, "Guanylhydrazones of the 4–Aminoquinoline series", 10– Organic Chemistry Ger. No. 831.100; 3pp.) (Feb. 11, 1952).

Dr. Heinrich Jensch, 4–Aminoquinaldine compound 10G–Heterocyclic compound and Chemical Abstract Ger. No. 947.552, Sep. 6, 1956; Cl 12p.).

Chu–Tzu Pen and T.C. Daniels "The Synthesis of Some 6–N Substituted Amido Derivatives of 4,6–Diaminoquinaldine and a Study of their in vitro Antibacterial Activity 1.2"; (Report No. PB–981 Jul. 1945), p. 17.

* cited by examiner

*Primary Examiner*—Alan L. Rotman
*Assistant Examiner*—Binta Robinson
(74) *Attorney, Agent, or Firm*—Foley & Lardner

(57) ABSTRACT

The present invention relates to a compound of the formula [1']

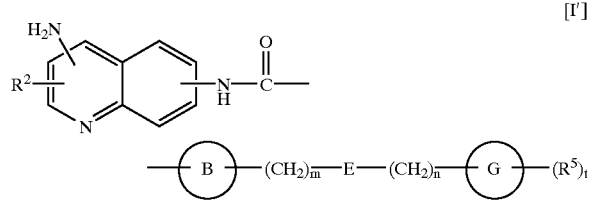

wherein $R^2$ is lower alkyl optionally substituted by hydroxy, amino and the like, ring B is phenyl, thienyl and the like, E is a single bond, —O—, —S— and the like, ring G is aryl, heterocyclic group and the like, $R^5$ is halogen atom, hydroxy, lower alkyl optionally substituted by halogen atom etc., and the like, t is 0 or an integer of 1 to 5, when t is an integer of 2 to 5, each $R^5$ may be the same or different, m is 0 or an integer of 1 to 8, and n is 0 or an integer of 1 to 4, and a nociceptin antagonist containing compound [1'] as an active ingredient. The compound [1'] shows, due to nociceptin antagonistic action, analgesic effect against sharp pain such as postoperative pain and the like. The present invention also relates to the use of certain amide derivative inclusive of compound [1'] as a nociceptin antagonist or analgesic.

12 Claims, No Drawings

AMIDE DERIVATIVES AND NOCICEPTIN ANTAGONISTS

TECHNICAL FIELD

The present invention relates to a nociceptin antagonist containing a novel amide derivative or a pharmaceutically acceptable salt thereof. More particularly, the present invention relates to an analgesic containing, as an active ingredient, a novel amide derivative or a pharmaceutically acceptable salt thereof, which show analgesic effect as nociceptin antagonist by selectively acting on an opioid receptor like-1 receptor and which are useful for the treatment of pain, particularly sharp pain or pain caused by sensory nerve abnormality, such as hyperalgesia and allodynia. The present invention moreover relates to a novel use of a certain kind of amide derivative as a nociceptin antagonist and analgesic.

BACKGROUND ART

Pain is a sensation felt by anybody and is an important vital signal or alarm signal.

Pain caused by injury, surgery, inflammation and the like, as well as chronic pain stemming from injury, dysfunction and the like of nerves after recovery from an injury is one of the major clinical problems. Chronic pain sometimes causes autonomic disorder, dyskinesia or mental disorder, wherein the pain itself is the cause of a different disease.

There is also known to exist pain due to sensory nerve abnormality, such as hyperalgesia associated with promotion of reaction in response to an ordinary pain stimulus, allodynia wherein pain is felt in response to a stimulus that normally causes no pain, and the like.

Analgesics are divided into central analgesic and peripheral analgesic according to the main action site thereof. Inasmuch as the cause of pain is a complicated entanglement of autonomic nerve reactions, feeling and the like, sedative, antianxiety, antidepressant, hypnotic, antispasmodic, vasodilator and the like are used as analgesic auxiliary agents.

Central analgesics are roughly divided into narcotic analgesic, anarcotic analgesic and antipyretic analgesic.

Narcotic and anarcotic opioids have been used for the treatment of sharp pain such as postoperative pain and myocardial infarction, burn and the like. These analgesics show noticeable effects resulting from a strong analgesic action combined with an action to remove fear of pain. On the other hand, narcotic analgesics accompany physical dependence and mental dependence and express withdrawal syndrome by drug dependence. Other side effects of respiratory suppresion, nausea, emesis, constipation, dysuria and the like restrict their use.

Antipyretic analgesic is effective for superficial pain, such as toothache, myalgia and the like, but is considered to be ineffective for visceralgia. Its antipyretic action is considered to focus on hypothalamus thermoregulation center, and analgesic action is mainly exerted via peripheral nerves. However, there are many unknown parts in the central action mechanism thereof. Its analgesic effect is generally weaker than that offered by narcotic and anarcotic opioids. Consequently, sharp pain is cautiously treated with narcotic and anarcotic opioids in clinical situations to the extent that causes less side effects.

Although more than 20 years have passed since the analgesic effect of morphine by intrathecal administration to human was confirmed and morphine was first applied to clinical situations, a pharmaceutical agent exceeding morphine in terms of various side effects, histotoxicity to spinal cord and the like, that accompany analgesic effect of morphine, has not been found.

Certain pain caused by injury and functional disorder of nerves and the like is resistant to analgesics currently in clinical use, such as antipyretic analgesic and narcotic analgesic, and shows no significant analgesic effect.

Thus, there reaims a demand for a safe and effective analgesic, particularly a strong analgesic free from addiction and an analgesic to treat pain caused by sensory nerve abnormality such as hyperalgesia, allodynia and the like.

Pain is caused when an algesic substance, which is released upon occurrence of tissue disorder due to nociceptive stimulus (chemical stimulus, mechanical stimulus, thermal stimulus), excites nociceptor (free nerve terminal) at the sensory nerve terminal, and the information of the pain sensation reaches the cerebral cortex and is recognized as pain. In addition, visceralgia is considered to be caused by the contraction of visceral smooth muscle, that mechanically extends and excites the sensory nerve.

Pain sensation is mostly transmitted by two kinds of thin nerve fiber $A\delta$ and C fibers, wherein sharp mechanical stimulus conducts myelinated $A\delta$ fiber and dull pain conducts unmyelinated C fiber. Typical algesic substance includes bradykinin, serotonin, histamine and the like, that act on nociceptor at the nerve terminal. There is a substance that encourages action of an algesic substance, like prostaglandin synthesized at the inflammation site in the peripheral tissue. Such pain afferent fiber (primary afferent fiber) forms synapse on the surface layer of dorsicornu. The primary afferent fiber excites nociceptive neuron via neurotransmitters, such as excitatory amino acid, substance P and the like, and the information is transmitted from dorsicornu to medulla oblongata, thalamus and to cerebral cortex.

Pressure and tactile sensation is mainly transmitted by thicker $A\beta$ fiber which transmits the information from sensory nerve terminal to dorsicornu, medulla oblongata, thalamus and to cerebral cortex, like pain afferent fiber.

Opioid receptors involved in algesia exist in various parts of these spinothalamic tracts. The respiratory suppressive action, nauseant action and the like result from the action on the opioid receptor in the medulla oblongata. While opioid acts on spinal cord, medulla oblongata, thalamus and cerebral cortex to show strong analgesic effect, suppression of thalamus and cerebral cortex is not its main action. Direct suppression of opioid receptor in the dorsicornu neuron and suppression of dorsicornu neuron by descending depression via midbrain and medulla oblongata are considered to be the main action.

Tactile sensation tends to be dull upon sustained application of stimuli of the same intensity. This adaptation is unfeasible in case of pain, but sustained release of neurotransmitter by long-term stimulation of sensory nerve is considered to induce chronic pain by changing the excitatory or information transmission efficiency of the nerve cell. In addition, inhibitory neurotransmitters, such as $\gamma$-aminobutyric acid (GABA), glycine and the like, suppress excitement of nerves upon activation of each receptor. While allodynia is considered to be partly induced by dull suppression of neurotransmission due to the stimuli repeatedly applied to the sensory nerve, the mechanism of the onset of chronic pain, hyperalgesia and allodynia has been known only to a limited degree.

As described, the sensory nerve transmission is controlled by excitatory nerve fiber and inhibitory nerve fiber in complicated relationship with each other, and many neurotransmitters involved therein have been found to exist. Hence, there are many targets used to find a pharmaceutical agent exhibiting effective analgesic action.

Following the discovery of cerebral morphine receptor in 1973, enkephalin, which is an endogenous pentapeptide having analgesic effect, was first found and isolated in 1975. There are known more than 20 kinds of morphinomimetic peptides under the category of opioid peptide, that inhibit the transmission of algesia information.

These opioids inclusive of morphine act on opioid receptor. The opioid receptor is known to include several subtypes, wherein morphine shows high affinity for $\mu$ receptor, enkephalin shows high affinity for $\delta$ receptor and dynorphin shows high affinity for $\kappa$ receptor, these consisting the base thereof.

It is a long-known fact that involvement of $\mu$ receptor from among these is important for the analgesic effect and the mechanism thereof has been most elucidated. The study of withdrawal syndrome induction capability and the like of each subtype by the use of opioid antagonist has revealed that the morphine addiction is mainly attributable to the action via $\mu$ receptor.

An opioid receptor like-1 (ORL-1) receptor has high homology with opioid receptor but does not bind with conventional opioid ligands. This receptor was cloned in 1993.*1*2 In 1995, peptide consisting of 17 amino acids was isolated as endogenous ligand of ORL-1 receptor, and structurally characterized and named Nociceptin or Orphanin FQ *3*4 (*1; FEBS Lett., 341, 33–38, 1994) (*2; FEBS Lett., 347, 284–288, 1994) (*3; Nature, 377, 532–535, 1995) (*4; Science, 270, 792–794, 1995).

The amino acid sequence of nociceptin is similar to that of Dynorphin A which is an endogenous opioid peptide. Dynorphin A is a $\kappa$ receptor agonist showing analgesic effect, but binds weakly with ORL-1 receptor and is said to have no activity*5. Nociceptin binds extremely weakly with an opioid receptor*6, and algesia tests including hot plate test*7 using mouse, scratching of lower abdomen with both hindlimbs of mouse, biting and licking of both hindlimbs (SBL) behavior induction test*8 and the like have revealed its promoting action on transmission of pain information. These reports taught that nociceptin and ORL-1 receptor had specific affinity for each other, and nociceptin was a peptide that induced or amplified pain, conversely from the case of opioid peptide. The study of action mechanism thereof is underway. (*5; Eur. J. Pharmacol., 321, 97, 1997) (*6; J. Biol. Chem., 271, 23642, 1996) (*7; Anesthesia, 45, 1060–1066,1996) (*8; 18$^{th}$ Analgesic.Opioid Peptide Symposium Abstract, 11–14, 1997).

ORL-1 receptor has been reported to express more in the central nerve system, such as cerebral cortex, hypothalamus, spinal cord and the like*9, and nociceptin has been shown to be distributed more on the surface layer of dorsicornu where primary pain afferent fiber terminates*10, and algesia transmission of nociceptin is considered to be mainly through central nerve system (*9; J. Neurochemistry, 64, 34–40, 1995) (*10; Neuro Report 7, 3021–3025, 1996).

It has been also reported that administration of nociceptin induces nociceptive hypersensitivity (hyperalgesia*3*4, allodynia*11) and that it amplifies excitatory stimulus by heat and tactile (*11; Molecular Brain Research, 43, 96–104, 1996).

Under the circumstances, substances reported to exhibit a nociceptin antagonistic action are only nociceptin-like polypeptide and naloxone benzoylhydrazone which is a $\kappa$ receptor antagonist having a morphine-like structure, both of which having ORL-1 receptor affinity, and a pharmaceutical agent having specific antagonistic action on ORL-1 receptor has not been developed.

Known analgesic having a quinoline skeleton includes opioid or anesthetic antagonist analgesic [Japanese Patent Unexamined Publication No. 63-264460 (EP 277794; BOC Inc.)], analgesic having a different action mechanism [Japanese Patent Unexamined Publication No. 62-503030 (U.S. Pat. No. 5,104,884; Alkaloida Vegyeszeti Gyar, antifungal action), WO96/13485 (EP 807105; Fujisawa Pharmaceutical Industries, Ltd., bradykinin antagonist), WO96/11930 (Smithkline beecham P.L.C., serotonin receptor antagonist), Japanese Patent Unexamined Publication No. 59-210084 (U.S. Pat. No. 4,839,366; Chiesi Farmaceutici S.p.A., prostaglandin synthesis inhibition), Japanese Patent Unexamined Publication No. 54-73784 (U.S. Pat. No. 4,293,549; Leo Pharmaceutical Products Limited A/S), FR 1557928 and FR 1543405 (M. Robert ARIES) and the like. These do not include a compound having the structure of the inventive compound, nor do they disclose an action on nociceptin or ORL-1 receptor as in the present invention.

Compounds having a quinoline skeleton structurally similar to that in the inventive compound and which can be used for effects other than analgesic effect are shown in DE 831100 and DE 947552 (anti-blood parasite agent), WO97/14681 (therapeutic agent of bone metabolism abnormality), Japanese Patent Unexamined Publication No. 63-99069 (U.S. Pat. No. 4,753,951; antipsychotic agent), Japanese Patent Unexamined Publication No. 2-167265 (U.S. Pat. No. 5,019,574; psychoneurotic function improving agent), Journal of American Chemistry Society (76, 3703–3708, 1956) (antibacterial agent), HU34479 {disclosure of quinoline skeleton as a synthetic intermediate for imidazo[4,5-c] quinoline derivative (analgesic)} and the like, though none of which discloses effectiveness as an analgesic.

DISCLOSURE OF THE INVENTION

Based on the foregoing findings, a pharmaceutical agent having nociceptin antagonistic action can make an effective agent for pain, particularly sharp pain such as postsurgery pain and the like or pain caused by sensory nerve abnormality, such as hyperalgesia, allodynia and the like, and a safe pharmaceutical agent showing selective action on ORL-1 receptor and free of marked side effects.

It is therefore an object of the present invention to provide a pharmaceutical agent having an action mechanism different from that of known analgesics, via nociceptin antagonistic action.

It is also an object of the present invention to provide a novel compound having a nociceptin antagonistic action, which is useful as an analgesic.

As a result of the intensive study of the present inventors in an attemp to solve the above-mentioned problems, the present invention now provides a novel compound having an analgesic effect.

The present invention specifically provides the following (1) to (20).

(1) A nociceptin antagonist containing an amide derivative of the formula [1]

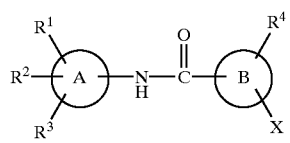

wherein
- $R^1$ and $R^2$ are the same or different and each is hydrogen atom, lower alkyl optionally substituted by hydroxy, amino, lower alkylamino or di(lower)alkylamino;
- $R^3$ and $R^4$ are the same or different and each is hydrogen atom, halogen atom or lower alkyl;
- ring A is aryl or heterocyclic group;
- ring B is phenyl, thienyl, furyl, pyrrolyl, pyrrolidinyl, oxazolyl or cyclohexenyl; and
- X is hydrogen atom, halogen atom, lower alkyl optionally substituted by lower alkoxy, lower alkenyl, amino, cyano or a group of the formula

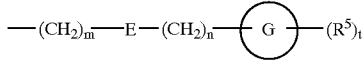

wherein
- E is a single bond, carbonyl, sulfinyl, —O—, —S—, —NHCO—, —CH=CR$^6$— wherein $R^6$ is hydrogen atom or aryl or —NR$^7$— wherein $R^7$ is hydrogen atom, lower alkyl or lower alkoxycarbonyl;
- ring G is aryl, heterocyclic group, cycloalkyl or condensed aryl;
- $R^5$ is halogen atom, hydroxy, lower alkyl optionally substituted by any of halogen atom, hydroxy, lower alkanoyloxy and lower alkoxy optionally substituted by lower alkoxy, lower alkoxy optionally substituted by lower alkoxy, amino, lower alkylamino, di(lower)alkylamino, nitro, cyano, lower alkanoyl, lower alkanoyloxy, carboxy, lower alkoxycarbonyl, lower alkylsulfonyl or phenyl;
- t is 0 or an integer of 1 to 5, which indicates the number of substituents on the ring G, wherein when t is an integer of 2 to 5, each $R^5$ may be the same or different;
- m is 0 or an integer of 1 to 8; and
- n is 0 or an integer of 1 to 4, or a pharmaceutically acceptable salt thereof as an active ingredient.

(2) A nociceptin antagonist containing the amide derivative of (1) above wherein the ring A is quinolyl or a pharmaceutically acceptable salt thereof as an active ingredient.

(3) A nociceptin antagonist containing the amide derivative of (1) above wherein the ring B is phenyl and X is a group of the formula

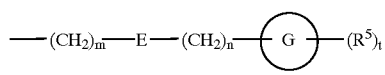

wherein E, ring G, $R^5$, t, m and n are as defined in (1), or a pharmaceutically acceptable salt thereof as an active ingredient.

(4) A nociceptin antagonist containing the amide derivative of (3) above wherein the ring A is

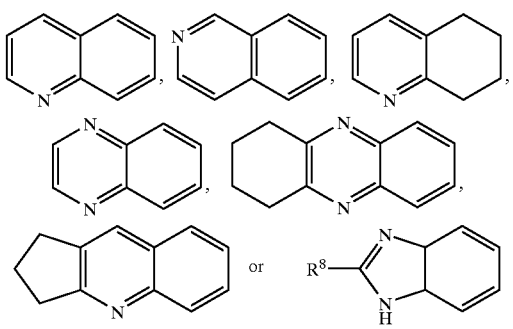

wherein $R^8$ is lower alkylthio, or a pharmaceutically acceptable salt thereof as an active ingredient.

(5) An amide derivative of the formula [1']

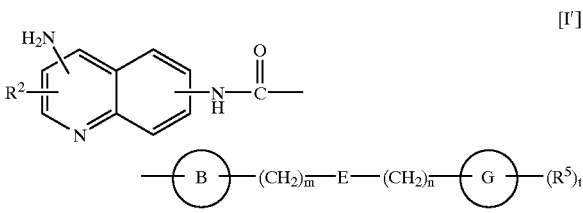

wherein $R^2$, ring B, E, ring G, $R^5$, t, m and n as defined in (1), or a pharmaceutically acceptable salt thereof.

(6) The amide derivative of (5) above, wherein the ring B is phenyl and $R^2$ is lower alkyl, or a pharmaceutically acceptable salt thereof.

(7) The amide derivative of (6) above, wherein the amino substitutes at the 4-position on a quinoline skeleton, $R^2$ is methyl substituting at the 2-position on the quinoline skeleton, E is —O— and the ring B of phenyl has a substituent of the formula

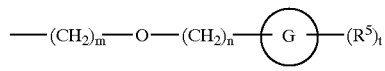

wherein ring G, $R^5$, t, m and n as defined in (1), at the 2-position, or a pharmaceutically acceptable salt thereof.

(8) The amide derivative of (7) above or a pharmaceutically acceptable salt thereof, which is selected from the group consisting of N-(4-amino-2-methyl-6-quinolyl)-2-[(4-ethylphenoxy)methyl]benzamide hydrochloride,
N-(4-amino-2-methyl-6-quinolyl)-2-[(2,4-dichlorophenoxy)methyl]benzamide hydrochloride,
N-(4-amino-2-methyl-6-quinolyl)-2-(phenoxymethyl)benzamide hydrochloride,
N-(4-amino-2-methyl-6-quinolyl)-2-[(4-methoxyphenoxy)methyl]benzamide hydrochloride,
N-(4-amino-2-methyl-6-quinolyl)-2-[(3,5-dimethylphenoxy)methyl]benzamide hydrochloride,
N-(4-amino-2-methyl-6-quinolyl)-2-[(3,4-dimethoxyphenoxy)methyl]benzamide hydrochloride,
N-(4-amino-2-methyl-6-quinolyl)-2-[(4-nitrophenoxy)methyl]benzamide,
N-(4-amino-2-methyl-6-quinolyl)-2-[(2,3-dimethoxyphenoxy)methyl]benzamide hydrochloride,
N-(4-amino-2-methyl-6-quinolyl)-2-[(3-methylphenoxy)methyl]benzamide,
N-(4-amino-2-methyl-6-quinolyl)-2-[(3,5-dimethoxyphenoxy)methyl]benzamide hydrochloride, N-(4-amino-2-methyl-6-quinolyl)-2-[(4-chlorophenoxy)methyl]benzamide hydrochloride,
N-(4-amino-2-methyl-6-quinolyl)-2-[(4-acetylphenoxy)methyl]benzamide hydrochloride,
N-(4-amino-2-methyl-6-quinolyl)-2-[(4-hydroxyphenoxy)methyl]benzamide hydrochloride,
N-(4-amino-2-methyl-6-quinolyl)-2-[(4-methoxymethoxyphenoxy)methyl]benzamide hydrochloride,
N-(4-amino-2-methyl-6-quinolyl)-2-[(3-methoxyphenoxy)methyl]benzamide hydrochloride,
N-(4-amino-2-methyl-6-quinolyl)-2-[(4-cyanophenoxy)methyl]benzamide hydrochloride,
N-(4-amino-2-methyl-6-quinolyl)-2-[(4-methylphenoxy)methyl]benzamide hydrochloride,
N-(4-amino-2-methyl-6-quinolyl)-2-[(4-trifluoromethylphenoxy)methyl]benzamide hydrochloride,
N-(4-amino-2-methyl-6-quinolyl)-2-[(3-nitrophenoxy)methyl]benzamide hydrochloride,
N-(4-amino-2-methyl-6-quinolyl)-2-[(2-nitrophenoxy)methyl]benzamide hydrochloride,
N-(4-amino-2-methyl-6-quinolyl)-2-[(4-acetoxyphenoxy)methyl]benzamide hydrochloride,
N-(4-amino-2-methyl-6-quinolyl)-2-[(2-methoxyphenoxy)methyl]benzamide hydrochloride,
N-(4-amino-2-methyl-6-quinolyl)-2-[(4-aminophenoxy)methyl]benzamide dihydrochloride,
N-(4-amino-2-methyl-6-quinolyl)-2-[(3-chlorophenoxy)methyl]benzamide hydrochloride,
N-(4-amino-2-methyl-6-quinolyl)-2-[(4-fluorophenoxy)methyl]benzamide hydrochloride,
N-(4-amino-2-methyl-6-quinolyl)-2-[(3,4-dichlorophenoxy)methyl]benzamide hydrochloride,
N-(4-amino-2-methyl-6-quinolyl)-2-[(2-chlorophenoxy)methyl]benzamide hydrochloride,
N-(4-amino-2-methyl-6-quinolyl)-2-[(4-dimethylaminophenoxy)methyl]benzamide dihydrochloride,
N-(4-amino-2-methyl-6-quinolyl)-2-[(4-tert-butylphenoxy)methyl]benzamide hydrochloride,
N-(4-amino-2-methyl-6-quinolyl)-2-(4-biphenylyloxymethyl)benzamide hydrochloride,
N-(4-amino-2-methyl-6-quinolyl)-2-[(4-isopropylphenoxy)methyl]benzamide hydrochloride,
N-(4-amino-2-methyl-6-quinolyl)-2-[(4-nitrophenoxy)methyl]benzamide hydrochloride,
N-(4-amino-2-methyl-6-quinolyl)-2-[(4-bromophenoxy)methyl]benzamide hydrochloride,
N-(4-amino-2-methyl-6-quinolyl)-2-[(4-propylphenoxy)methyl]benzamide hydrochloride,
N-(4-amino-2-methyl-6-quinolyl)-2-[(3-fluorophenoxy)methyl]benzamide hydrochloride,
N-(4-amino-2-methyl-6-quinolyl)-2-[(3-trifluoromethylphenoxy)methyl]benzamide hydrochloride,
methyl 4-[2-{N-(4-amino-2-methyl-6-quinolyl)carbamoyl}benzyloxy]benzoate hydrochloride,
N-(4-amino-2-methyl-6-quinolyl)-2-[(4-iodophenoxy)methyl]benzamide,
N-(4-amino-2-methyl-6-quinolyl)-2-(3-pyridyloxymethyl)benzamide hydrochloride,
4-[2-{(4-amino-2-methyl-6-quinolyl)carbamoyl}benzyloxy]benzoate hydrochloride,
N-(4-amino-2-methyl-6-quinolyl)-2-[(3-cyanophenoxy)methyl]benzamide hydrochloride,
N-(4-amino-2-methyl-6-quinolyl)-2-[(4-mesylphenoxy)methyl]benzamide hydrochloride,
N-(4-amino-2-methyl-6-quinolyl)-2-[(2-chloro-4-ethylphenoxy)methyl]benzamide hydrochloride,
N-(4-amino-2-methyl-6-quinolyl)-2-[(4-chloro-3-methylphenoxy)methyl]benzamide hydrochloride,
N-(4-amino-2-methyl-6-quinolyl)-2-[(2-chloro-4-methylphenoxy)methyl]benzamide hydrochloride,
N-(4-amino-2-methyl-6-quinolyl)-2-[(4-ethylphenoxy)methyl]benzamide,
N-(4-amino-2-methyl-6-quinolyl)-2-[(4-chloro-3-methylphenoxy)methyl]benzamide,
4-[2-{(4-amino-2-methyl-6-quinolyl)carbamoyl}benzyloxy]benzyl acetate hydrochloride,
N-(4-amino-2-methyl-6-quinolyl)-2-[(4-hydroxymethylphenoxy)methyl]benzamide hydrochloride and
N-(4-amino-2-methyl-6-quinolyl)-2-[(4-ethylphenoxy)methyl]benzamide hydrochloride monohydrate.

(9) An amide derivative of the formula [1″]

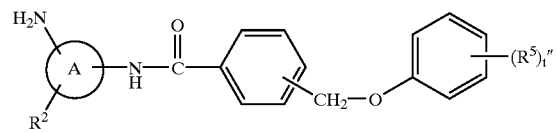

[1″]

wherein the ring A, $R^2$, $R^5$ and t are as defined in (1), or a pharmaceutically acceptable salt thereof.

(10) A pharmaceutical composition comprising the amide derivative of any of (5) to (9) or a pharmaceutically acceptable salt thereof and a pharmaceutically acceptable carrier.

(11) A nociceptin antagonist containing the amide derivative of any of (5) to (9) or a pharmaceutically acceptable salt thereof as an active ingredient.

(12) An analgesic containing the amide derivative of any of (1) to (9) or a pharmaceutically acceptable salt thereof as an active ingredient.

(13) A method for expressing a nociceptin antagonistic action, comprising administering the amide derivative of any of (1) to (9) or a pharmaceutically acceptable salt thereof.

(14) A method for treating pain, comprising administering the amide derivative of any of (1) to (9) or a pharmaceutically acceptable salt thereof.

(15) Use of the amide derivative of any of (1) to (9) or a pharmaceutically acceptable salt thereof for the production of a nociceptin antagonist.

(16) Use of the amide derivative of any of (1) to (9) or a pharmaceutically acceptable salt thereof for the production of an analgesic.

(17) A pharmaceutical composition for antagonizing nociceptin, which comprises the amide derivative of any of (1) to (9) or a pharmaceutically acceptable salt thereof and a pharmaceutically acceptable carrier.

(18) A commercial package comprising the pharmaceutical composition of (17) and a written matter associated therewith, the written matter stating that the pharmaceutical composition can be or should be used for antagonizing nociceptin.

(19) A pharmaceutical composition for analgesic use, which comprises the amide derivative of any of (1) to (9) or a pharmaceutically acceptable salt thereof and a pharmaceutically acceptable carrier.

(20) A commercial package comprising the pharmaceutical composition of (19) and a written matter associated therewith, the written matter stating that the pharmaceutical composition can be or should be used for analgesia.

Each substituent and moiety used in the present specification are defined as follows.

Halogen atom is fluorine atom, chlorine atom, bromine atom or iodine atom. At $R^3$, $R^4$, $R^5$ and $R^{5''}$, it is preferably chlorine atom.

Lower alkyl has linear or branched chain and 1 to 6 carbon atoms. Specific examples thereof include methyl, ethyl, propyl, isopropyl, butyl, isobutyl, sec-butyl, tert-butyl, pentyl, isopentyl, tert-pentyl, hexyl and the like.

It is preferably a linear or branched alkyl having 1 to 4 carbon atoms. At $R^3$, $R^4$, $R^7$, $R^9$, $R^{10}$, $R^{11}$ and $R^{2'}$, it is more preferably methyl and at $R^{5'}$, it is more preferably methyl or ethyl.

Lower alkoxy has an alkyl moiety defined above as lower alkyl. Specific examples include methoxy, ethoxy, propoxy, isopropyloxy, tert-butoxy and the like.

Lower alkylthio has an alkyl moiety defined above as lower alkyl. Specific examples include methylthio, ethylthio, propylthio, isopropylthio, tert-butylthio and the like.

Preferably, its alkyl moiety is a linear or branched alkyl having 1 to 4 carbon atoms. At $R^8$, it is more preferably methylthio.

Lower alkanoyl has an alkyl moiety defined above as lower alkyl. Specific examples include acetyl, propionyl, butyryl, isobutyryl, pivaloyl and the like.

Preferably, its alkyl moiety is a linear or branched alkyl having 1 to 4 carbon atoms. At $R^5$, it is more preferably acetyl.

Lower alkylsulfonyl has an alkyl moiety defined above as lower alkyl. Specific examples include mesyl, ethylsulfonyl, propylsulfonyl, isopropylsulfonyl, tert-butylsulfonyl and the like.

Preferably, its alkyl moiety is a linear or branched alkyl having 1 to 4 carbon atoms. At $R^5$, it is more preferably mesyl.

Lower alkanoyloxy has an alkyl moiety defined above as lower alkyl. Specific examples include acetoxy, propionyloxy, butyryloxy, isobutyryloxy, pivaloyloxy and the like.

Preferably, its alkyl moiety is a linear or branched alkyl having 1 to 4 carbon atoms. At $R^5$, it is more preferably acetoxy.

Lower alkoxycarbonyl has an alkyl moiety defined above as lower alkyl. Specific examples include methoxycarbonyl, ethoxycarbonyl, propoxycarbonyl, isopropyloxycarbonyl, tert-butoxycarbonyl and the like.

Preferably, its alkyl moiety is a linear or branched alkyl having 1 to 4 carbon atoms. At $R^5$, it is more preferably methoxycarbonyl, and at $R^7$, it is more preferably tert-butoxycarbonyl.

Lower alkyl optionally substituted by hydroxy means that the above-defined lower alkyl is optionally substituted by one or more hydroxy, and that the lower alkyl may be unsubstituted. Specific examples include methyl, ethyl, propyl, isopropyl, hydroxymethyl, 1,2-dihydroxyethyl, 2-(hydroxymethyl)butyl and the like.

$R^1$ and $R^2$ are preferably methyl, ethyl, propyl, isopropyl or hydroxymethyl, and more preferably methyl or ethyl.

Lower alkyl optionally substituted by lower alkoxy means the above-defined lower alkyl optionally substituted by the above-defined lower alkoxy, including unsubstituted alkyl. Specific examples include methyl, ethyl, methoxymethyl, ethoxymethyl, 2-(methoxymethyl)butyl and the like.

Preferably, its base alkyl moiety is a linear alkyl having 1 to 4 carbon atoms. At X, it is more preferably methoxymethyl.

Lower alkoxy optionally substituted by lower alkoxy means the above-defined lower alkoxy optionally substituted by the above-defined lower alkoxy, including unsubstituted alkoxy. Specific examples include methoxy, ethoxy, methoxymethoxy, methoxyethoxy, 2-(methoxymethyl)butyloxy and the like.

Preferably, its base alkyl moiety is a linear or branched alkyl having 1 to 4 carbon atoms. At $R^5$, it is more preferably methoxy or methoxymethoxy.

Lower alkyl optionally substituted by any of halogen atom, hydroxy, lower alkanoyloxy and lower alkoxy optionally substituted by lower alkoxy means that the above-defined lower alkyl is optionally substituted by one or more of the above-defined halogen atom, hydroxy, the above-defined lower alkanoyloxy and the above-defined lower alkoxy optionally substituted by lower alkoxy, each of which may be the same or different, and that the lower alkyl may be unsubstituted. Specific examples include methyl, ethyl, propyl, isopropyl, tert-butyl, hydroxymethyl, 2-hydroxyethyl, 1,2-dihydroxyethyl, acetoxymethyl, pivaloyloxymethyl, bromomethyl, trifluoromethyl, methoxymethoxymethyl, methoxyethoxymethyl and the like.

Preferably, its base alkyl moiety is a linear or branched alkyl having 1 to 4 carbon atoms. At $R^5$, it is more preferably methyl, ethyl, propyl, isopropyl, tert-butyl, hydroxymethyl, acetoxymethyl, trifluoromethyl or methoxymethoxymethyl and more preferably ethyl.

Lower alkylamino is a monoalkylamino group wherein the alkyl moiety is defined above as lower alkyl. Specific examples include methylamino, ethylamino, propylamino, isopropylamino, tert-butylamino and the like.

Preferably, its alkyl moiety is a linear or branched alkyl having 1 to 4 carbon atoms. At $R^1$ and $R^2$, it is more preferably methylamino.

Di(lower)alkylamino is a dialkylamino group wherein the alkyl moiety is the same or different and as defined above as lower alkyl. Specific examples include dimethylamino, diethylamino, methylethylamino, N-isopropyl N-isobutylamino and the like.

Preferably, its alkyl moiety is a linear or branched alkyl having 1 to 4 carbon atoms. At $R^1$, $R^2$ and $R^5$, it is more preferably dimethylamino.

Lower alkenyl is linear chain alkenyl having 1 to 6 carbon atoms. Examples thereof include vinyl, 1-propenyl, 2-propenyl, 1-butenyl, 2-butenyl, 3-butenyl, 1,3-butadienyl, 2,4-butadienyl, 1-pentenyl, 1,3-pentadienyl and 1,3,5-hexatrienyl and the like.

X is preferably vinyl.

Aryl is an aromatic hydrocarbon group having 6 to 18 carbon atoms. Examples thereof include phenyl, naphthyl, anthryl, indenyl, azulenyl, fluorenyl, phenanthryl, pyrenyl and the like.

Ring A is preferably phenyl and naphthyl, more preferably phenyl. Ring G and $R^6$ are preferably phenyl.

When ring G is phenyl, substituent $R^5$ is preferably bonded at para-position.

Heterocyclic ring is a cyclic compound group having one or more from oxygen atom, nitrogen atom and sulfur atom as hetero atom, wherein plural hetero atoms may be contained and the number of atoms constituting the ring is 5 to 20. Specific examples thereof include pyridyl, pyrazinyl, pyrimidinyl, pyrrolyl, thienyl, furyl, imidazolyl, pyrazolyl, oxazolyl, thiazolyl, quinolyl, isoquinolyl, indolyl, benzofuranyl, benzimidazolyl, imidazolidinyl, indolinyl, pyrrolidinyl, pyrolinyl, piperidinyl, piperazinyl, chromanyl, morpholinyl, phthalazinyl, naphthyridinyl, quinazolinyl, quinoxalyl, cinnolinyl, pteridinyl, 4H-quinolizinyl, carbazolyl, 1,3,5-triazinyl, 2,3-dihydrobenzofuranyl, 5,6,7,8-tetrahydroquinolyl, 5,6,7,8-tetrahydroacridinyl, 2,3-dihydro-1H-cyclopenta[b]quinolyl and the like.

Ring G is preferably pyridyl, benzofuranyl or 2,3-dihydrobenzofuranyl, more preferably 2,3-dihydrobenzofuranyl.

Ring A is preferably a cyclic compound group containing one or more nitrogen atoms as hetero atoms, and the number of atoms constituting the ring is 9 to 14. More preferably, it is quinolyl, isoquinolyl, quinoxalyl, benzimidazolyl, 5,6,7,8-tetrahydroquinolyl, 5,6,7,8-tetrahydroacridinyl or 2,3-dihydro- 1H-cyclopenta[b]quinolyl, most preferably quinolyl, 5,6,7,8-tetrahydroacridinyl or 2,3-dihydro-1H-cyclopenta[b]quinolyl.

When the ring A is quinolyl, it is preferable that $R^1$ be an amino group substituting at the 4-position, $R^2$ be a lower alkyl substituting at the 2-position and —NHCO— substitute at the 6-position.

Cycloalkyl is a saturated cycloalkyl having 3 to 8 carbon atoms, which is exemplified by cyclopropyl, cyclobutyl, cyclopentyl, cyclohexyl, cycloheptyl and cyclooctyl.

Ring G is preferably cyclohexyl.

Condensed aryl is the above-defined aryl wherein the above-defined cycloalkyl groups are condensed, which is a cyclic compound group wherein the number of atoms constituting the ring is 5 to 18. Specific examples include indanyl, 5,6,7,8-tetrahydro-2-naphthyl, 5,6,7,8-tetrahydro3-naphthyl, 1,2,3,4-tetrahydro-2-naphthyl, 5,6,7,8-tetrahydro-2-anthryl, 1,2,3-trihydroazulenyl and the like.

Ring G is preferably 5,6,7,8-tetrahydro-2-naphthyl.

Protected amino is an amino group protected by an amino-protecting group used in a typical chemical synthesis. Specific examples of the amino-protecting group include formyl, acetyl, benzoyl, benzyloxycarbonyl, methoxycarbonyl, tert-butoxycarbonyl, phthaloyl, benzyl, tosyl and the like.

Carboxy-protecting group is a carboxy-protecting group used in a typical chemical synthesis. Specific examples thereof include methyl, methoxyethoxymethyl, phenacyl, phthalimidomethyl, ethyl, 2,2,2-trichloroethyl, 2-methylthioethyl, tert-butyl, benzyl, p-nitrobenzyl, p-methoxybenzyl, tert-butyldimethylsilyl and the like.

Hydroxy-protecting group is a hydroxy-protecting group used in a typical chemical synthesis. Specific examples thereof include trimethylsilyl, tert-butyldimethylsilyl, methyl, benzyl, p-methoxybenzyl, tert-butyl, trityl, tetrahydropyranyl, methoxymethyl, methoxyethoxyethyl, acetyl, benzoyl and the like.

In the above-mentioned formnulas [1], [1'] and [1"], each symbol preferably means the following.

Ring G is preferably aryl.

$R^5$ is preferably halogen atom; lower alkyl optionally substituted by any of halogen atom, hydroxy, lower alkanoyloxy and lower alkoxy optionally substituted by lower alkoxy; lower alkoxy optionally substituted by lower alkoxy; nitro; cyano; or lower alkanoyl, and more preferably lower alkyl optionally substituted by any of halogen atom, hydroxy, lower alkanoyloxy and lower alkoxy optionally substituted by lower alkoxy.

The t is preferably 0 or an integer of 1 or 2, more preferably 1.

The E is preferably a single bond or —O—, more preferably —O—.

When E is —O—, m is preferably an integer of 1 to 7, more preferably 1, and n is preferably 0. When E is a single bond, m+n is preferably 2.

The compound of the formula [1] includes various isomers. For example, there exist geometric E- and Z-isomers. When asymmetrical carbon atom(s) exist(s), stereoisomers (e.g., enantiomer and diastereomer) exist. Depending on the case, tautomers may exist in the present invention. Therefore, the present invention encompasses all these isomers and mixtures thereof.

The pharmaceutically acceptable salt thereof may be any salt as long as it can form a nontoxic salt with the compound of the above-mentioned formula [1], [1'] or [1"]. Examples thereof include salts with inorganic acid such as hydrochloric acid, sulfuric acid, phosphoric acid, hydrobromic acid and the like; salts with organic acid such as oxalic acid, malonic acid, citric acid, fumaric acid, lactic acid, malic acid, succinic acid, tartaric acid, acetic acid, gluconic acid, ascorbic acid, methylsulfonic acid, benzylsulfonic acid and the like; salts with inorganic base such as sodium hydroxide, potassium hydroxide, calcium hydroxide, magnesium hydroxide, ammonium hydroxide and the like; salts with organic base such as methylamine, diethylamine, triethylamine, triethanolamine, ethylenediamine, tris(hydroxymethyl)methylamine, guanidine, choline, cinchonine and the like; or salts with amino acid such as lysine, alginine, alanine and the like. The present invention further encompasses water-containing compounds and hydrates and solvates of each compound.

The present invention further encompasses prodrugs and metabolites of each compound. Prodrug is a derivative of the compound of the present invention, which has a chemically or metabolically decomposable group and which shows efficacy upon restoration to its original form after administration to a body, wherein included therein are a complex without a covalent bond and salts.

When the compound of the present invention is used as a pharmaceutical preparation, it is generally admixed with conventionally known pharmaceutically acceptable carrier, excipient, diluent, extender, disintegrator, stabilizer, preservative, buffer, emulsifier, aromatic, coloring agent, sweetener, tackifier, flavor, solubilizer and other additive, specifically water, vegetable oil, alcohol (e.g., ethanol, benzyl alcohol and the like), polyethylene glycol, glycerol triacetate, gelatin, carbohydrate (e.g., lactose, starch and the like), magnesium stearate, talc, lanolin, petrolatum and the like, and formulated into tablets, pills, powders, granules, suppositories, injections, eye drops, liquids, capsules, troches, aerosols, elixirs, suspensions, emulsions, syrups and the like by a conventional method, which can be administered systemically or locally by oral or parenteral administration.

While the dose varies depending on age, body weight, symptom, therapeutic effect, administration route and the like, it is generally 0.01 mg to 1 g per dose which is given once to several times a day for an adult.

One example of the production method of the compound to practice the present invention is explained in the following, to which the production method of the compound of the present invention is not limited.

In each step, the treatment of reaction may be a conventional one, such as isolation and purification, crystallization, recrystallization, silica gel column chromatography, preparative HPLC and the like, which may be appropriately selected and combined. Where necessary, a protecting group may be introduced into a functional group and deprotected for production.

Production Method 1

A synthetic method of the compound of the following formula [I] is shown in the following.

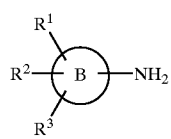

[I]

wherein ring A, $R^1$, $R^2$ and $R^3$ are as defined above.

When ring A is a quinoline ring, the quinoline synthetic method of Camps, the quinoline synthetic method of Combes, the quinoline synthetic method of Friedlander, the quinoline synthetic method of Knorr, the quinoline synthetic method of Niementowski and the like can be used for synthesis. A part of the compound can be obtained as a commercially available reagent.

The Production methods of quinoline ring having substituent are show in the following.

Production Method 1-1

In this production method, β-keto acid ester and aniline compound are reacted to give 4-hydroxyquinoline compound.

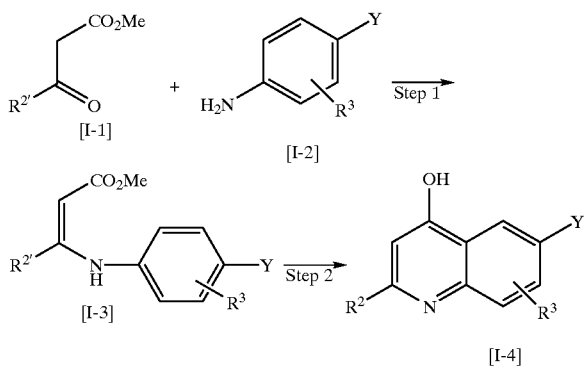

wherein $R^3$ is as defined above, $R^{2'}$ is lower alkyl and Y is nitro or protected amino.

Step 1

Compound [I-1] and compound [I-2] are condensed in an alcohol solvent, such as methanol, ethanol, n-propanol, isopropanol and the like, at room temperature or under heating to give compound [I-3].

Step 2

Compound [I-3] obtained in Production method 1-1, Step 1 is added by portions to a heated solvent and cyclized to give compound [I-4].

Preferable solvent is diphenyl ether or a mixture of diphenyl ether and diphenyl such as Dowtherm A (trademark Fluka).

This production method can be applied to compound [I-1] wherein the α-position of β-keto acid ester is substituted by lower alkyl.

Production Method 1-2

According to this production method, quinoline compound is obtained from isatin compound.

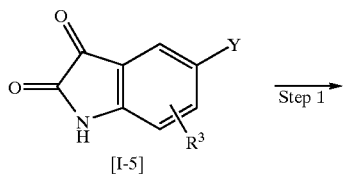

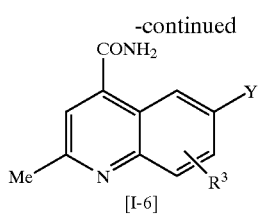

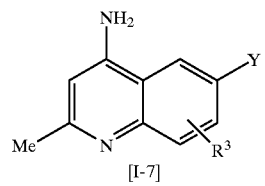

wherein $R^3$ and Y are as defined above.

Step 1

Compound [I-5], acetone and aqueous ammonia are reacted under pressurization and under heating to give compound [I-6].

Step 2

Compound [I-6] obtained in Production method 1-2, Step 1 is reacted in the presence of oxidizing agent, such as sodium hypochlorite, sodium hypobromite and the like, under cooling, and the obtained reaction mixture is added dropwise into hot water and further heated to give compound [I-7].

The following production method can be used to introduce a specific substituent or into a specific substitution site.

Production Method 1-3

According to this production method, 4-hydroxy-2-methoxycarbonylquinoline compound is obtained from acetylenedicarboxylate compound and aniline compound. The methoxycarbonyl group of this compound can be converted to hydroxymethyl group by reduction in a later step.

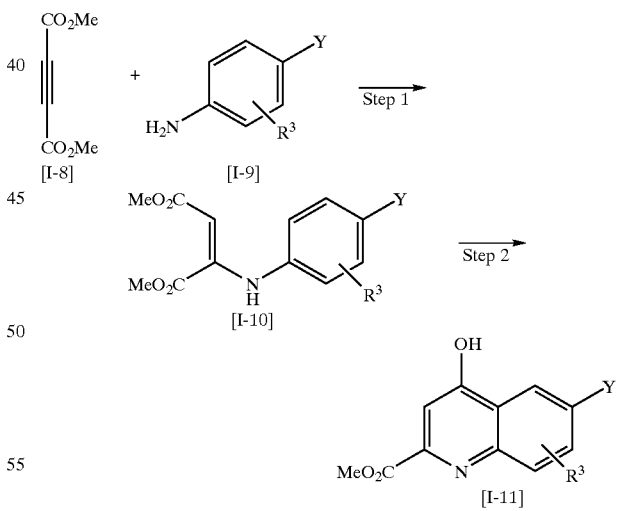

wherein $R^3$ and Y are as defined above.

Step 1

Compound [I-8] and compound [I-9] are condensed in the same manner as in Production method 1-1, Step 1 to give compound [I-10].

Step 2

Compound [I-10] obtained in Production method 1-3, Step 1 is cyclized in the same manner as in Production method 1-1, Step 2 to give compound [I-11].

Production Method 14

According to this production method, 4,6-diaminoquinoline compound is obtained from 4-nitroquinoline N-oxide compound.

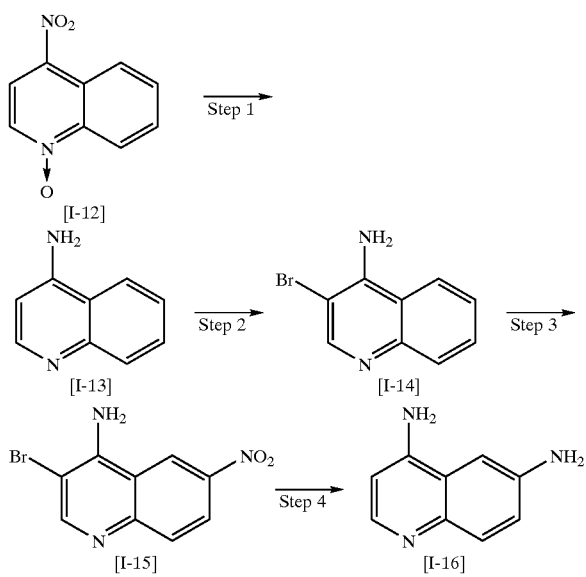

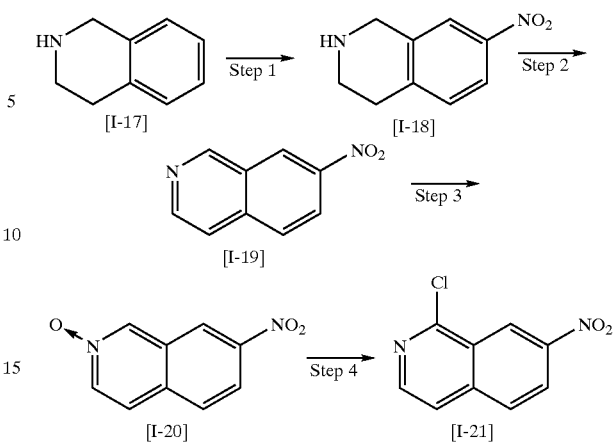

Step 1

Compound [I-12] and metal iron are reacted in an acid solvent, such as hydrochloric acid, acetic acid and the like, under heating and the resulting solution is made alkaline to give compound [I-13].

Alternatively, a typical reduction using tin or tin (II) chloride and conc. hydrochloric acid; alkaline metal sulfide such as aqueous sodium sulfide solution; catalytic reduction and the like may be used.

Step 2

Compound [I-13] obtained in Production method 1-4, Step 1 is treated with bromine in acetic acid under cooling or at room temperature to halogenate to give compound [I-14].

Alternatively, halogenating agent such as hypohalite (e.g., hypochlorite and the like), N-bromosuccinimide and the like can be used instead of bromine for halogenation.

Step 3

Compound [I-14] obtained in Production method 1-4, Step 2 is subjected to nitration in a sulfuric acid solvent under cooling by adding conc. nitric acid to give compound [I-15].

Nitric acid or inorganic nitrate-sulfuric acid may be used instead of a mixture of nitric acid-sulfuric acid for nitration.

Step 4

Compound [I-15] obtained in Production method 1-4, Step 3 is subjected to catalytic reduction using a hydrogenating catalyst in an alcohol solvent such as methanol, ethanol, n-propanol, isopropanol and the like by adding hydrochloric acid or hydrogen bromide-acetic acid solution at room temperature or under heating under normal pressure to high pressure to give compound [I-16].

Examples of hydrogenating catalyst include palladium carbon, palladium hydroxide, palladium black, Raney-nickel, platinum oxide and the like.

Examples of synthesis when ring A is isoquinoline ring are shown in the following.

Production method 1-5

According to this production method, 1-halogeno-7-nitroisoquinoline is obtained from tetrahydroisoquinoline.

Step 1

Compound [I-17] is subjected to nitration in the same manner as in Production method 1-4, Step 3 to give compound [I-18].

Step 2

Compound [I-18] obtained in Production method 1-5, Step 1 is subjected to dehydrogenation for a few days using Fremy's salt in 4% aqueous sodium carbonate solution at room temperature to give compound [I-19].

Step 3

Compound [I-19] obtained in Production method 1-5, Step 2 is reacted with m-chloroperbenzoic acid in a halogen solvent, such as dichloromethane, chloroform, carbon tetrachloride and the like, at room temperature for N-oxidation to give compound [I-20].

Step 4

Compound [I-20] obtained in Production method 1-5, Step 3 is reacted with phosphorus oxychloride in a hydrocarbon solvent, such as toluene, xylene and the like, under heating to give compound [I-21].

Production Method 1-6

According to this production method, quinoline compound condensed with cycloalkyl is obtained by condensation of saturated cyclic ketone and anthranilonitrile compound.

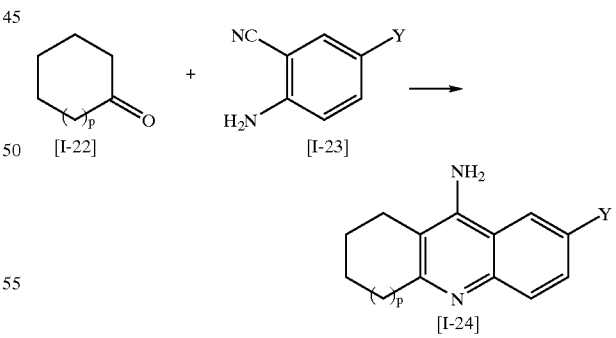

wherein Y is as defined above and p is 0 or an integer of 1.

An acid catalyst such as Lewis acid (e.g., zinc chloride) is added to a mixture of Compound [I-22] and compound [I-23] under heating for condensation to give compound [I-24].

Production Method 1-7

According to this production method, a substituent of a compound is substituted by amino group or substituted amino group.

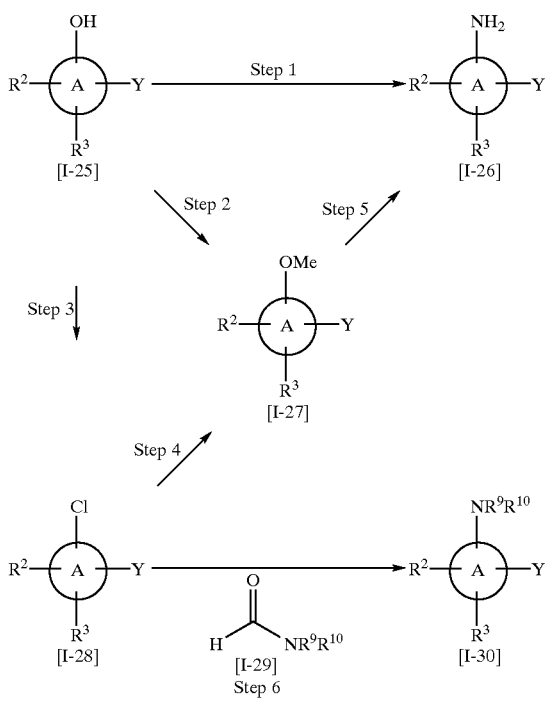

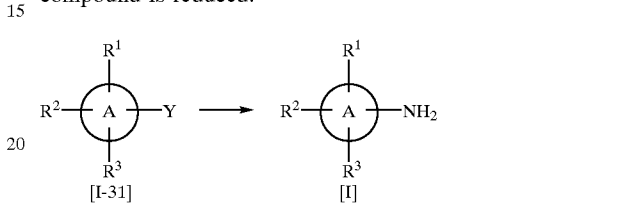

wherein ring A, $R^2$, $R^3$ and Y are as defined above, $R^9$ is hydrogen atom or lower alkyl and $R^2$ is lower alkyl.

Step 1

Compound [I-25] obtained in Production method 1-1 or a commercially available reagent is reacted with chlorosulfonyl isocyanate in acetonitrile or dichloroethane under heating to give compound [I-26].

Step 2

Compound [I-25] obtained in Production method 1-1 or a commercially available reagent is reacted with an alkylating agent in a solvent under heating or at room temperature to give compound [I-27].

As the alkylating agent, dimethyl sulfate or methyl p-toluenesulfonate is used to introduce methoxy group in the scheme.

Examples of preferable solvent include hydrocarbon solvent such as benzene, toluene, hexane, xylene and the like; and ether solvent such as 1,4-dioxane, diethyl ether, 1,2-dimethoxyethane, tetrahydrofuran and the like.

Step 3

Compound [I-25] obtained in Production method 1-1 or a commercially available reagent is reacted with halogenating agent, such as phosphorus oxychloride, phosphorus pentachloride and the like, under heating and the reaction mixture is made alkaline to give compound [I-28].

Step 4

Compound [I-28] obtained in Production method 1-5 or Production method 1-7, Step 3 or commercially available reagent is reacted with metal alkoxide in an alcohol solvent, such as methanol, ethanol, propanol, butanol and the like, under heating to give compound [I-27].

As the metal alkoxide, sodium methoxide is used and as the solvent, methanol is used as the corresponding alcohol solvent to introduce methoxy shown in the scheme.

Step 5

Compound [I-27] obtained in Production method 1-7, Step 2 or Production method 1-7, Step 4 or commercially available reagent is reacted with aminating agent such as ammonium acetate and the like under heating to give compound [I-26].

Step 6

Compound [I-28] obtained in Production method 1-7, Step 3 or commercially available reagent is reacted with compound [I-29] in the presence of a base, such as potassium carbonate, sodium carbonate, sodium hydroxide, potassium hydroxide, lithium hydroxide and the like, under heating to give compound [I-30].

The compound [I-25] in this Production method 1-7 may be compound [I-11] obtained in Production method 1-3.

Production Method 1-8

According to this production method, amino-protecting group of a compound is eliminated or nitro group of a compound is reduced.

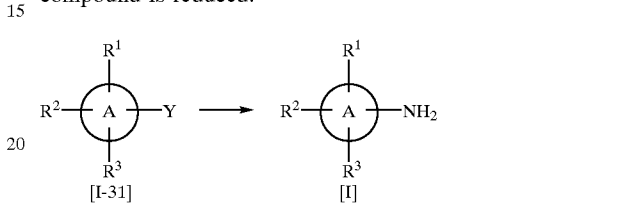

wherein ring A, $R^1$, $R^2$, W and Y are as defined above.

When Y is a protected amino, a typical deprotection method corresponding to the protecting group is used.

For example, when the protecting group is acetyl, conc. hydrochloric acid is added to compound [I-31] obtained in Production method 1-7 or a commercially available reagent, and the mixture is heated for deacetylation to give compound [I].

Instead of conc. hydrochloric acid treatment, heating in conc. ammonia, potassium hydroxide treatment and the like may be used.

When Y is nitro, a typical method of conversion to amine by reduction of nitro is used. For example, compound [I-31] obtained in Production method 1-7 or commercially available reagent is subjected to catalytic reduction in a solvent at room temperature or under heating, at normal pressure or high pressure using a hydrogenating catalyst to give compound [I].

Examples of the solvent include ether solvent such as 1,4-dioxane, diethyl ether, 1,2-dimethoxyethane, tetrahydrofuran and the like; polar solvent such as dimethylformamide, dimethyl sulfoxide, acetonitrile, acetone and the like; alcohol solvent such as methanol, ethanol, propanol, butanol and the like; ester such as ethyl formate, ethyl acetate, butyl acetate and the like; water; or a mixed solvent thereof.

The hydrogenating catalyst is exemplified by palladium carbon, palladium hydroxide, palladium black, Raney-nickel, platinum oxide and the like.

Production Method 2

The synthetic method of the compound of the formula [II] is shown in the following.

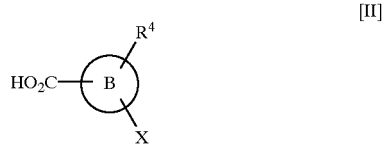

wherein ring B, $R^4$ and X are as defined above.

When X is a group of the formula

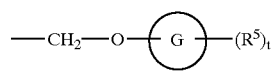

wherein ring G, $R^5$ and t are as defined above, the following Production method is exemplified.

Production Method 2-1

According to this production method, methyl of a methyl-substituted carboxylic acid compound is converted to ether.

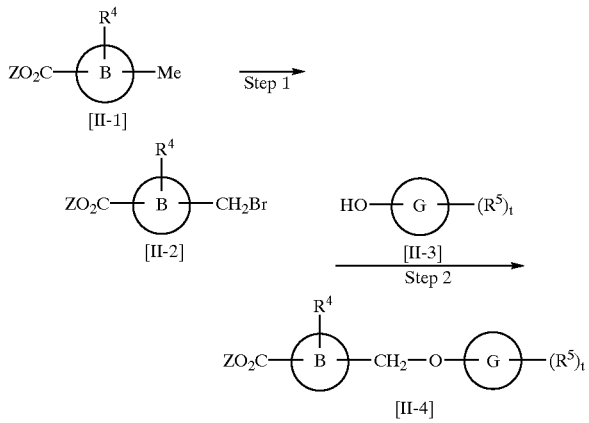

wherein ring B, ring G, $R^4$, $R^5$ and t are as defined above, and Z is a carboxy-protecting group.

Step 1

Compound [II-1] is reacted with radical initiator such as benzoyl peroxide, azobisisobutyronitrile and the like and N-bromosuccinimide to give compound [II-2].

Step 2

Compound [II-2] obtained in Production method 2-1, Step 1 is reacted with compound [II-3] in a solvent in the presence of a base, such as potassium carbonate, sodium carbonate, lithium hydroxide, sodium hydroxide, potassium hydroxide, lithium hydride, sodium hydride, potassium hydride and the like, under heating to give compound [II-4].

Examples of the solvent include hydrocarbon solvent such as benzene, toluene, hexane, xylene and the like; ether solvent such as 1,4-dioxane, diethylether, 1,2-dimethoxyethane, tetrahydrofuran and the like; polar solvent such as dimethylformamide, dimethyl sulfoxide, acetonitrile, acetone and the like; and alcohol solvent such as methanol, ethanol, propanol, butanol and the like.

Most of compound [II-3] can be easily obtained as a commercially available reagent but a compound difficult to obtain can be synthesized by the following production methods.

Production Method 2-2

According to this production method, a cyclic compound having a substituent is substituted by halogen atom.

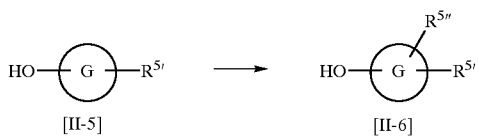

wherein ring G is as defined above, $R^{5'}$ is lower alkyl and $R^{5''}$ is halogen atom.

In the same manner as in Production method 1-4, Step 2, compound [II-5] is halogenated to give compound [II-6].

Using sulfuryl chloride as the halogenating agent, the compound is halogenated in a halogen solvent, such as dichloromethane, chloroform, carbon tetrachloride, tetrachloroethylene and the like, to substitute chlorine atom at the ortho-position of 4-alkyl substituted phenol.

Production Method 2-3

According to this production method, a cyclic compound is substituted by alkylsulfonyl.

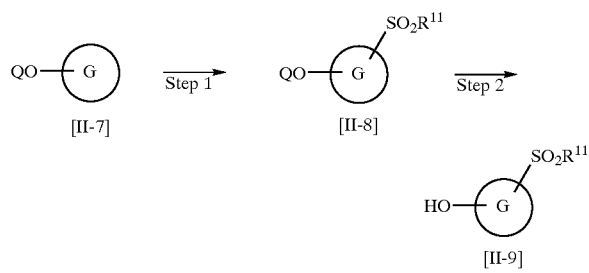

wherein ring G is as defined above, Q is a hydroxy-protecting group and $R^{11}$ is lower alkyl.

Step 1

Compound [II-7] is reacted with alkylsulfonic anhydride, such as methanesulfonic anhydride, in a halogen solvent, such as dichloromethane, chloroform, carbon tetrachloride, tetrachloroethylene and the like, under heating to give compound [II-8].

Step 2

Compound [II-8] obtained in Production method 2-3, Step 1 is deprotected by a conventional method to give compound [II-9].

For example, when $R^{11}$ is methyl, aqueous hydrogen bromide is added and heated, or heated with sodium cyanide in dimethyl sulfoxide to allow deprotection.

Production Method 2-4

According to this production method, benzofuran compound or 2,3-dihydrobenzofuran compound is synthesized from phenol compound.

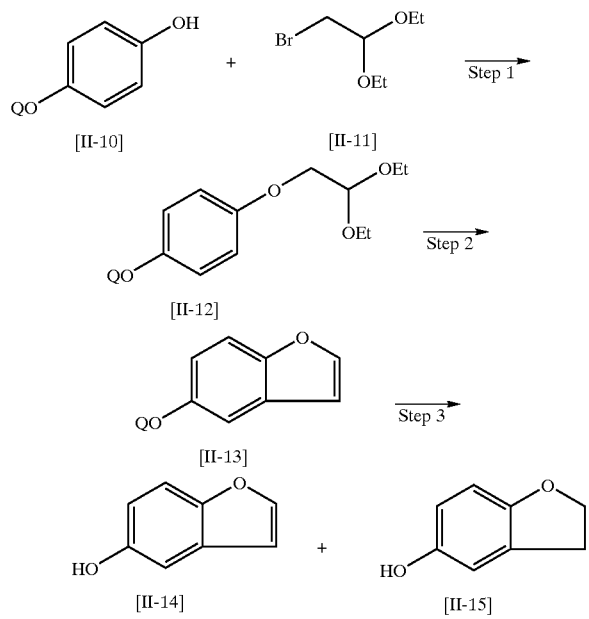

wherein Q is as defined above.

Step 1

Compound [II-10] is condensed with compound [II-11] in a polar solvent, such as dimethylformamide, dimethyl sulfoxide, acetonitrile, acetone and the like, in the presence of a base, such as potassium carbonate, sodium carbonate, lithium hydroxide, sodium hydroxide, potassium hydroxide, lithium hydride, sodium hydride, potassium hydride and the like, under heating to give compound [II-12].

Step 2

Compound [II-12] obtained in Production method 2-4, Step 1 is cyclized using an agent for condensation, such as polyphosphoric acid and the like, in a hydrocarbon solvent, such as benzene, toluene, hexane, xylene and the like, under heating to give compound II-13].

Step 3

Compound [II-13] obtained in Production method 2-4, Step 2 is subjected to catalytic reduction in the same manner as in Production method 1-4, Step 4 to give compounds [II-14] and [II-15].

Examples of the solvent include, besides alcohol solvents, ether solvents such as 1,4-dioxane, diethyl ether, 1,2-dimethoxyethane, tetrahydrofuran and the like and a mixed solvent thereof and the like.

Production Method 2-5

According to this production method, a carboxy-protecting group is eliminiated from a compound.

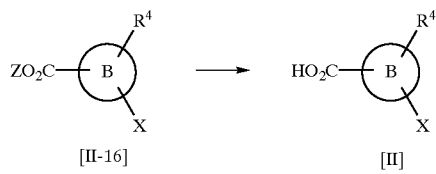

wherein ring B, $R^4$, X and Z are as defined above.

The carboxy-protecting group can be eliminated by a conventional deprotection method depending on the kind of protecting group.

For example, when Z is methyl, compound [II-16] is reacted in an alcohol solvent, such as methanol, ethanol, n-propanol, isopropanol and the like, in the presence of a base, such as potassium carbonate, sodium carbonate, lithium hydroxide, sodium hydroxide, potassium hydroxide and the like, under heating for deprotection, and the resulting solution is acidified to give compound [II].

Production Method 3

According to this production method, amine compound and carboxylic acid compound are condensed to amine.

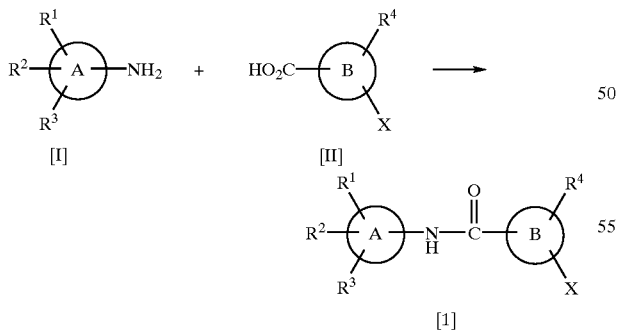

wherein ring A, ring B, $R^1$, $R^2$, $R^3$, $R^4$ and X are as defined above.

Compound [I] obtained in Production method 1 or a commercially available reagent and compound [II] obtained in Production method 2 or a commercially available reagent are condensed by a conventional method of formation of amide by condensation.

For example, compound [II] is treated with a halogenating agent, such as oxalyl chloride, thionyl chloride, phosphorus oxychloride, phosphorus pentachloride and the like, in a solvent at room temperature to give the corresponding acid chloride. Then, the compound is condensed with compound [I] in the presence of a tertiary amine, such as triethylamine and the like, or pyridine at room temperature or under cooling to give compound [1].

Examples of preferable solvent include halogen solvents such as dichloromethane, chloroform, carbon tetrachloride, 1,2-dichloroethane and the like; ether solvents such as 1,4-dioxane, diethyl ether, 1,2-dimethoxyethane, tetrahydrofuran and the like.

Alternatively, compound [I] and compound [II] are reacted in a solvent in the presence of an agent for condensation at room temperature to give compound [1]. For smooth reaction, an enhancer may be used.

Examples of the agent for condensation include N,N'-carbonyldiimidazole, N,N'-dicyclohexylcarbodiimide, N,N'-disopropylcarbodiimide, 1-(3-dimethylaminopropyl)-3-ethylcarbodiimide hydrochloride (EDC) and the like and examples of the enhancer include hydroxysuccinimide, 1-hydroxybenzotriazole and the like.

Examples of preferable solvent include a hydrocarbon solvent such as benzene, toluene, hexane, xylene and the like; a halogen solvent such as dichloromethane, chloroform, carbon tetrachloride, 1,2-dichloroethane and the like; an ether solvent such as 1,4-dioxane, diethyl ether, 1,2-dimethoxyethane, tetrahydrofuran and the like; a polar solvent such as dimethylformamide, dimethyl sulfoxide, acetonitrile and the like; and a mixed solvent thereof.

For an improvement of the yield, reduction of cost and the like to lead to higher production efficiency, reduction, deprotection and the like may be carried out after formation of amide by condensation.

For example, when compound [I] or compound [II] has a nitro group, the nitro group may be reduced after formation of amide by condensation, or when compound [II] and compound [II] have a functional group such as hydroxy and the like, deprotection may be carried out after formation of amide by condensation.

Alternatively, methoxycarbonyl-substituted compound obtained in Production method 1-3 and Production method 3 is added to an ether solvent, such as 1,4-dioxane, diethyl ether, 1,2-dimethoxyethane, tetrahydrofuran and the like, and lithium tetrahydroborate is added by portions in an argon stream under cooling for reduction to give hydroxymethyl-substituted compound.

EXAMPLES

The compound of the formula [1] of the present invention and the production method thereof are specifically explained in the following by way of examples. It is needless to say that the present invention is not limited to these examples.

Preparation Example 1-1

Synthesis of 4,6-diamino-2-methylquinoline

The synthesis was carried out according to a reference publication (Journal of the American Chemical Society, 70, 4065, 1948).

Step 1

4-Aminoacetoanilide (150.2 g, 1 mol) was added to a solution of methyl acetoacetate (136.8 g, 1.1 mol) in methanol (450 ml) and the mixture was refluxed under heating for 17 hours. The reaction vessel was cooled to 0° C. and the resulting white precipitate was collected by filtration to give methyl β-(p-acetamidophenylamino)crotonate (231.5 g, 93%, white crystals).

Step 2

Methyl β-(p-acetamidophenylamino)crotonate (231.5 g, 0.93 mol) obtained in Preparation Example 1-1, Step 1 was added by small portions to Dowtherm A (trademark, 600 ml) which underwent refluxing under heating. The mixture was refluxed under heating for 10 minutes and the reaction mixture was cooled to room temperature. The resulting precipitate was collected by filtration and washed with ethyl acetate. The obtained crude crystals were suspended in methanol and collected by filtration to give N-(4-hydroxy-2-methyl-6-quinolyl)acetamide (178.3 g, 88%, deep yellow crystals).

Step 3

To a suspension of N-(4-hydroxy-2-methyl-6-quinolyl) acetamide (100 g, 0.46 mol) obtained in Preparation Example 1-1, Step 2 in toluene (490 ml) was added dimethyl sulfate (75 ml, 0.79 mol) and the mixture was refluxed under heating for 8 hr. The resulting precipitate was collected by filtration, dissolved in water (1350 ml) and heated to 70° C. The solution was filtered and 35% aqueous sodium hydroxide solution (100 ml) was added to the filtrate. The resulting precipitate was collected by filtration to give N-(4-methoxy-2-methyl-6-quinolyl)acetamide (55.3 g, 52%, pale-brown crystals).

Step 4

N-(4-Methoxy-2-methyl-6-quinolyl)acetamide (55.6 g, 0.24 mol) obtained in Preparation Example 1-1, Step 3 was mixed with ammonium acetate (279.4 g, 3.62 mol) and the mixture was stirred under heating at 135° C. for 4 hours. To the reaction mixture were added water (280 ml) and conc. hydrochloric acid (450 ml) and the mixture was stirred under heating at 90° C. for 5 hr. The reaction mixture was cooled to 0° C. and the resulting precipitate was collected by filtration. The obtained crystals were dissolved in hot water and treated with active charcoal and filtered. To the filtrate was added 35% aqueous sodium hydroxide solution while cooling with ice. The resulting precipitate was collected by filtration, washed with water and dried under reduced pressure at 100° C. to give the title compound (28.4 g, 68%, pale-yellow crystals).

Preparation Example 1-2

Synthesis of 4,6-diamino-2-methylquinoline

Step 1

To 5-nitroisatin (19.21 g, 0.1 mol) were added acetone (36.7 ml, 0.5 mol) and aqueous ammonia (100 ml) and the mixture was heated in an autoclave at 100° C. for 12 hr. The reaction mixture was cooled to room temperature and the resulting crystals were collected by filtration and washed with water. The obtained crystals were dried by heating under reduced pressure to give 2-methyl-6-nitroquinoline-4-carboxamide (18.30 g, 79%).

Step 2

To 2-methyl-6-nitroquinoline-4-carboxamide (231 mg, 1 mmol) obtained in Preparation Example 1-2, Step 1 was added an aqueous sodium hypochlorite solution (0.851 ml, 1.2 mmol) and the mixture was stirred at 0° C. for 2.5 hr. The reaction mixture was added dropwise to hot water (10 ml) under reflux with heating and the mixture was refluxed under heating for 20 min. The reaction mixture was cooled to room temperature and the resulting crystals were collected by filtration and dried by heating under reduced pressure to give 4-amino-2-methyl-6-nitroquinoline (177 mg, 87%).

Step 3

4-Amino-2-methyl-6-nitroquinoline (337 mg, 1.7 mmol) obtained in the same manner as in Preparation Example 1-2, Step 2 was dissolved in methanol (15 ml) and thereto was added 10% palladium carbon (200 mg) and the mixture was stirred at room temperature at 3 atm under a hydrogen atmosphere for 15 hr. The reaction mixture was filtered through celite by suction and the filtrate was concentrated under reduced pressure to give the title compound (200 mg, 70%).

Preparation Example 1-3

Synthesis of 6-amino-2-methyl-4-methylaminoquinoline

Step 1

N-(4-Hydroxy-2-methyl-6-quinolyl)acetamide (4.32 g, 20 mmol) and phosphorus oxychloride (9.32 ml, 100 mmol) were heated at 100° C. for 15 min. The reaction mixture was cooled to room temperature and poured into ice water. Thereto was added 28% aqueous ammonia to make the solution alkaline. The resulting insoluble matter was collected by filtration, washed with ether and water, dried under reduced pressure at 80° C. to give N-(4-chloro-2-methyl-6-quinolyl)acetamide (6.85 g, crude, yellow solid).

Step 2

A suspension of N-(4-chloro-2-methyl-6-quinolyl) acetamide (4.0 g, crude) obtained in Preparation Example 1-3, Step 1 and 85% potassium hydroxide (6.6 g, 100 mmol) in N-methylformamide (100 ml) was heated at 170° C. for 3 hr 20 min. The reaction mixture was cooled to room temperature and the reaction mixture was diluted with chloroform and water. The chloroform layer was washed successively with saturated aqueous sodium hydrogencarbonate solution, water and saturated brine, dried over sodium sulfate and concentrated under reduced pressure. The obtained black oil was purified by silica gel column chromatography (chloroform:methanol= 85:15→chloroform:methanol:28% aqueous ammonia= 85:15:0.1) to give N-(2-methyl-4-methylamino-6-quinolyl) acetamide (255 mg, 9.5% from N-(4-hydroxy-2-methyl-6-quinolyl)acetamide) as a pale-brown solid.

Step 3

N-(2-methyl-4-methylamino-6-quinolyl)acetamide (248 mg, 1.08 mmol) obtained in Preparation Example 1-3, Step 2 was refluxed under heating for 2 hr in 6N hydrochloric acid (10 ml). The reaction mixture was cooled to room temperature and 4N aqueous sodium hydroxide solution was added to make the pH not lower than 13, followed by ice-cooling. The resulting insoluble matter was collected by filtration and dried under reduced pressure at 60° C. to give the title compound (202 mg, 99.7%, pale-yellow solid).

Preparation Example 1–4

Synthesis of 4,6-diaminoquinoline dihydrobromide

The syntheses from Step 2 to Step 4 followed the method of a reference publication (Yakugah Zassh, 72, 665, 1952).

Step 1

A suspension of 4-nitroquinoline N-oxide (10 g, 52.5 mmol) and metal iron (26.4 g, 0.47 mol) in acetic acid (500 ml) was stirred under heating at 110° C. for 3 hr. The reaction mixture was filtered and the filtrate was concentrated under reduced pressure. To the residue was added an aqueous sodium hydroxide solution to make the solution alkaline, which was followed by extraction with chloroform (5 ml×6). The orgariic layer was washed with water and saturated brine, dried over sodium sulfate and concentrated under reduced pressure to give 4-aminoquinoline (6.0 g, 79%, brown crystals).

Step 2

To a solution of 4-aminoquinoline (2.28 g, 15.8 mmol) obtained in Preparation Example 14, Step 1 in acetic acid (30 ml) was added bromine (2.78 g, 17.4 mmol) with stirring under ice-cooling and the mixture was stirred at room temperature for 30 min. Diethyl ether was added and the resulting precipitate was collected by filtration to give 4-amino-3-bromoquinoline hydrobromide (4.39 g, 91%). The obtained crystals were dissolved in water and 1N aqueous sodium hydroxide solution was added to make the solution alkaline. The resulting precipitate was collected by filtration, washed with water and dried under reduced pressure to give 4-amino-3-bromoquinoline (2.91 g, 82%, pale-gray crystals).

Step 3

To a solution of 4-amino-3-bromoquinoline (2.90 g, 13 mmol) obtained in Preparation Example 14, Step 2 in conc. sulfuric acid (25 ml) was added 60% nitric acid (1.5 ml, 20 mmol) with stirring under ice-cooling, and the mixture was stirred for 1 hr. To the reaction mixture was added sodium hydroxide (40 g) under ice-cooling and the resulting precipitate was collected by filtration. The obtained crystals were dissolved in acetone, treated with active charcoal and recrystallized to give 4-amino-3-bromo-6-nitroquinoline (1.65 g, 47%, yellow crystals).

Step 4

To a solution of 4-amino-3-bromo-6-nitroquinoline (0.82 g, 3.05 mmol) obtained in Preparation Example 14, Step 3 in ethanol (30 ml) were added 25% hydrogen bromide-acetic acid solution (0.7 ml, 3.05 mmol) and 10% palladium carbon catalyst and the mixture was subjected to catalytic reduction at room temperature for 6 hr. The catalyst was filtered off and washed with water. The filtrate was concentrated under reduced pressure. The obtained residue was recrystallized from water-ethanol-ethyl acetate to give the title compound (0.92 g, 94%, green brown crystals).

Preparation Example 1-5

Synthesis of 1,7-diaminoisoquinoline

Step 1

Conc. sulfuric acid (80 ml) was added by small portions to tetrahydroisoquinoline (24.4 g, 183 mmol) under ice-cooling for dissolution. Then, 60% nitric acid (18 ml) was added dropwise from a funnel and the mixture was stirred under ice-cooling for 3 hr. The mixture was stirred at room temperature for 18 hr. The reaction mixture was diluted with water under ice-cooling, and 35% aqueous sodium hydroxide solution was added to adjust the solution to pH 12. After extraction with chloroform, the organic layer was washed with water, dried over anhydrous magnesium sulfate and concentrated under reduced pressure. The residue was dissolved in ethanol (180 ml) and conc. hydrochloric acid (20 ml) was added under ice-cooling. The precipitated brown crystals were collected by filtration with suction to give 7-nitrotetrahydroisoquinoline hydrochloride (7.18 g, 22%).

Step 2

To 7-nitrotetrahydroisoquinoline hydrochloride (7.18 g, 33 mmol) obtained in Preparation Example 1-5, Step 1 was added Fremy's salt (100 g, 280 mmol) in 4% aqueous sodium carbonate solution (1.5 L). The mixture was stirred at room temperature for 7 days and the reaction mixture was extracted with chloroform, dried over anhydrous magnesium sulfate and concentrated under reduced pressure. The residue was purified by neutral alumina column chromatography (hexane:ethyl acetate=3:2) to give 7-nitroisoquinoline (3.21 g, 55%).

Step 3

To a solution of 7-nitroisoquinoline (2.38 g, 14 mmol) obtained in Preparation Example 1-5, Step 2 in chloroform (68 ml) was added m-chloroperbenzoic acid (3.54 g, 21 mmol). The mixture was stirred at room temperature for 21 hr. The insoluble matter in chloroform was filtered off with suction and washed with chloroform. The filtrate was washed with aqueous sodium hydrogencarbonate solution and saturated brine, dried over anhydrous magnesium sulfate, and concentrated under reduced pressure to give 7-nitroisoquinoline N-oxide. The obtained compound was used in the next reaction without purification.

Step 4

To a suspension of 7-nitroisoquinoline N-oxide obtained in Preparation Example 1-5, Step 3 in toluene (185 ml) was added phosphorus oxychloride (3.5 ml, 37 mmol), and the mixture was stirred under heating at 90° C. for 2 hr. The reaction mixture was cooled to room temperature and the reaction mixture was poured into an aqueous sodium hydrogencarbonate solution. The aqueous layer was extracted with ethyl acetate. The organic layer was washed with saturated brine, dried over anhydrous magnesium sulfate and concentrated under reduced pressure. The residue was purified by silica gel column chromatography (chloroform:acetone=30:1) to give 1-chloro-7-nitroisoquinoline (540 mg, 14%).

Step 5

To a suspension of 1-chloro-7-nitroisoquinoline (670 mg, 3.21 mmol) obtained in Preparation Example 1-5, Step 4 in methanol (100 ml) was added a 1M solution (6.5 ml, 6.5 mmol) of sodium methoxide. The mixture was refluxed under heating for 3 hr and concentrated under reduced pressure. The residue was dissolved in ethyl acetate, washed with saturated brine, dried over anhydrous magnesium sulfate and concentrated under reduced pressure. The residue was purified by silica gel column chromatography (chloroform:acetone=30:1) to give 1-methoxy-7-nitroisoquinoline (530 mg, 81%).

Step 6

A mixture of 1-methoxy-7-nitroisoquinoline (530 mg, 2.60 mmol) obtained in Preparation Example 1-5, Step 5 and ammonium acetate (3 g, 39.0 mmol) was stirred under heating at 135° C. for 4 hr. The reaction mixture was added to aqueous sodium hydrogencarbonate solution and extracted with chloroform. The organic layer was washed with saturated brine, dried over anhydrous magnesium sulfate and concentrated under reduced pressure. The residue was purified by silica gel column chromatography (hexane:ethyl acetate=2:3) to give 1-amino-7-nitroisoquinoline (246 mg, 50%).

Step 7

A mixture of 1-amino-7-nitroisoquinoline (246 mg, 1.3 mmol) obtained in Preparation Example 1-5, Step 6 and 5% palladium carbon (100 mg) in methanol (100 ml) was stirred at room temperature and normal pressure under a hydrogen atmosphere for 8 hr. The reaction mixture was filtered through celite by suction and the filtrate was concentrated under reduced pressure to give the title compound (203 mg, 99%).

Preparation Example 1-6

Synthesis of 7,9-diamino-1,2,3,4-tetrahydroacridine

Step 1

To a mixture of 5-nitroanthranilonitrile (1.63 g, 10 mmol) and cyclohexanone (10.3 ml, 100 mmol) was added zinc chloride (1.36 g, 10 mmol) and the mixture was refluxed under heating for 20 min. The reaction mixture was cooled to room temperature and diluted with ethyl acetate, and the insoluble matter was filtered off. The filtrate was concentrated under reduced pressure and chloroform was added to the obtained brown oil. The resulting yellow precipitate was collected by filtration and dried under reduced pressure at 80° C. This solid (1.56 g) was diluted with ethyl acetate and 1N aqueous sodium hydroxide solution, and ether was added. The insoluble matter was collected by filtration and dried under reduced pressure at 80° C. to give 9-amino-7-nitro-1,2,3,4-tetrahydroacridine (810 mg, 33%) as a yellow solid.

Step 2

9-Amino-7-nitro-1,2,3,4-tetrahydroacridine (773 mg, 3.18 mmol) obtained in Preparation Example 1-6, Step 1 was dissolved in a mixed solvent of tetrahydrofuran (5 ml) and ethanol (5 ml) and 5% palladium carbon (500 mg) was added, which was followed by hydrogenation at room temperature and under normal pressure. After 7 hr, the reaction mixture was passed through celite and the filtrate was concentrated to give the title compound (665 mg, 98%) as a yellow oil.

Preparation Example 2-1

Synthesis of 2-[(4-ethylphenoxy)methyl]benzoic acid

Step 1

To a solution of methyl o-toluate (15.0 g, 0.1 mol) in carbon tetrachloride (200 ml) were added N-bromosuccinimide (18.7 g, 0.1 mol) and benzoyl peroxide (catalytic amount) and the mixture was refluxed under heating for 2 hr. The reaction mixture was cooled to room temperature and the resulting precipitate was filtered off. The filtrate was concentrated under reduced pressure to give methyl α-bromo-o-toluate (yellow oil). The obtained oil was used in the next reaction without purification.

Step 2

To a solution of methyl α-bromo-o-toluate (2.29 g, 10 mmol) obtained in Preparation Example 2-1, Step 1 and 4-ethylphenol (1.28 g, 10.5 mmol) in dimethylformamide (50 ml) was added potassium carbonate (4.15 g, 30 mmol) and the mixture was stirred under heating at 100° C. for 1 hr. The reaction mixture was added to ethyl acetate (100 ml) and washed with water and saturated brine. The organic layer was dried over sodium sulfate and the solvent was evaporated under reduced pressure. The crude product was purified by silica gel column chromatography (hexane:ethyl acetate=100:5) to give methyl 2-[(4-ethylphenoxy)methyl] benzoate (1.96 g, 73%).

Step 3

To a solution of methyl 2-[(4-ethylphenoxy)methyl] benzoate (1.96 g, 7.3 mmol) obtained in Preparation Example 2-1, Step 2 in ethanol (20 ml) was added 2N aqueous potassium hydroxide solution (11 ml, 21.8 mmol) and the mixture was stirred under reflux with heating for 2 hr. To the reaction mixture were added water (70 ml) and 6N hydrochloric acid (5 ml) and the resulting precipitate was collected by filtration and washed with water. The obtained solid was dried under reduced pressure to give the title compound (1.75 g, 94%, white crystals).

Preparation Example 2-2

Synthesis of 2-chloro-4-ethylphenol

A solution of 4-ethylphenol (25.4 g, 0.21 mol) and sulfuryl chloride (18.5 ml, 0.23 mol) in carbon tetrachloride (40 ml) was stirred under heating at 70° C. for 3 hr. The reaction mixture was diluted with chloroform and washed with water. The organic layer was dried over magnesium sulfate and the solvent was evaporated under reduced pressure. The residue was purified by silica gel column chromatography (hexane:ethyl acetate=9:1) to give 2-chloro-4-ethylphenol (25.1 g, 77%).

Preparation Example 2-3

Synthesis of 4-methylsulfonylphenol

Step 1

To a solution of anisole (3.3 ml, 30 mmol) in tetrachloroethylene (30 ml) was added methanesulfonic anhydride (5.75 g, 33 mmol) and the mixture was stirred under heating at 145° C. for 18 hr. Water was added to the reaction mixture and the mixture was extracted with diethyl ether. The organic layer was washed with saturated brine and dried over magnesium sulfate, and the solvent was evaporated under reduced pressure. The residue was purified by silica gel column chromatography (hexane:ethyl acetate=1:1) and the obtained crystals were recrystallized twice from hexane-ethyl acetate to give 4-methylsulfonylanisole (505 mg, 9%, colorless crystals).

Step 2

To 4-methylsulfonylanisole (505 mg, 2.7 mmol) obtained in Preparation Example 2-3, Step 1 was added 48% aqueous hydrogen bromide (3 ml), and the mixture was refluxed under heating for 10 hr. Water was added to the reaction mixture and the mixture was extracted with chloroform. The organic layer was dried over magnesium sulfate and the solvent was evaporated under reduced pressure to give the title compound (256 mg, 55%, colorless crystals). The obtained compound was used in the next reaction without purification.

Preparation Example 2-4

Synthesis of methyl 2-[(5-benzofuranyloxy)methyl] benzoate and methyl 2-[(2,3-dihydrobenzofuran-5-yloxy)methyl]benzoate Step 1

To a solution of 4-(benzyloxy)phenol (10.01 g, 50 mmol) and bromoacetaldehyde diethyl acetal (7.52 ml, 50 mmol) in dimethylformamide (100 ml) was added potassium carbonate (10.37 g, 75 mmol) and the mixture was heated at 170° C. After 2.5 hr, the reaction mixture was cooled to room temperature. The mixture was diluted with water and ethyl acetate, and aqueous layer was removed. The organic layer was washed with saturated aqueous sodium hydrogencarbonate solution and saturated brine, dried over sodium sulfate and concentrated under reduced pressure. The residue was purified by silica gel column chromatography (hexane:ethyl acetate=9:1) to give 2-[4-(benzyloxy) phenoxy]acetaldehyde diethyl acetal (11.902 g, 75%, palebrown oil).

Step 2

2-[4-(Benzyloxy)phenoxy]acetaldehyde diethyl acetal (3.16 g, 10 mmol) obtained in Preparation Example 2-4, Step 1 and polyphosphoric acid (3.16 g) were heated in toluene (30 ml) at 100° C. After 40 min, the mixture was cooled to room temperature. The reaction mixture was diluted with ether and supernatant was separated by decantation. The supernatant was concentrated under reduced pressure, and the residue was purified by silica gel column chromatography (hexane:ethyl acetate=20:1) to give 5-(benzyloxy)benzofuran (1.032 g, 46%, pale-yellow oil).

Step 3

5-(Benzyloxy)benzofuran (1.02 g, 4.55 mmol) obtained in Preparation Example 2-4, Step 2 was dissolved in a mixed solvent of ethanol (5 ml) and ethyl acetate (5 ml) and 5% palladium carbon (500 mg) was added, which was followed by hydrogenation at room temperature under normal pressure. After 2 hr, the reaction mixture was passed through celite and the filtrate was concentrated under reduced pressure. The residue was dissolved in dimethylformamide (20 ml) and methyl α-bromo-o-toluate (1.042 g, 4.55 mmol) and potassium carbonate (1.26 g, 9.10 mmol) were added. The mixture was heated at 100° C. for 1.25 hr and cooled to room temperature. The reaction mixture was diluted with water and ethyl acetate to separate the layers. The organic layer was washed with saturated aqueous sodium hydrogencarbonate solution and saturated brine, dried over sodium sulfate and concentrated under reduced pressure. The residue was purified by silica gel column chromatography (hexane:ethyl acetate=9:1) to give methyl 2-[(5-benzofuranyloxy)methyl]benzoate (352 mg, 27%, white crystals) and methyl 2-[(2,3-dihydrobenzofuran-5-yloxy)methyl]benzoate (220 mg, 17%, pale-yellow oil).

Example 1

Synthesis of N-(4-amino-2-methyl-6-quinolyl)-2-[(4-ethylphenoxy)methyl]-benzamide hydrochloride To a solution of 2-[(4-ethylphenoxy)methyl]benzoic acid (1.13 g, 4.4 mmol) obtained in Preparation Example 2-1 in chloroform (20 ml) was added oxalyl chloride (0.6 ml, 6.8 mmol) and the mixture was stirred at room temperature for 1 hr. Then the reaction mixture was concentrated under reduced pressure. To the obtained acid chloride were added pyridine (20 ml) and 4,6-diamino-2-methylquinoline (623 mg, 4 mmol) obtained in Preparation Example 1-1 and the mixture was stirred at room temperature for 10 hr. To the reaction mixture was added an aqueous sodium hydrogencarbonate solution and the mixture was extracted with ethyl acetate. The organic layer was washed with water and saturated brine and dried over sodium sulfate, and the solvent was evaporated. The obtained crude product was dissolved in ethanol and treated with active charcoal, and the solvent was evaporated. The obtained residue was dissolved in ethyl acetate and 1N hydrochloric acid-ether solution was added. The resulting precipitate was collected by filtration. The obtained solid was heated and dried under reduced pressure to give the title compound (1.06 g, 59%, pale-yellow crystals).

Elemental analysis for $C_{26}H_{25}N_3O_2 \cdot HCl$ Calculated; C, 69.71%; H, 5.85%; N, 9.38%. Found; C, 69.77%; H, 5.78%; N, 9.41%.

Melting point: 235° C.

Example 131

Synthesis of N-(4-amino-2-hydroxymethyl-6-quinolyl)-2-[(4-methylphenoxy)methyl]benzamide hydrochloride Step 1

A solution of 4-nitroaniline (6.91 g, 50 mmol) and dimethyl acetylenedicarboxylate (7.82 g, 55 mmol) in methanol (100 ml) was refluxed under heating for 24.5 hr. The reaction vessel was cooled to room temperature and allowed to stand for a day. The resulting crystals were collected by filtration to give dimethyl 2-[(4-nitrophenyl)amino]-2-butenedioate (6.43 g, 46%, yellow crystals).

Step 2

To Dowtherm A (trademark, 30 ml) refluxed under heating was added dimethyl 2-[(4-nitrophenyl)amino]-2-butenedioate (6.32 g, 22.6 mmol) obtained in Example 131, Step 1 over 5 min by small portions. The mixture was refluxed under heating for 25 min and the reaction mixture was cooled to room temperature. The reaction mixture was diluted with ether and the resulting precipitate was filtrated. The obtained crude crystals were suspended in methanol and collected by filtration to give methyl 1,4-dihydro-6-nitro-4-oxo-2-quinolinecarboxylate (4.75 g, 85%, dark brown crystals).

Step 3

To a suspension of methyl 1,4-dihydro-6-nitro-4-oxo-2-quinolinecarboxylate (3.72 g, 15 mmol) obtained in Example 131, Step 2 in acetonitrile (50 ml) was added chlorosulfonyl isocyanate (1.30 ml, 15 mol) and the mixture was refluxed under heating for 1 hr. The reaction mixture was cooled to room temperature and methanol was added, which was followed by concentration under reduced pressure. To the residue was added 2 mol/l aqueous sodium carbonate solution to allow suspending and the insoluble matter was collected by filtration. The insoluble matter was dried under reduced pressure at 80° C. to give methyl 4-amino-6-nitro-2-quinolinecarboxylate as crude brown crystals (3.23 g). This compound was used in the next reaction without purification.

Step 4

A suspension of crude crystals (494 mg) of methyl 4-amino-6-nitro-2-quinolinecarboxylate obtained Example 131, Step 3 and 5% palladium carbon (500 mg) in ethanol (10 ml) was hydrogenated at room temperature under normal pressure. After 2.5 hr, the reaction mixture was passed through celite. The filtrate was concentrated under reduced pressure to give a crude product of methyl 4,6-diamino-2-quinolinecarboxylate (275 mg, yellow foam-like solid). This compound was used in the next reaction without purification.

Step 5

The crude product (270 mg) of methyl 4,6-diamino-2-quinolinecarboxylate obtained in Example 131, Step 4 and 2-[(4-methylphenoxy)methyl]benzoic acid (363 mg, 1.5 mmol) obtained in the same manner as in Preparation Example 2-1 were condensed to amide in the same manner as in Example 1 to give N-(4-amino-2-methoxycarbonyl-6-quinolyl)-2-[(4-methylphenoxy)methyl]benzamide (175 mg, 17% from methyl 1,4-dihydro-6-nitro-4-oxo-2-quinolinecarboxylate) as a yellow solid.

Step 6

To a solution of N-(4-amino-2-methoxycarbonyl-6-quinolyl)-2-[(4-methylphenoxy)methyl]benzamide (170 mg, 0.385 mmol) obtained in Example 131, Step 5 in tetrahydrofuran (10 ml) was added, by small portions, lithium tetrahydroborate (42 mg, 1.927 mmol) under ice-cooling in an argon stream. After 10 min, the mixture was warmed to room temperature and the mixture was stirred for 2 hr. The reaction mire was diluted with saturated brine and ethyl acetate to separate the layers. The organic layer was washed with saturated brine, dried over anhydrous sodium sulfate and concentrated under reduced pressure. The obtained yellow residue was dissolved in ethyl acetate and 4N hydrochloric acid-dioxane solution (0.5 ml) was added to precipitate hydrochloride. This salt was collected by filtration and dried under reduced pressure at 80° C. to give the title compound (116 mg, 67%, pale-yellow crystals).

An amino-substituted compound obtained in the same manner as in Preparation Examples 1-1 to 1-6 or a commercially available amino-substituted compound and carboxylic acid derivative obtained in the same manner as in Preparation Examples 2-1 to 24 or a commercially available carboxylic acid derivative were treated in the same manner as in Example 1 or 131 to give the compounds of Example 2 to Example 130 and Example 132. The property values are shown in Table 1 to Table 44.

Example 133

Synthesis of N-(4-amino-2-methyl-6-quinolyl)-2-[(4-ethylphenoxy)methyl]-benzamide hydrochloride monohydrate To crude crystals of N-(4-amino-2-methyl-6-quinolyl)-2-[(4-ethyl-phenoxy)methyl]benzamide hydrochloride (24.0 g, 53.7 mmol) obtained in the same manner as in Example 1 was added ethanol (120 ml) and the mixture was heated to 55–60° C. for dissolution. This solution was filtrated and to the filtrate was dropwise added water (120 ml) with stirring under heating at 55–60° C. This reaction mixture was cooled to room temperature and the resulting precipitate was filtrated. The obtained solid was dried at 1 mmHg and 60° C. for 3 days to give the title compound (22.6 g, 94%, colorless crystals).

Elemental analysis for $CH_{26}H_{25}N_3O_2 \cdot HCl \cdot H_2O$ Calculated; C, 67.02%; H, 6.06%; N, 9.02%. Found; C, 66.64%; H, 6.06%; N, 8.99%.

Melting point: 130° C.

TABLE 1

| Exp. No. | Structural formula/character (solvent) | m.p. | 1H NMR (δ) ppm | MS |
|---|---|---|---|---|
| 1 | 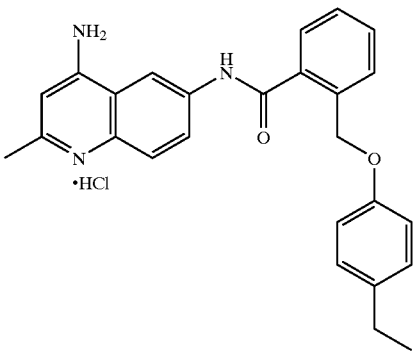<br>Colorless crystals | 235° C. | DMSO-d6, 300 MHz<br>1.10(3H, t, J = 7.7 Hz)<br>2.48(2H, q, J = 7.7 Hz)<br>2.59(3H, s)<br>5.30(2H, s)<br>6.61(1H, s)<br>6.84(2H, d, J = 8.6 Hz)<br>7.05(2H, d, J = 8.6 Hz)<br>7.48–7.69(4H, m)<br>7.94(2H, s)<br>8.66(2H, br.s)<br>8.74(1H, s)<br>10.86(1H, s)<br>13.93(1H, br.s) | FAB-<br>447 [M–H+]<br>(3) |
| 2 | 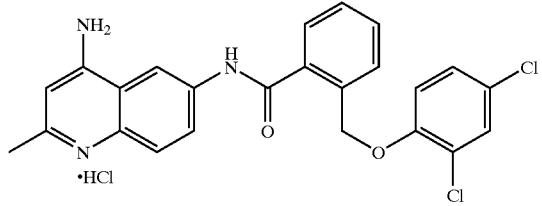 | 262° C. | DMSO-d6, 300 MHz | |
| 3 | 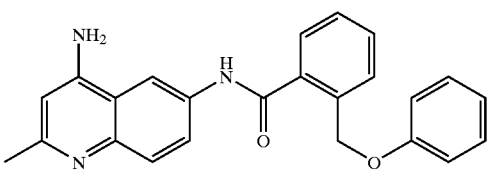<br>Colorless crystals | 245~<br>246° C. | DMSO-d6, 300 MHz<br>2.59(3H, s)<br>5.33(2H, s)<br>6.60(1H, s)<br>6.87–6.95(3H, m)<br>7.21–7.26(2H, m)<br>7.51–7.70(4H, m)<br>7.93(2H, s)<br>8.66(2H, br.s)<br>8.75(1H, s) | FAB-<br>418 [M–H]-<br>(83)<br>367 (100) |

TABLE 2
| Exp. No. | Structural formula/character (solvent) | m.p. | 1H NMR (δ) ppm | MS |
|---|---|---|---|---|
| 4 | 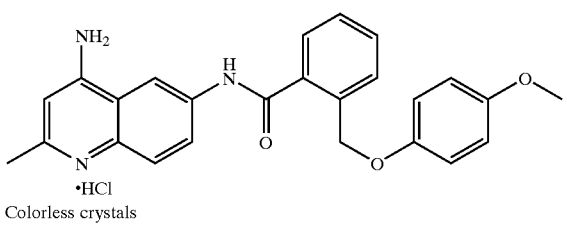<br>•HCl<br>Colorless crystals | 276° C. | DMSO-d6, 300 MHz<br>2.59(3H, s)<br>3.65(3H, s)<br>5.27(2H, s)<br>6.60(1H, s)<br>6.77–6.89(4H, m)<br>7.48–7.68(4H, m)<br>7.88–7.96(2H, m)<br>8.70(2H, br.s)<br>8.74(1H, s)<br>10.85(1H, s)<br>13.78(1H, s) | FAB–<br>448 [M–H]-<br>(65)<br>367 (100) |
| 5 | 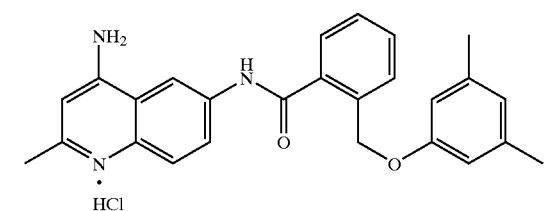<br>•HCl | 265° C. | DMSO-d6, 300 MHz | |
| 6 | 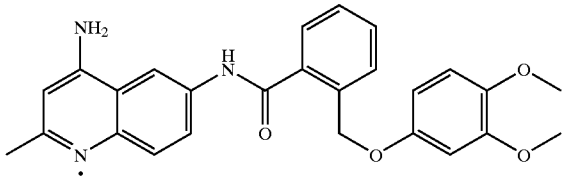<br>•HCl | 270° C. | DMSO-d6, 300 MHz | |
TABLE 3
| Exp. No. | Structural formula/character (solvent) | m.p. | 1H NMR (δ) ppm | MS |
|---|---|---|---|---|
| 7 | 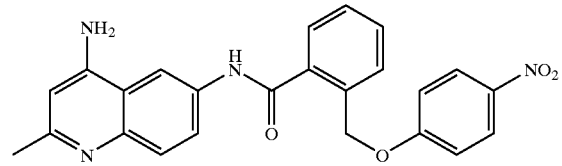 | 148° C. | DMSO-d6, 300 MHz | |
| 8 | 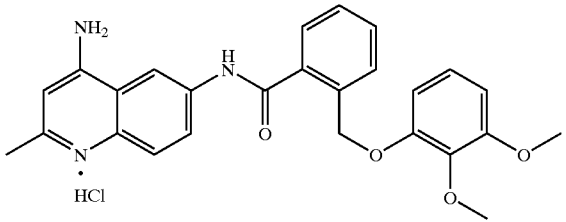<br>•HCl | 196° C. | DMSO-d6, 300 MHz | |

TABLE 3-continued

| Exp. No. | Structural formula/character (solvent) | m.p. | 1H NMR (δ) ppm | MS |
|---|---|---|---|---|
| 9 | (4-amino-2-methylquinolin-6-yl) N-benzamide with 2-((3-methylphenoxy)methyl) substituent | | DMSO-d6, 300 MHz<br>2.20(3H, s)<br>2.40(3H, s)<br>5.31(2H, s)<br>6.45(3H, s)<br>6.70–6.76(3H, m)<br>7.11(1H, t, J = 7.2 Hz)<br>7.47–7.57(4H, m)<br>7.62–7.64(2H, m)<br>8.39(1H, s)<br>10.51(1H, s) | FAB+<br>398 [M+H+]<br>(100) |

TABLE 4

| Exp. No. | Structural formula/character (solvent) | m.p. | 1H NMR (δ) ppm | MS |
|---|---|---|---|---|
| 10 | (4-amino-2-methylquinolin-6-yl) N-benzamide with 2-((3,5-dimethoxyphenoxy)methyl) substituent ·HCl<br>Colorless crystals | | DMSO-d6, 300 MHz<br>2.59(3H, s)<br>3.62(6H, s)<br>5.29(2H, s)<br>6.04–6.08(3H, m)<br>6.60(1H, s)<br>7.49–7.69(4H, m)<br>7.89–7.97(2H, m)<br>8.65(2H, br.s)<br>8.76(1H, d, J = 1.5 Hz)<br>10.85(1H, s)<br>13.74(1H, br.s) | FAB−<br>479 [M−H+]<br>(2) |
| 11 | (4-amino-2-methylquinolin-6-yl) N-benzamide with 2-((4-chlorophenoxy)methyl) substituent ·HCl<br>Colorless crystals | 245° C. | DMSO-d6, 300 MHz<br>2.59(3H, s)<br>5.33(2H, s)<br>6.59(3H, s)<br>6.95(2H, d, J = 8.9 Hz)<br>7.27(2H, d, J = 8.9 Hz)<br>7.49–7.70(4H, m)<br>7.85–7.95(2H, m)<br>8.67(2H, br.s)<br>8.73(1H, s) | FAB−<br>454<br>[M−H]−<br>(50)<br>453 (27)<br>452 (78)<br>416 (100) |
| 12 | (4-amino-2-methylquinolin-6-yl) N-benzamide with 2-((4-acetylphenoxy)methyl) substituent ·HCl<br>Pale-yellow crystals | 270° C. | DMSO-d6, 300 MHz<br>2.47(3H, s)<br>2.58(3H, s)<br>5.44(2H, s)<br>6.59(1H, s)<br>7.03(2H, d, J = 8.9 Hz)<br>7.50–7.71(4H, m)<br>7.81–7.94(4H, m)<br>8.65(2H, br.s)<br>8.72(1H, s)<br>10.88(1H, s)<br>13.66(1H, s) | FAB−<br>460 [M−H]−<br>(18)<br>459 (100) |

TABLE 5

| Exp. No. | Structural formula/character (solvent) | m.p. | 1H NMR (δ) ppm | MS |
|---|---|---|---|---|
| 13 | 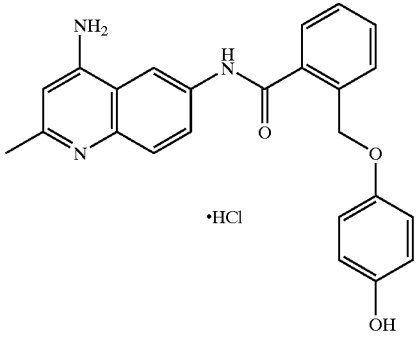<br>Colorless crystals | 183.0~184.0° C. | DMSO-d6, 300 MHz<br>2.58(3H, s)<br>5.22(2H, s)<br>6.59(1H, s)<br>6.61(2H, d, J = 9.6 Hz)<br>6.76(2H, d, J = 9.6 Hz)<br>7.50–7.65(4H, m)<br>7.89–7.99(2H, m)<br>8.59(2H, br.s)<br>8.74(1H, s)<br>8.94(1H, s)<br>10.83(1H, s)<br>13.78(1H, br.s) | |
| 14 | 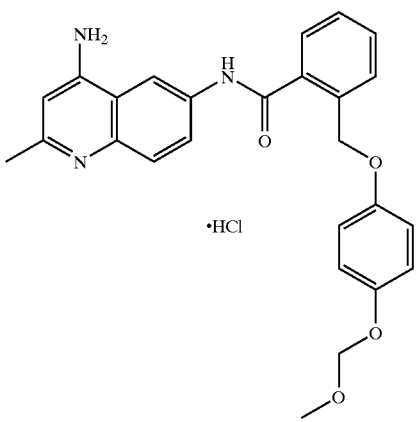<br>Colorless crystals | 210.0~212.0° C. | DMSO-d6, 300 MHz<br>2.59(3H, s)<br>5.05(2H, s)<br>5.28(2H, s)<br>6.60(1H, s)<br>6.88(4H, s)<br>7.50–7.69(4H, m)<br>7.93(2H, s)<br>8.61(2H, s)<br>8.73(1H, s)<br>10.86(1H, s)<br>13.91(1H, br.s) | FAB–<br>479 [M–H+]<br>(3) |
| 15 | 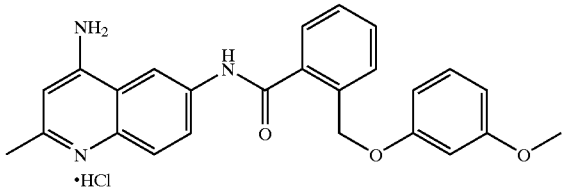 | 224° C. | DMSO-d6, 300 MHz | |

TABLE 6

| Exp. No. | Structural formula/character (solvent) | m.p. | 1H NMR (δ) ppm | MS |
|---|---|---|---|---|
| 16 | 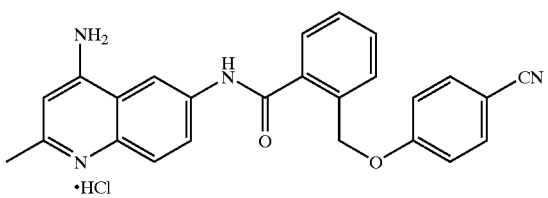 | 286° C. | DMSO-d6, 300 MHz | |

TABLE 6-continued

| Exp. No. | Structural formula/character (solvent) | m.p. | 1H NMR (δ) ppm | MS |
|---|---|---|---|---|
| 17 | 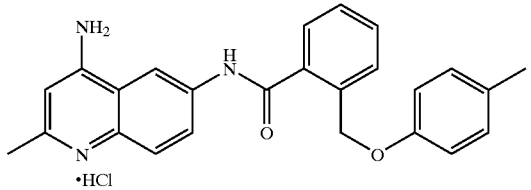<br>·HCl<br>Pale-yellow crystals | 255° C. | DMSO-d6, 300 MHz<br>2.18(3H, s)<br>2.59(3H, s)<br>5.29(2H, s)<br>6.60(1H, s)<br>6.82(2H, d, J = 8.4 Hz)<br>7.02(2H, d, J = 8.4 Hz)<br>7.48–7.88(6H, m)<br>8.66(2H, br.s)<br>8.74(1H, s)<br>10.85(1H, s)<br>13.81(1H, s) | FAB–<br>432 [M–H]–<br>(8)<br>107 (100) |
| 18 | 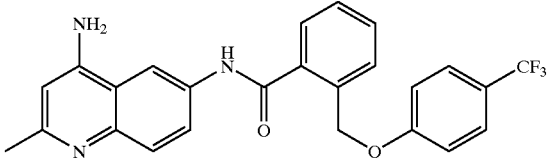<br>·HCl<br>Pale-yellow crystals | 220° C. | DMSO-d6, 300 MHz<br>2.60(3H, s)<br>5.44(2H, s)<br>6.61(1H, s)<br>7.13(2H, d, J = 8.7 Hz)<br>7.53–7.72(6H, m)<br>7.95(2H, s)<br>8.69(2H, br.s)<br>8.72(1H, s) | FAB–<br>486 [M–H]–<br>(7)<br>161 (100) |

TABLE 7

| Exp. No. | Structural formula/character (solvent) | m.p. | 1H NMR (δ) ppm | MS |
|---|---|---|---|---|
| 19 | 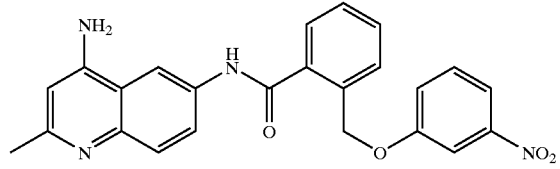<br>·HCl<br>Pale-yellow crystals | 245° C. | DMSO-d6, 300 MHz<br>2.59(3H, s)<br>5.48(2H, s)<br>6.59(1H, s)<br>7.44–7.77(8H, m)<br>7.84–7.93(2H, m)<br>8.65(2H, br.s)<br>8.73(1H, s) | |
| 20 | 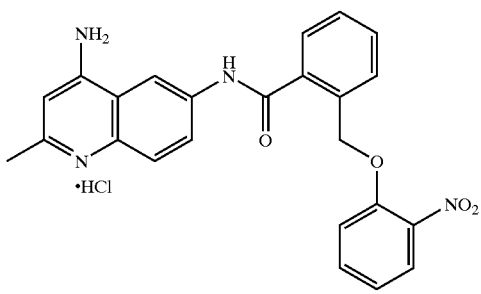<br>·HCl<br>Colorless crystals | 200.0~<br>203.0° C. | DMSO-d6, 300 MHz<br>2.60(3H, s)<br>5.55(2H, s)<br>6.62(1H, s)<br>7.10(1H, t, J = 8.2 Hz)<br>7.42(1H, d, J = 8.2 Hz)<br>7.55–7.86(6H, m)<br>7.95(2H, s)<br>8.73(2H, br.s)<br>8.74(1H, s)<br>10.91(1H, s)<br>13.99(1H, br.s) | FAB–<br>464 [M–H+]<br>(4) |

TABLE 7-continued

| Exp. No. | Structural formula/character (solvent) | m.p. | 1H NMR (δ) ppm | MS |
|---|---|---|---|---|
| 21 | 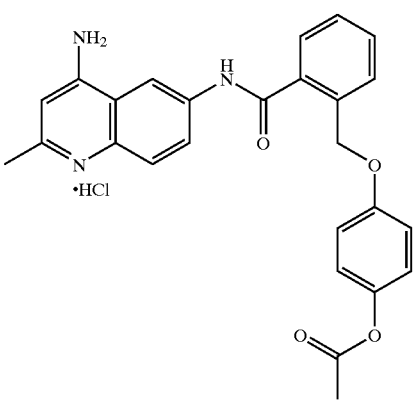 Colorless crystals | 154.0~155.0° C. | DMSO-d6, 300 MHz 2.21(3H, s) 2.59(3H, s) 5.33(2H, s) 6.60(1H, s) 6.93–7.00(4H, m) 7.50–7.70(4H, m) 7.90(1H, d, J = 9.2 Hz) 7.94(1H, d, J = 9.2 Hz) 8.63(2H, br.s) 8.74(1H, s) 10.87(1H, s) 13.85(1H, br.s) | FAB− 477 [M−H+] (1) |

TABLE 8

| Exp. No. | Structural formula/character (solvent) | m.p. | 1H NMR (δ) ppm | MS |
|---|---|---|---|---|
| 22 | 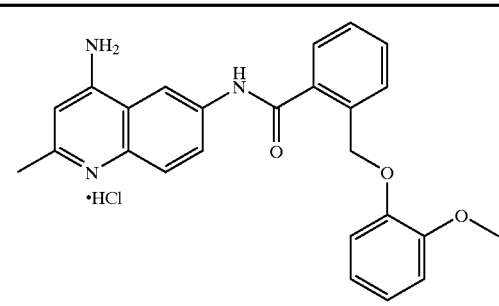 Colorless crystals | 148.0~149.0° C. | DMSO-d6, 300 MHz 2.59(3H, s) 3.65(3H, s) 5.32(2H, s) 6.60(1H, s) 6.82–6.98(4H, m) 7.51–7.58(2H, m) 7.66–7.71(2H, m) 7.95(2H, s) 8.65(2H, br.s) 8.75(1H, s) 10.87(1H, s) 13.80(1H, br.s) | FAB+ 449 [M−H+] (4) |
| 23 | 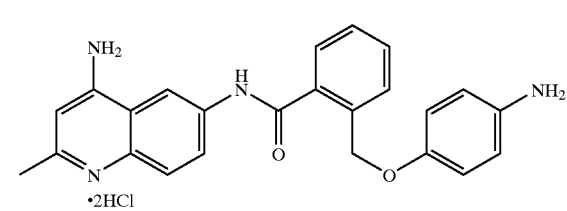 | 237° C. | DMSO-d6, 300 MHz | |
| 24 | 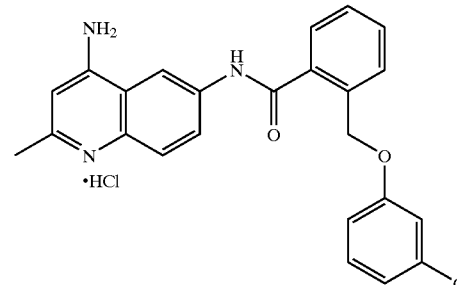 Colorless crystals | 147.0~149.0° C. | DMSO-d6, 300 MHz 2.59(3H, s) 5.36(2H, s) 6.60(1H, s) 6.90–6.99(3H, m) 7.22–7.28(1H, m) 7.50–7.71(4H, m) 7.89–7.92(2H, m) 8.61(2H, br.s) 8.73(1H, s) 10.86(1H, s) 13.85(1H, br.s) | FAB− 455 [M−H+] (5) |

TABLE 9
| Exp. No. | Structural formula/character (solvent) | m.p. | 1H NMR (δ) ppm | MS |
|---|---|---|---|---|
| 25 | 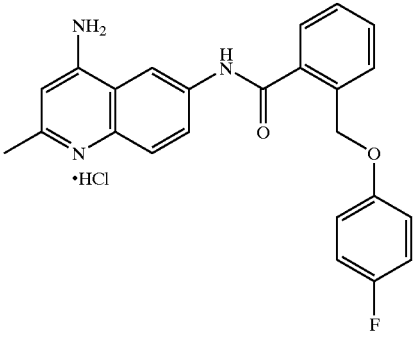<br>Colorless crystals | 146.0~148.0° C. | DMSO-d6, 300 MHz<br>2.59(3H, s)<br>5.31(2H, s)<br>6.60(1H, s)<br>6.93–7.09(4H, m)<br>7.49–7.70(4H, m)<br>7.87–7.95(2H, m)<br>8.61(2H, br.s)<br>8.73(1H, s)<br>10.85(1H, s)<br>13.80(1H, br.s) | FAB–437 [M–H+] (3) |
| 26 | 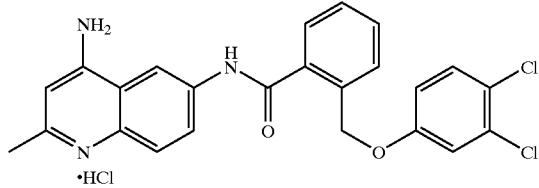 | 223° C. | DMSO-d6, 300 MHz | |
| 27 | 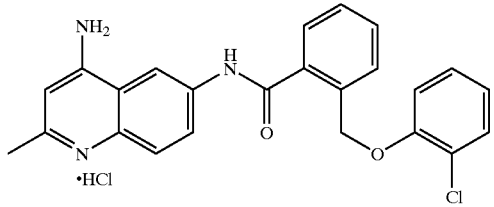 | 165° C. | DMSO-d6, 300 MHz | |
TABLE 10
| Exp. No. | Structural formula/character (solvent) | m.p. | 1H NMR (δ) ppm | MS |
|---|---|---|---|---|
| 28 | 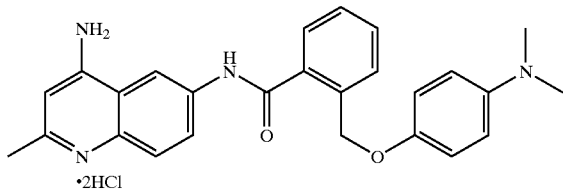 | 233° C. | DMSO-d6, 300 MHz | |
| 29 | 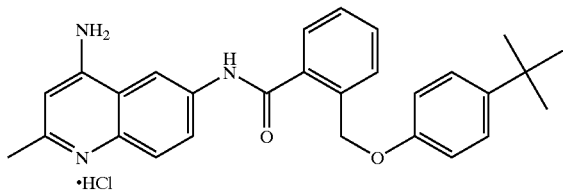 | 268° C. | DMSO-d6, 300 MHz | |

TABLE 10-continued
| Exp. No. | Structural formula/character (solvent) | m.p. | 1H NMR (δ) ppm | MS |
|---|---|---|---|---|
| 30 | 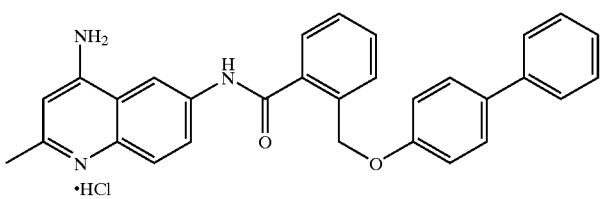 | 268° C. | DMSO-d6, 300 MHz | |
TABLE 11
| Exp. No. | Structural formula/character (solvent) | m.p. | 1H NMR (δ) ppm | MS |
|---|---|---|---|---|
| 31 | 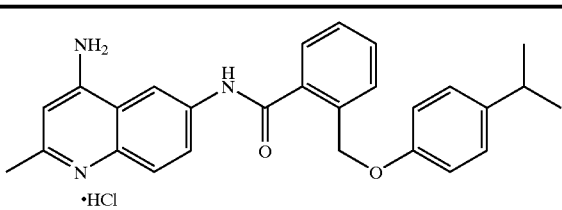 | 256° C. | DMSO-d6, 300 MHz | |
| 32 | 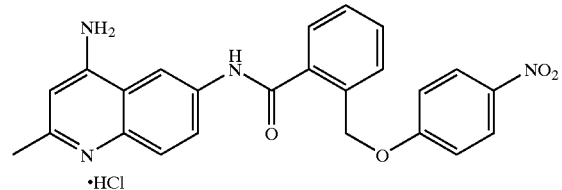 | 238° C. | DMSO-d6, 300 MHz | |
| 33 | 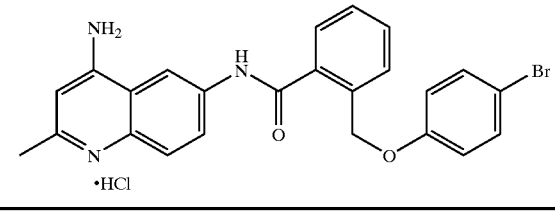 | 252° C. | DMSO-d6, 300 MHz | |

TABLE 12
| Exp. No. | Structural formula/character (solvent) | m.p. | 1H NMR (δ) ppm | MS |
|---|---|---|---|---|
| 34 | 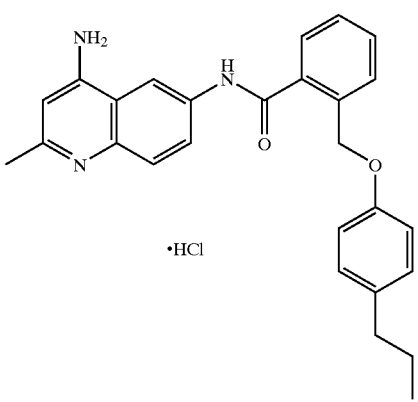<br>Colorless crystals | 140.0~<br>142.0° C. | DMSO-d6, 300 MHz<br>0.83(3H, t, J = 7.4 Hz)<br>1.48(2H, q, J = 7.4 Hz)<br>2.42(2H, t, J = 7.4 Hz)<br>2.60(3H, s)<br>5.30(2H, s)<br>6.61(1H, s)<br>6.84(2H, d, J = 8.5 Hz)<br>7.02(2H, d, J = 8.5 Hz)<br>7.50–7.69(4H, m)<br>7.95(2H, s)<br>8.68(2H, br.s)<br>8.74(1H, s)<br>10.87(1H, s)<br>14.01(1H, br.s) | FAB–<br>461 [M–H+]<br>(6) |
| 35 | 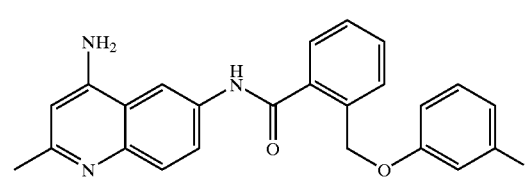 | 255° C. | DMSO-d6, 300 MHz | |
| 36 | 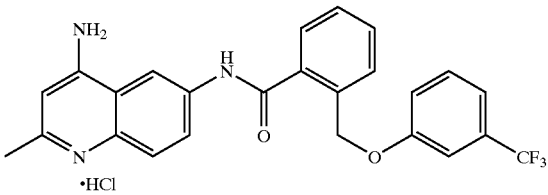 | 253° C. | DMSO-d6, 300 MHz | |
TABLE 13
| Exp. No. | Structural formula/character (solvent) | m.p. | 1H NMR (δ) ppm | MS |
|---|---|---|---|---|
| 37 | 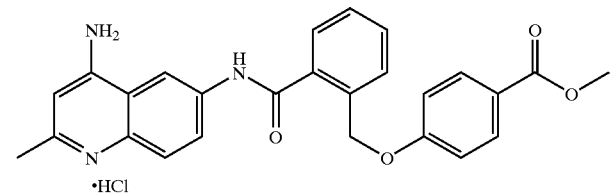 | 262° C. | DMSO-d6, 300 MHz | |

TABLE 13-continued

| Exp. No. | Structural formula/character (solvent) | m.p. | 1H NMR (δ) ppm | MS |
|---|---|---|---|---|
| 38 | Colorless crystals | 148.0~150.0° C. | DMSO-d6<br>2.39(3H, s)<br>5.33(2H, s)<br>6.39(2H, br.s)<br>6.44(1H, s)<br>6.81(2H, d, J = 8.8 Hz)<br>7.49–7.67(8H, m)<br>8.36(1H, s)<br>10.49(1H, s) | FAB+<br>510 [M+H+]<br>(100) |
| 39 | Pale-yellow crystals ·HCl | 207° C. | DMSO-d6, 300 MHz<br>2.59(3H, s)<br>5.53(2H, s)<br>6.60(1H,s)<br>7.52–7.73(4H, m)<br>7.85–7.94(3H, m)<br>8.35(1H, m)<br>8.54(1H, s)<br>8.68(2H, br.s)<br>8.72(1H, s)<br>10.91(1H, s)<br>13.94(1H, s) | FAB–<br>419 [M–H]–<br>(6)<br>367 (100) |

TABLE 14

| Exp. No. | Structural formula/character (solvent) | m.p. | 1H NMR (δ) ppm | MS |
|---|---|---|---|---|
| 40 | ·HCl | 225° C. | DMSO-d6, 300 MHz | |
| 41 | ·HCl | 195° C. | DMSO-d6, 300 MHz | |

TABLE 14-continued

| Exp. No. | Structural formula/character (solvent) | m.p. | 1H NMR (δ) ppm | MS |
|---|---|---|---|---|
| 42 | [Structure: 4-amino-2-methylquinolin-6-yl amide of 2-((4-chloro-3-methylphenoxy)methyl)benzamide · HCl] Colorless crystals | 150.0~ 152.0° C. | DMSO-d6, 300 MHz<br>2.19(3H, s)<br>2.60(3H, s)<br>5.32(2H, s)<br>6.61(1H, s)<br>6.79(1H, dd, J = 2.9, 8.7 Hz)<br>6.92(1H, d, J = 2.9 Hz)<br>7.22(1H, d, J = 8.7 Hz)<br>7.52–7.69(4H, m)<br>7.93(2H, s)<br>8.71(2H, br.s)<br>8.74(1H, s)<br>10.90(1H, s)<br>13.91(1H, s) | |

TABLE 15

| Exp. No. | Structural formula/character (solvent) | m.p. | 1H NMR (δ) ppm | MS |
|---|---|---|---|---|
| 43 | [Structure: 4-amino-2-methylquinolin-6-yl amide of 2-((2-chloro-4-methylphenoxy)methyl)benzamide · HCl] Colorless crystals | 159.0~ 160.0° C. | DMSO-d6<br>2.19(3H, s)<br>2.60(3H, s)<br>5.40(2H, s)<br>6.61(1H, s)<br>7.05(2H, s)<br>7.20(1H, s)<br>7.53–7.61(2H, m)<br>7.69–7.73(2H, m)<br>8.66(2H, br.s)<br>8.75(1H, s)<br>7.95(2H, s)<br>10.89(1H, s)<br>13.98(1H, br.s) | |
| 44 | [Structure: 4-amino-2-methylquinolin-6-yl amide of 2-((4-ethylphenoxy)methyl)benzamide] Colorless crystals | 96.0~ 98.0° C. | DMSO-d6<br>1.11(3H, t, J = 7.6 Hz)<br>2.41(3H, s)<br>2.50(2H, q, J = 7.6 Hz)<br>5.30(2H, s)<br>6.45(1H, s)<br>6.56(2H, br.s)<br>6.86(2H, d, J = 8.6 Hz)<br>7.06(2H, d, J = 8.6 Hz)<br>7.48–7.55(2H, m)<br>7.62–7.67(4H, m)<br>8.41(1H, s)<br>10.5(1H, s) | FAB+<br>411 [M+H+]<br>(100) |

TABLE 15-continued

| Exp. No. | Structural formula/character (solvent) | m.p. | 1H NMR (δ) ppm | MS |
|---|---|---|---|---|
| 45 | Colorless crystals | | DMSO-d6<br>2.21(3H, s)<br>2.40(3H, s)<br>5.32(2H, s)<br>6.44(2H, br.s)<br>6.81(1H, dd, J = 2.7, 8.6 Hz)<br>6.95(1H, d, J = 2.7 Hz)<br>7.24(1H, D, J = 8.6 Hz)<br>7.47–7.67(6H, m)<br>8.38(1H, s)<br>10.5(1H, br.s) | FAB+<br>432 [M]<br>(100)<br>433 [M+1]<br>(41) |

TABLE 16

| Exp. No. | Structural formula/character (solvent) | m.p. | 1H NMR (δ) ppm | MS |
|---|---|---|---|---|
| 46 | ·HCl<br>Pale-yellow crystals | 258° C. | DMSO-d6, 300 MHz<br>2.00(3H, s)<br>2.59(3H, s)<br>4.94(2H, s)<br>5.34(2H, s)<br>6.60(1H, s)<br>6.93(2H, d, J = 8.6 Hz)<br>7.24(2H, d. J = 8.6 Hz)<br>7.49–7.90(2H, m)<br>7.85–7.96(2H, m)<br>8.63(2H, br.s)<br>8.74(1H, s) | FAB–<br>490 [M–H]-<br>(87)<br>454 (100) |
| 47 | ·HCl<br>Pale-brown crystals | 273° C. | DMSO-d6, 300 MHz<br>2.58(3H, s)<br>4.36(2H, d, J = 5.2 Hz)<br>5.02(1H, t, J = 5.2 Hz)<br>5.32(2H, s)<br>6.59(1H, s)<br>6.88(2H, d, J = 8.6 Hz)<br>7.16(2H, d, J = 8.6 Hz)<br>7.49–7.70(4H, m)<br>7.85–7.98(4H, m)<br>8.67(2H, Br.s)<br>8.75(1H, s) | FAB–<br>412 [M–H]-<br>(100) |
| 48 | ·HCl<br>Colorless crystals | 154.0~<br>156.0° C. | DMSO-d6, 300 MHz<br>2.59(3H, s)<br>5.46(2H, s)<br>6.59(1H, s)<br>7.13–7.80(11H, m)<br>7.91–7.95(2H, m)<br>8.67(2H, br.s)<br>8.75(1H, s)<br>10.91(1H, s)14.01(1H, br.s) | FAB–<br>469 [M–H+]<br>(2) |

TABLE 17

| Exp. No. | Structural formula/character (solvent) | m.p. | 1H NMR (δ) ppm | MS |
|---|---|---|---|---|
| 49 | 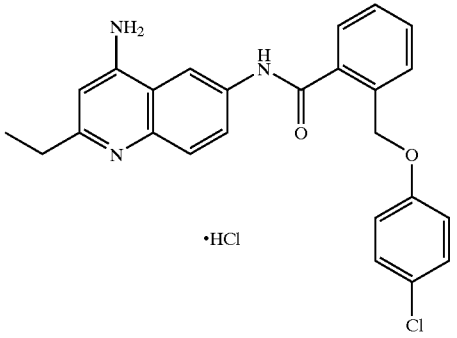<br>Colorless crystals | 247.0~249.0° C. | DMSO-d6<br>1.32(3H, t, J = 7.7 Hz)<br>2.89(2H, q, J = 7.7 Hz)<br>5.34(2H, s)<br>6.66(1H, s)<br>6.96(2H, d, J = 9.2 Hz)<br>7.26(2H, d, J = 8.8 Hz)<br>7.49–7.71(4H, m)<br>7.95(1H, d, J = 8.8 Hz)<br>7.99(1H, d, J = 9.2 Hz)<br>8.72(2H, br.s)<br>8.73(1H, s)<br>10.87(1H, s)13.91(1H, s) | FAB-<br>467 [M–H+]<br>(3) |
| 50 | 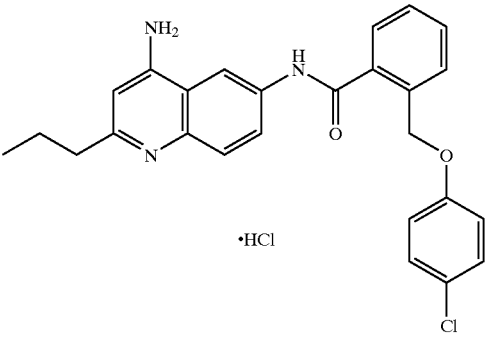<br>Colorless crystals | 232.0~233.0° C. | DMSO-d6<br>0.96(3H, t, J = 7.4 Hz)<br>1.73–1.80(2H, m)<br>2.85(2H, t, J = 7.4 Hz)<br>5.34(2H, s)<br>6.65(1H, s)<br>6.96(2H, d, J = 8.8 Hz)<br>7.26(2H, d, J = 8.8 Hz)<br>7.50–7.71(4H, m)<br>7.94(1H, d, J = 9.2 Hz)<br>8.00(1H, d, J = 9.2 Hz)<br>8.73(2H, br.s)<br>8.74(1H, s)<br>10.87(1H, s)<br>13.93(1H, s) | FAB-<br>481 [M–H+]<br>(3) |
| 51 | 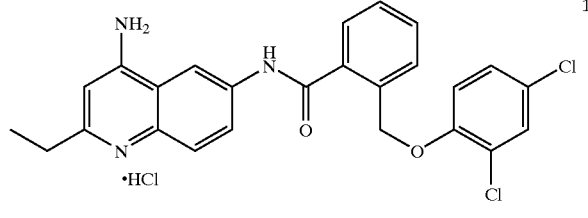<br>Pale-red crystals | 163° C. | DMSO-d6, 300 MHz<br>1.32(3H, t, J = 7.5 Hz)<br>2.88(2H, q, J = 7.5 Hz)<br>5.44(2H, s)<br>6.65(1H, s)<br>7.22(1H, d, J = 8.9 Hz)<br>7.34(1H, dd, J = 8.9, 2.5 Hz)<br>7.51(1H, d, J = 2.5 Hz)<br>7.53–7.75(4H, m)<br>7.90–7.97(2H, m)<br>8.66(2H, br.s)<br>8.74(1H, s)<br>10.89(1H, s)<br>13.68(1H, s) | FAB-<br>502 (25)<br>500 (42)<br>127 (100) |

TABLE 18

| Exp. No. | Structural formula/character (solvent) | m.p. | 1H NMR (δ) ppm | MS |
|---|---|---|---|---|
| 52 | 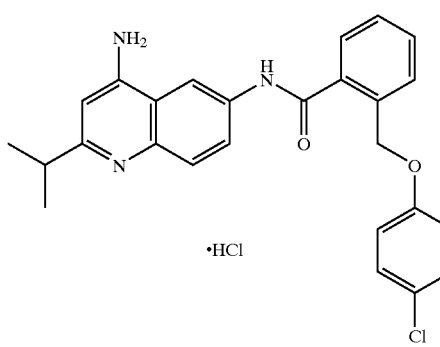<br>Colorless crystals | 162.0~ 164.0° C. | DMSO-d6<br>1.35(6H, d, J = 6.9 Hz)<br>3.22(1H, o, J = 6.9 Hz)<br>5.34(2H, s)<br>6.69(1H, s)<br>6.96(2H, d, J = 9.0 Hz)<br>7.26(2H, d, J = 9.0 Hz)<br>7.52–7.68(4H, m)<br>7.68(1H, d, J = 9.1 Hz)<br>8.04(1H, d, J = 9.1 Hz)<br>8.73(1H, s)<br>8.73(2H, br.s)<br>10.9(1H, s)<br>13.7(1H, br.s) | FAB-<br>482 [M–H+]<br>(28) |
| 53 | 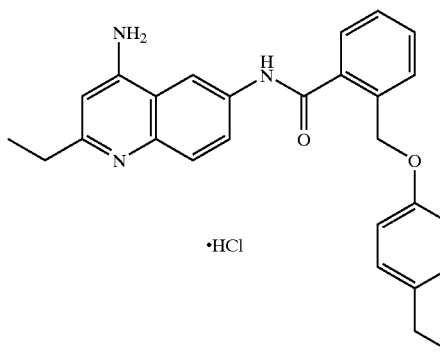<br>Colorless crystals | 160.0~ 161.0° C. | DMSO-d6<br>1.10(3H, t, J = 7.6 Hz)<br>1.32(3H, t, J = 7.6 Hz)<br>2.48(2H, q, J = 7.6 Hz)<br>2.89(2H, q, J = 7.6 Hz)<br>5.30(2H, s)<br>6.66(1H, s)<br>6.84(2H, d, J = 8.6 Hz)<br>7.05(2H, D, J = 8.6HZ)<br>7.51–7.69(4H, m)<br>7.96(2H, s)<br>8.74(2H, br.s)<br>8.75(1H, s)<br>10.9(1H, s)<br>13.8(1H, s) | FAB-<br>461 [M–H+]<br>(13) |
| 54 | 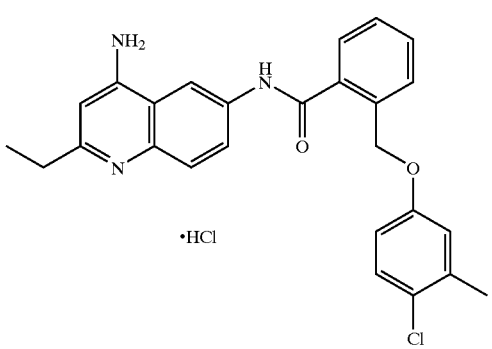<br>Colorless crystals (AcOEt—Et2O) | 150.0~ 152.0° C. | DMSO-d6<br>1.32(3H, t, J = 7.5 Hz)<br>2.19(3H, s)<br>2.89(2H, q, J = 7.5 Hz)<br>5.32(2H, s)<br>6.66(1H, s)<br>6.79(1H, dd, J = 3.0, 8.7 Hz)<br>6.92(1H, d, J = 3.0 Hz)<br>7.22(1H, d, J = 8.7 Hz)<br>7.50–7.70(4H, m)<br>7.91–7.99(2H, m)<br>8.73(2H, br.s)<br>8.74(1H, s)<br>10.86(1H, s)<br>13.85(1H, br.s) | FAB-<br>481 [M–H+]<br>(26) |

TABLE 19

| Exp. No. | Structural formula/character (solvent) | m.p. | 1H NMR (δ) ppm | MS |
|---|---|---|---|---|
| 55 | (4-amino-2-methylquinolin-6-yl) 2-(benzyloxymethyl)benzamide | 83.0~84.0° C. | DMSO-d6, 300 MHz<br>2.41(3H, s)<br>4.53(2H, s)<br>4.78(2H, s)<br>6.46(1H, s)<br>6.49(2H, br.s)<br>7.22–7.30(5H, m)<br>7.45–7.66(6H, m)<br>8.41(1H, s)<br>10.45(1H, s) | 398 [M+H+]<br>(100) |
| 56 | (2-methylquinolin-6-yl) 2-(phenoxymethyl)benzamide ·HCl | | DMSO-d6, 300 MHz<br>2.91(3H, s)<br>5.33(2H, s)<br>6.87–6.92(3H, m)<br>7.18–7.23(2H, m)<br>7.52–7.68(4H, m)<br>7.87(1H, d, J = 8.7Hz)<br>8.18–8.25(2H, m)<br>8.79(1H, s)<br>8.92(1H, d, J = 8.7 Hz)<br>11.05(1H, s) | |
| 57 | (4-amino-2-methylquinolin-6-yl) benzamide | | DMSO-d6, 300 MHz<br>2.40(3H, s)<br>6.43(2H, br.s)<br>6.45(1H, s)<br>7.53–7.75(5H, m)<br>8.00(1H, s)<br>8.03(1H, s)<br>8.38(1H, d, J = 2.1 Hz)<br>10.35(1H, s) | FAB+<br>278 [M+H+]<br>(100) |

TABLE 20

| Exp. No. | Structural formula/character (solvent) | m.p. | 1H NMR (δ) ppm | MS |
|---|---|---|---|---|
| 58 | (4-amino-2-methylquinolin-6-yl) biphenyl-2-carboxamide | | DMSO-d6, 300 MHz<br>2.37(3H, s)<br>6.36(2H, s)<br>6.42(1H, s)<br>7.29–7.61(11H, m)<br>8.25(1H, d, J = 2.0 Hz)<br>10.33(1H, s) | FAB+<br>354 [M+H]+<br>(100) |
| 59 | (4-amino-2-methylquinolin-6-yl) 2-cyanobenzamide<br>Colorless crystals | | DMSO-d6, 300 MHz<br>2.44(3H, s)<br>6.49(1H, s)<br>6.68(2H, br.s)<br>7.56–8.30(7H, m)<br>10.30(1H, s) | FAB+<br>303 [M+H+]<br>(9) |

TABLE 20-continued
| Exp. No. | Structural formula/character (solvent) | m.p. | 1H NMR (δ) ppm | MS |
|---|---|---|---|---|
| 60 | 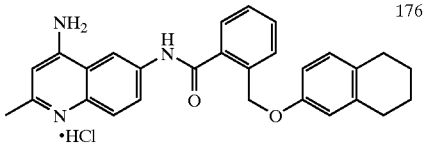 | 176° C. | | |
TABLE 21
| Exp. No. | Structural formula/character (solvent) | m.p. | 1H NMR (δ) ppm | MS |
|---|---|---|---|---|
| 61 | 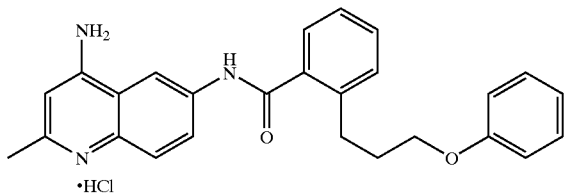<br>Colorless crystals | 232° C. | | |
| 62 | 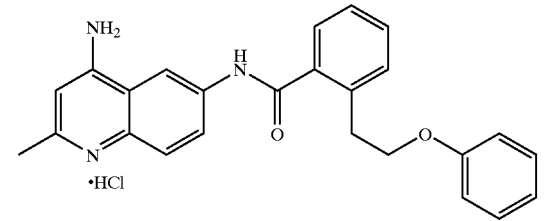<br>Yellow crystals | 208° C. | | |
| 63 | 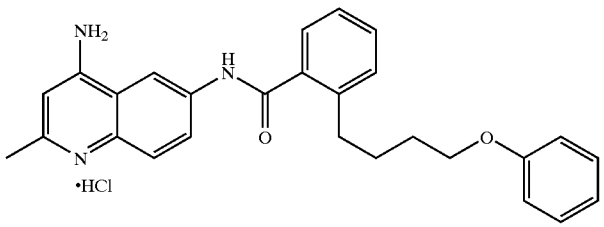<br>Pale-yellow crystals | 212° C. | | |

TABLE 22

| Exp. No. | Structural formula/character (solvent) | m.p. | 1H NMR (δ) ppm | MS |
|---|---|---|---|---|
| 64 | 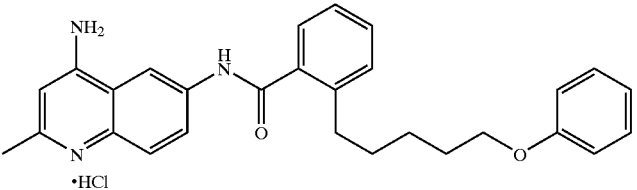<br>Pale-yellow crystals | 253° C. | | |
| 65 | 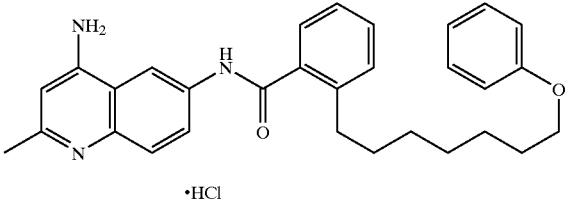<br>Colorless crystals | 223.0~<br>225.0° C. | DMSO-d6<br>1.20–1.38(6H, m)<br>1.50–1.68(4H, m)<br>2.57(3H, s)<br>2.78(2H, t, J=6.5Hz)<br>3.79(2H, t, J=6.5Hz)<br>6.59(1H, s)<br>6.81–6.91(3H, m)<br>7.22–7.51(6H, m)<br>7.88–7.94(2H, m)<br>8.69(2H, br.s)<br>8.79(1H, s)<br>10.78(1 H, s)<br>13.79(1H, br.s) | |
| 66 | 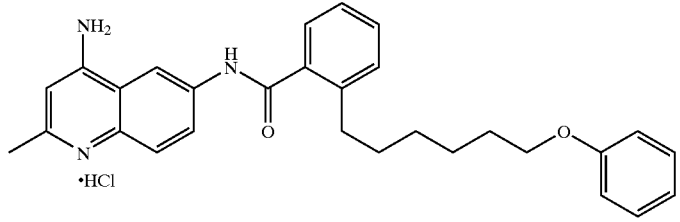<br>Pale-brown crystals | 210° C. | | |

TABLE 23

| Exp. No. | Structural formula/character (solvent) | m.p. | 1H NMR (δ) ppm | MS |
|---|---|---|---|---|
| 67 | 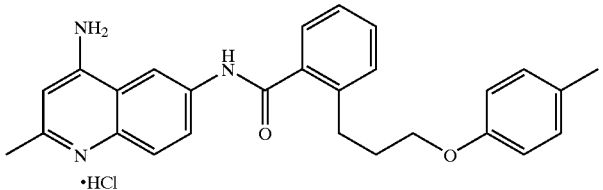 | | DMSO-d6, 300 MHz<br>2.02(2H, m)<br>2.17(3H, s)<br>2.61(3H, s)<br>2.94(3H, t, J=8.2Hz)<br>3.90(3H, t, J=6.4Hz)<br>6.62(1H, s)<br>6.71(2H, d, J=8.6Hz)<br>6.97(2H, d, J=8.6Hz)<br>7.34–7.54(4H, m)<br>7.95(2H, s)<br>8.50–8.90(2H, brs)<br>8.78(1H, s)<br>10.80(1H, s)<br>14.02(1H, s) | |

TABLE 23-continued

| Exp. No. | Structural formula/character (solvent) | m.p. | 1H NMR (δ) ppm | MS |
|---|---|---|---|---|
| 68 |  •HCl | | DMSO-d6, 300 MHz 2.07(2H, s) 2.61(3H, s) 2.97(2H, t, J=8.0Hz) 4.04(2H, t, J=6.1Hz) 6.62(1H, s) 7.07(1H, d, J=8.9Hz) 7.25 7.34–7.53(5H, m) 8.50–8.90(2H, brs) 8.77(1H, s) 10.80(1H, s) 14.00(1H, s) | |
| 69 | 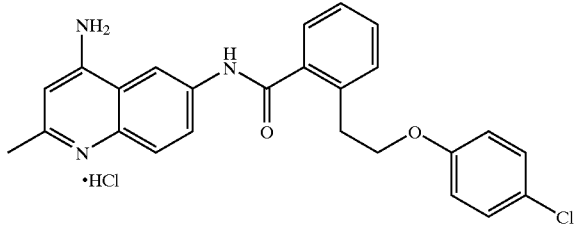 •HCl | | DMSO-d6, 300 MHz 2.60(3H, s) 3.24(2H, t, J=6.8Hz) 4.23(3H, t, J=6.8Hz) 6.62(1H, s) 6.90(2H, d, J=8.9Hz) 7.23(2H, d, J=8.9Hz) 7.39–7.60(4H, m) 7.95(2H, s) 8.50–8.90(2H, brs) 8.80(1H, s) 10.85(1H, s) 13.94(1H, s) | |

TABLE 24

| Exp. No. | Structural formula/character (solvent) | m.p. | 1H NMR (δ) ppm | MS |
|---|---|---|---|---|
| 70 | 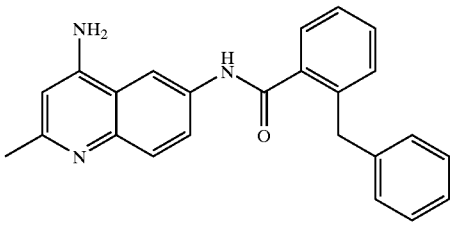 | | DMSO-d6, 300 MHz 2.38(3H, s) 4.18(2H, s) 6.41(2H, s) 6.45(1H, s) 7.14–7.63(11H, m) 8.42(1H, s) 10.44(1H, s) | FAB– 366 [M–H–]– (100) |
| 71 | 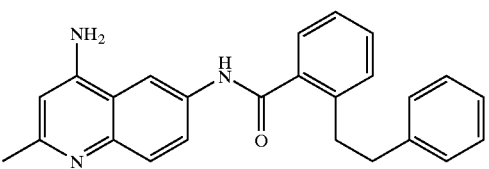 | | DMSO-d6, 300 MHz 2.38(3H, s) 2.88–2.93(2H, m) 3.03–3.09(2H, m) 6.43(2H, s) 6.45(1H, s) 7.14–7.71(11H, m) 8.43(1H, s) 10.46(1H, s) | FAB+ 382 [M+H]+ (100) |
| 72 | 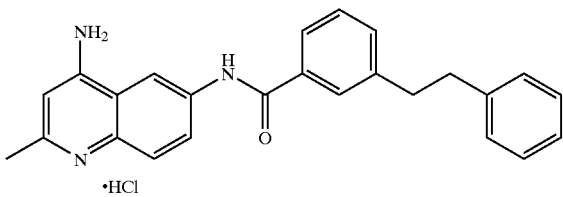 •HCl Colorless crystals | >300° C. | | |

TABLE 25

| Exp. No. | Structural formula/character (solvent) | m.p. | 1H NMR (δ) ppm | MS |
|---|---|---|---|---|
| 73 | 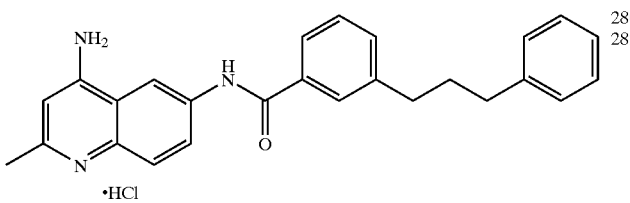<br>Colorless crystals | 280~282.0° C. | | |
| 74 | 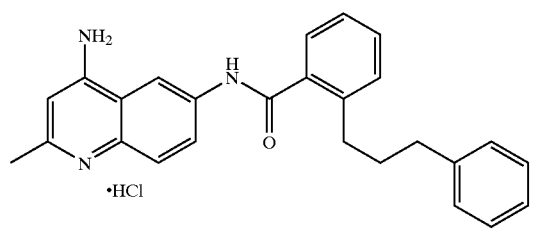<br>Colorless crystals | 252.0~254.0° C. | | |
| 75 | 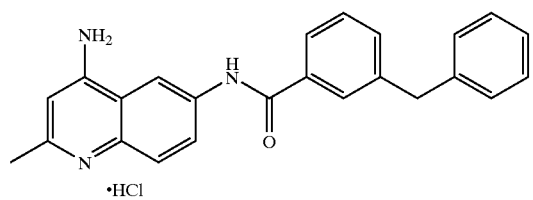<br>Colorless crystals | 306~308° C. | | |

TABLE 26

| Exp. No. | Structural formula/character (solvent) | m.p. | 1H NMR (δ) ppm | MS |
|---|---|---|---|---|
| 76 |  | 184.0~185.0° C. | DMSO-d6, 300MHz<br>2.40(3H, s)<br>4.04(2H, s)<br>6.44(1H, s)<br>6.46(2H, br.s)<br>7.19–7.42(7H, m)<br>7.64(1H, d, J=9.3Hz)<br>7.72(1H, dd, J=2.1, 9.0Hz)<br>7.94(2H, d, J=7.8Hz)<br>8.36(1H, d, J=2.1Hz)<br>10.27(1H, s) | FAB+<br>368 [M+H+]<br>(100) |
| 77 | 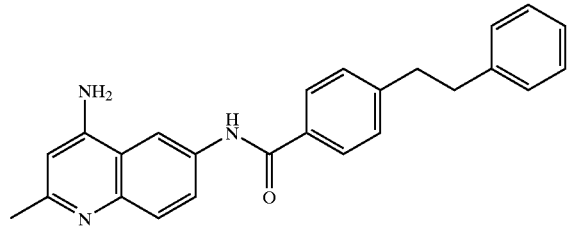 | 183.0~184.0° C. | DMSO-d6, 300MHz<br>2.40(3H, s)<br>2.92–3.01(4H, m)<br>6.43(2H, br.s)<br>6.44(1H, s)<br>7.16–7.38(7H, m)<br>7.65(1H, d, J=8.9Hz)<br>7.73(1H, dd, J=2.1, 8.9Hz)<br>7.94(2H, d, J=8.1Hz)<br>8.37(1H, d, J=2.1Hz)<br>10.28(1H, s) | |

TABLE 26-continued

| Exp. No. | Structural formula/character (solvent) | m.p. | 1H NMR (δ) ppm | MS |
|---|---|---|---|---|
| 78 | | 161.0~162.0° C. | DMSO-d6, 300MHz<br>1.89–1.96(2H, m)<br>2.40(3H, s)<br>2.63(2H, t, J=8.0Hz)<br>2.70(2H, t, J=8.0Hz)<br>6.43(2H, br.s)<br>6.44(1H, s)<br>7.16–7.40(7H, m)<br>7.65(1H, d, J=8.8Hz)<br>7.73(1H, dd, J=2.4, 8.8Hz)<br>7.95(2H, d, J=8.4Hz)<br>8.37(1H, d, J=2.1Hz)<br>10.28(1H, s) | FAB+<br>396<br>[M+H+]<br>(100) |

TABLE 27

| Exp. No. | Structural formula/character (solvent) | m.p. | 1H NMR (δ) ppm | MS |
|---|---|---|---|---|
| 79 | | 109.0~110.0° C. | DMSO-d6, 300MHz<br>2.40(3H, s)<br>6.43(2H, br.s)<br>6.45(1H, s)<br>6.66(1H, d, J=12.3Hz)<br>6.91(1H, d, J=12.3Hz)<br>7.15–7.21(6H, m)<br>7.32(1H, t, J=7.2Hz)<br>7.40(1H, t, J=7.2Hz)<br>7.62–7.65(3H, m)<br>8.42(1H, s)<br>10.44(1H, s) | FAB+<br>380 [M+H+]<br>(100) |
| 80 | | 124.0~125.0° C. | DMSO-d6, 300MHz<br>2.40(3H, s)<br>6.45(2H, s)<br>7.26–7.66(12H, m)<br>7.94(1H, d, J=7.9Hz)<br>8.48(1H, s)<br>10.54(1H, s) | FAB+<br>380 [M+H+]<br>(100) |
| 81 | ·HCl<br>Colorless crystals | 233° C. | | |

TABLE 28

| Exp. No. | Structural formula/character (solvent) | m.p. | 1H NMR (δ) ppm | MS |
|---|---|---|---|---|
| 82 | Colorless crystals ·HCl | 213° C. | | |
| 83 | ·HCl | | DMSO-d6, 300 MHz<br>1.30–1.62(6H, m)<br>2.48(2H, t, J=7.8Hz)<br>2.60(3H, s)<br>2.77(2H, t, J=7.8Hz)<br>6.61(1H, s)<br>7.05–7.51(9H, m)<br>7.92(2H, s)<br>8.65(2H, br.s)<br>8.77(1H, s)<br>10.77(1H, s) | FAB–<br>459 [M–H]–<br>(5)<br>149 (100) |
| 84 | Pale-yellow crystals ·HCl | 285° C. | | |

TABLE 29

| Exp. No. | Structural formula/character (solvent) | m.p. | 1H NMR (δ) ppm | MS |
|---|---|---|---|---|
| 85 |  | | DMSO-d6, 300MHz<br>2.41(3H, s)<br>6.45(2H, s)<br>6.73(2H, br.s)<br>6.85(1H, d, J=7.8Hz)<br>7.13–7.36(13H, m)<br>7.58–7.72(3H, m)<br>8.51(1H, s)<br>10.55(1H, s) | FAB+<br>456 [M+H+]<br>(100) |

TABLE 29-continued
| Exp. No. | Structural formula/character (solvent) | m.p. | 1H NMR (δ) ppm | MS |
|---|---|---|---|---|
| 86 | 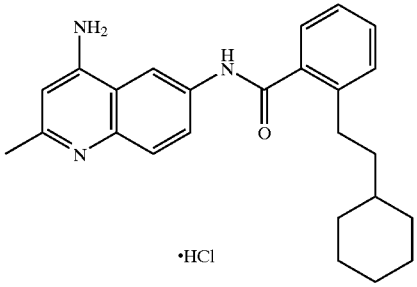 Colorless crystals | 270.0~ 273.0° C. | DMSO-d6, 300MHz 0.81–0.85(2H, m) 1.10–1.18(5H, m) 1.43–1.68(6H, m) 2.60(3H, s) 2.79(2H, t, J=7.7Hz) 6.62(1H, s) 7.31–7.50(4H, m) 7.95(2H, s) 8.60(2H, br.s) 8.77(1H, s) 10.77(1H, s) 13.96(1H, br.s) | FAB– 423 [M–H+] (13) |
| 87 | 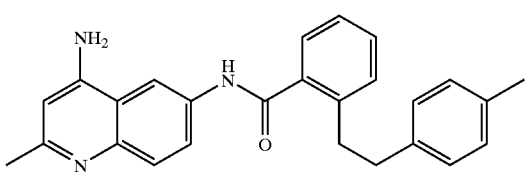 | >300 ° C. | DMSO-d6, 300 MHz | |
TABLE 30
| Exp. No. | Structural formula/character (solvent) | m.p. | 1H NMR (δ) ppm | MS |
|---|---|---|---|---|
| 88 | 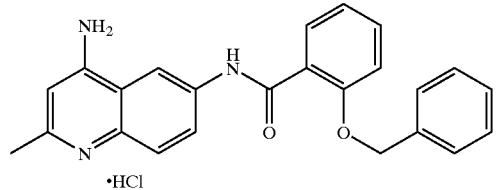 Colorless crystals | 240° C. | | |
| 89 | 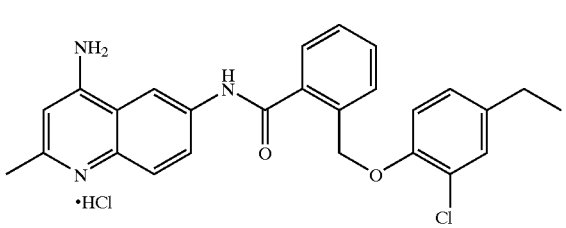 Pale-brown crystals | 245.9° C. | DMSO-d6, 300MHz 1.10(3H, t, J=7.6Hz) 2.50(2H, q, J=7.6Hz) 2.60(3H, s) 5.41(2H, s) 6.62(1H, s) 7.08(2H, s) 7.22(1H, s) 7.50–7.74(4H, m) 7.94–8.02(2H, m) 8.68(2H, br.s) 8.76(1H, s) | FAB– 481 [M–H]- (3) 480 (4) 155 (100) |

TABLE 30-continued

| Exp. No. | Structural formula/character (solvent) | m.p. | 1H NMR (δ) ppm | MS |
|---|---|---|---|---|
| 90 | 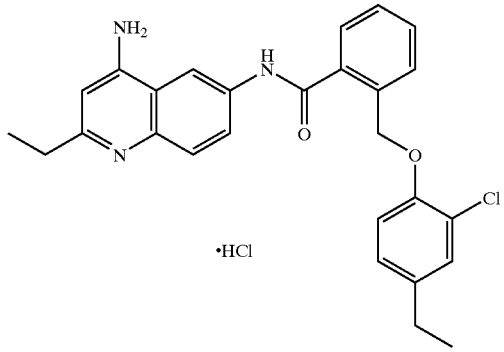<br>Colorless crystals (AcOEt—Et2O) | 137.0~138.0° C. | DMSO-d6<br>1.10(3H, t, J=7.6Hz)<br>1.30(3H, t, J=7.6Hz)<br>2.49(2H, q, J=7.6Hz)<br>2.84(2H, q, J=7.6Hz)<br>5.40(2H, s)<br>6.62(1H, s)<br>7.08(2H, s)<br>7.22(2H, s)<br>7.53–7.62(2H, m)<br>7.69–7.72(2H, m)<br>7.91(2H, s)<br>8.18(2H, br.s)<br>8.68(1H, 5)<br>10.82(1H, s) | |

TABLE 31

| Exp. No. | Structural formula/character (solvent) | m.p. | 1H NMR (δ) ppm | MS |
|---|---|---|---|---|
| 91 | 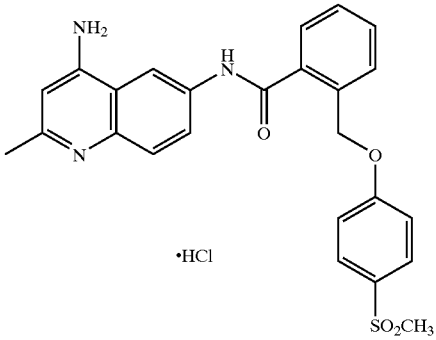<br>Colorless crystals | 185.0~186.0° C. | DMSO-d6,<br>2.59(3H, s)<br>3.11(3H, s)<br>5.45(2H, s)<br>6.60(1H, s)<br>7.16(2H, d, J=8.9Hz)<br>7.55–7.72(4H, m)<br>7.78(2H, d, J=8.9Hz)<br>7.88(2H, d, J=9.0Hz)<br>7.93(2H, d, J=9.0Hz)<br>8.70(1H, br.s)<br>8.72(1H, s)<br>10.89(1H, s)<br>13.77(1H, br.s) | |
| 92 | 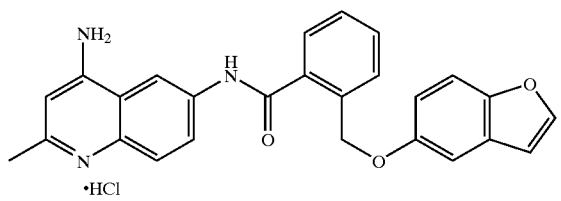 | 269° C. | DMSO-d6, 300MHz | |
| 93 | 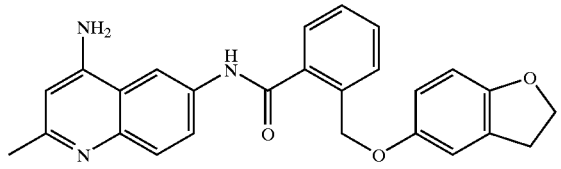 | 233° C. | DMSO-d6, 300MHz | |

TABLE 32

| Exp. No. | Structural formula/character (solvent) | m.p. | 1H NMR (δ) ppm | MS |
|---|---|---|---|---|
| 94 | 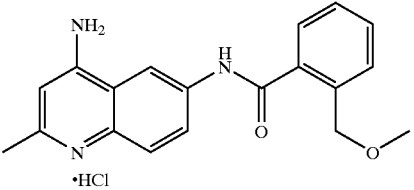<br>·HCl<br>Pale-red crystals | 244° C. | | |
| 95 | 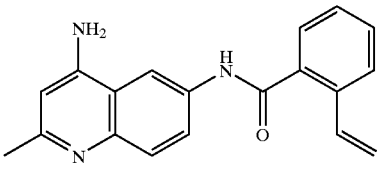 | | DMSO-d6, 300 MHz<br>2.40(3H, s)<br>5.35(1H, d, J=11.6Hz)<br>5.87(1H, d, J=17.8Hz)<br>6.41(2H, br.s)<br>6.45(1H, s)<br>7.04(1H, dd, J=11.6, 17.8Hz)<br>7.42–7.78(6H, m)<br>8.42(1H, s)<br>10.46(1H, s) | FAB+<br>304<br>[M + H+]<br>(100) |
| 96 | 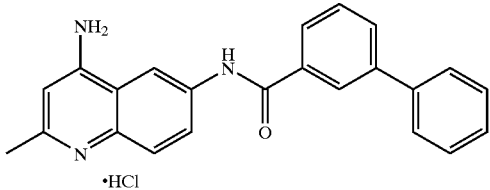<br>·HCl<br>Colorless crystals | 325.0~330.0° C. | | |

TABLE 33

| Exp. No. | Structural formula/character (solvent) | m.p. | 1H NMR (δ) ppm | MS |
|---|---|---|---|---|
| 97 | 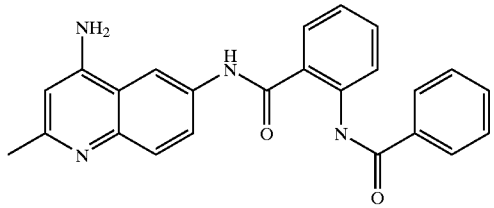 | | DMSO-d6, 300 MHz<br>2.55(3H, s)<br>5.51(2H, s)<br>6.92(1H, s)<br>7.11–7.15(1H, m)<br>7.31–7.36(2H, m)<br>7.51–7.71(1H, m)<br>7.88–7.90(2H, m)<br>8.18(1H, d, J=7.2Hz)<br>8.63(1H, d, J=7.5Hz)<br>10.64(1H, s)<br>12.05(1H, s) | FAB+<br>397<br>[M + H]+<br>(42)<br>174<br>(100) |
| 98 | 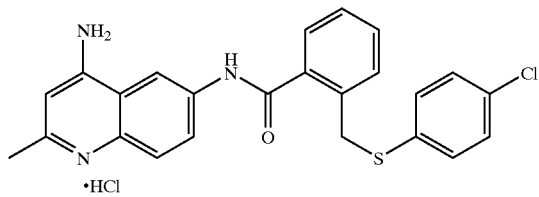<br>·HCl | 216° C. | | |

TABLE 33-continued

| Exp. No. | Structural formula/character (solvent) | m.p. | 1H NMR (δ) ppm | MS |
|---|---|---|---|---|
| 99 | 4-amino-2-methylquinoline-6-yl linked via NH-C(=O) to benzene bearing ortho-CH$_2$-S(=O)-(4-chlorophenyl); ·HCl | 221° C. | | |

TABLE 34

| Exp. No. | Structural formula/character (solvent) | m.p. | 1H NMR (δ) ppm | MS |
|---|---|---|---|---|
| 100 | 4-amino-2-methylquinoline-6-yl linked via NH-C(=O) to benzene bearing ortho-CH$_2$-N(4-chlorophenyl)-C(=O)O-C(CH$_3$)$_3$; ·HCl; Pale-yellow crystals | 208° C. | | |
| 101 | 4-amino-2-methylquinoline-6-yl linked via NH-C(=O) to benzene bearing ortho-CH$_2$-N(CH$_3$)(4-chlorophenyl); ·2HCl | 214° C. | | |
| 102 | 4-amino-2-methylquinoline-6-yl linked via NH-C(=O) to benzene bearing ortho-CH$_2$-NH-(4-chlorophenyl); ·2HCl; Pale-yellow crystals | 274° C. | | |

TABLE 35

| Exp. No. | Structural formula/character (solvent) | m.p. | 1H NMR (δ) ppm | MS |
|---|---|---|---|---|
| 103 | ·HCl | | DMSO-d6, 300 MHz<br>1.83–2.08(3H, m)<br>2.30–2.42(1H, m)<br>2.57(3H, s)<br>3.50–3.75(2H, m)<br>4.68(1H, m)<br>6.57(1H, s)<br>7.47–7.58(5H, m)<br>7.84–7.93(2H, m)<br>8.64(2H, br.s)<br>8.68(1H, s)<br>10.60(1H, s)<br>13.59(1H, s) | |
| 104 | ·HCl | | DMSO-d6, 300 MHz<br>1.83–2.29(4H, m)<br>3.57–3.79(2H, m)<br>3.72(2H, s)<br>4.55(1H, m)<br>6.57(1H, s)<br>7.22–7.38(5H, m)<br>7.88–7.93(2H, m)<br>8.62(1H, s)<br>8.66(1H, br.s)<br>10.57(1H, s)<br>13.88(1H, s) | FAB−<br>423<br>[M − H]−<br>(6)<br>127<br>(100) |
| 105 | ·HCl | | DMSO-d6, 300 MHz<br>1.80–2.39(4H, m)<br>2.58(3H, s)<br>2.79–2.85(2H, m)<br>3.48–3.60(2H, m)<br>4.52–4.54(1H, m)<br>6.58(1H, s)<br>7.11–7.30(5H, m)<br>7.89(2H, s)<br>8.64(3H, br.s)<br>10.52(1H, s)<br>13.79(1H, s) | FAB−<br>437<br>[M − H]−<br>(13)<br>127<br>(100) |

TABLE 36

| Exp. No. | Structural formula/character (solvent) | m.p. | 1H NMR (δ) ppm | MS |
|---|---|---|---|---|
| 106 | ·HCl | | DMSO-d6, 300 MHz<br>1.75–2.03(6H, m)<br>2.33(2H, t, J=6.9Hz)<br>2.51–2.63(5H, m)<br>3.49(2H, m)<br>4.51–4.54(1H, m)<br>6.57(1H, s)<br>7.09–7.31(5H, m)<br>7.89(1H, s)<br>8.61(1H, s)<br>8.64(2H, br.s) | FAB−<br>451<br>[M − H]−<br>(19)<br>127<br>(100) |
| 107 | Amorphous | | CDCl3, 300 MHz<br>1.72–2.07(4H, m)<br>2.18–2.49(2H, m)<br>2.56–2.82(3H, m)<br>2.60(3H, s)<br>3.20–3.24(1H, m)<br>3.32(1H, m)<br>4.86(2H, br.s)<br>6.49(1H, s)<br>7.16–7.29(5H, m)<br>7.32(1H, dd, J=8.9, 2.3Hz)<br>7.94(1H, d, J=8.9Hz)<br>8.55(1H, d, J=2.3Hz)<br>9.70(1H, s) | FAB+<br>389<br>[M + H]+<br>(100) |

TABLE 36-continued

| Exp. No. | Structural formula/character (solvent) | m.p. | 1H NMR (δ) ppm | MS |
|---|---|---|---|---|
| 108 | 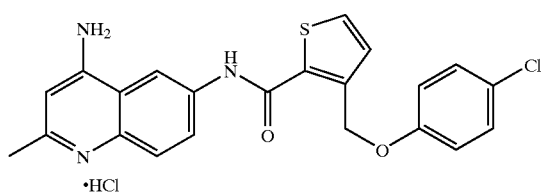 •HCl | 219° C. | DMSO-d6, 300 MHz | |

15

TABLE 37

| Exp. No. | Structural formula/character (solvent) | m.p. | 1H NMR (δ) ppm | MS |
|---|---|---|---|---|
| 109 | 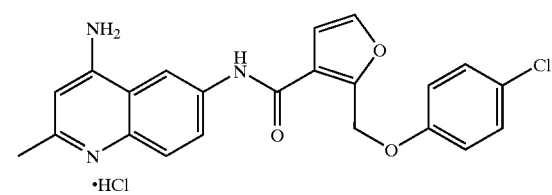 •HCl | | DMSO-d6, 300 MHz<br>2.60(3H, s)<br>5.46(2H, s)<br>6.61(1H, s)<br>7.07(2H, dd, J=7.2, 2.4Hz)<br>7.35(2H, dd, J=7.2, 2.4Hz)<br>7.40(1H, d, J=2.4Hz)<br>7.87(1H, d, J=2.4Hz)<br>8.60–8.80(2H, brs)<br>8.71(1H, s)<br>10.57(1H, s)<br>14.04(1H, s) | |
| 110 | 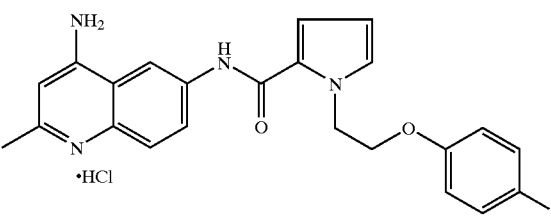 •HCl | | DMSO-d6, 300 MHz<br>2.60(3H, s)<br>4.28(2H, t-like)<br>4.75(2H, t-like)<br>6.17(1H, m)<br>6.62(1H, s)<br>6.92(2H, d, J=9.0Hz)<br>7.18–7.30(4H, m)<br>7.98(1H, d, J=9.1Hz)<br>8.05(1H, d, J=9.1Hz)<br>8.40–8.90(2H, brs)<br>8.64(1H, s)<br>10.32(1H, s)<br>14.18(1H, s) | |
| 111 | 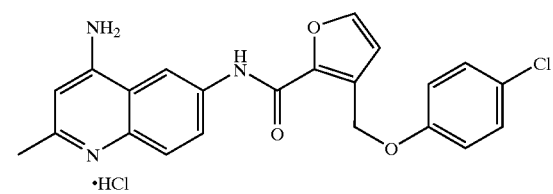 •HCl | | DMSO-d6, 300 MHz<br>2.61(3H, s)<br>5.42(2H, s)<br>6.65(1H, s)<br>6.83(1H, d, J=1.7Hz)<br>7.04(2H, d, J=8.9Hz)<br>7.35(2H, d, J=8.9Hz)<br>7.99(1H, d, J=1.7Hz)<br>8.50–9.00(2H, brs)<br>8.73(1H, s)<br>10.73(1H, s)<br>14.4(1H, s) | |

TABLE 38

| Exp. No. | Structural formula/character (solvent) | m.p. | 1H NMR (δ) ppm | MS |
|---|---|---|---|---|
| 112 | (structure: 4-amino-2-methylquinoline-6-yl amide linked to oxazole-CH2-O-(4-chlorophenyl)) | | DMSO-d6, 300 MHz 2.40(3H, s) 5.57(2H, s) 6.44(1H, s) 6.48(2H, s) 7.12(2H, d, J=7.2Hz) 7.37(2H, d, J=7.2Hz) 7.65(1H, d, J=8.8Hz) 7.85(1H, d, J=8.8Hz) 8.39(1H, s) 8.69(1H, s) 10.30(1H, s) | |
| 113 | (structure: 4-amino-2-methylquinoline-6-yl amide of prolinyl with N-CH2CH2-O-(4-chlorophenyl)) ·2HCl Pale-brown crystals | 216° C. | | |
| 114 | (structure: 4-amino-2-methylquinoline-6-yl amide of prolinyl with N-CH2CH2CH2-O-(4-chlorophenyl)) ·2HCl Pale-yellow crystals | 211° C. | | |

TABLE 39

| Exp. No. | Structural formula/character (solvent) | m.p. | 1H NMR (δ) ppm | MS |
|---|---|---|---|---|
| 115 | (structure: 4-amino-2-methylquinoline-6-yl amide of prolinyl with N-CH2CH2-O-(4-chlorophenyl)) ·2HCl Pale-brown crystals | 253° C. | | |
| 116 | (structure: 4-amino-2-methylquinoline-6-yl amide of cyclohexenyl bearing CH2-O-phenyl substituent) ·HCl | | DMSO-d6, 300 MHz 1.67(4H, brs) 2.22(2H, brs) 2.37(2H, brs) 2.58(3H, s) 4.61(2H, s) 6.59(1H, s) 6.88–6.92(3H, m) 7.21–7.28(2H, m) 7.88(2H, s) 8.62(2H, brs) 8.68(1H, s) 10.45(1H, s) 13.85(1H, s) | |

TABLE 39-continued

| Exp. No. | Structural formula/character (solvent) | m.p. | 1H NMR (δ) ppm | MS |
|---|---|---|---|---|
| 117 | 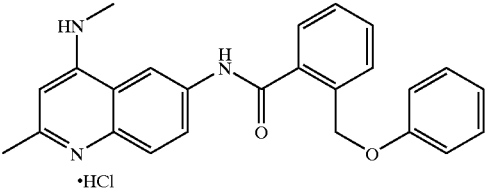 | 284° C. | DMSO-d6, 300 MHz | |

TABLE 40

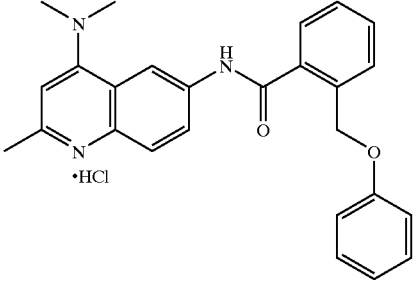

| Exp. No. | Structural formula/character (solvent) | m.p. | 1H NMR (δ) ppm | MS |
|---|---|---|---|---|
| 118 | Colorless crystals (AcOEt—Et2O) | | CD3OD, 300 MHz 2.67(3H, s) 3.39(6H, s) 5.32(2H, s) 6.79(1H, s) 6.84–6.90(3H, m) 7.13–7.19(2H, m) 7.48–7.67(4H, m) 7.75(1H, d, J = 9.0 Hz) 7.91(1H, dd, J = 2.0, 9.0 Hz) 8.95(1H, s) | FAB– 447 [M–H+] (28) |
| 119 | Pale-gray crystals | 219° C. | DMSO-d6, 300 MHz 1.09(3H, t, J = 7.5 Hz) 2.47(2H, q, J = 7.5 Hz) 5.30(2H, s) 6.78(1H, d, J = 6.9 Hz) 6.84(2H, d, J = 8.7 Hz) 7.03(2H, d, J = 8.7 Hz) 7.51–7.69(4H, m) 7.90–7.99(2H, m) 8.36(1H, br.t) 8.79(1H, s) 8.90(2H, br.s) 10.89(1H, s) 13.89(1H, s) | |
| 120 | Pale-gray crystals | 231° C. | DMSO-d6, 300 MHz 5.34(2H, s) 6.79(1H, d, J = 6.8 Hz) 6.96(2H, d, J = 6.9 Hz) 7.26(2H, d, J = 6.9 Hz) 7.50–7.71(4H, m) 7.93–8.00(2H, m) 8.35(1H, d, J = 6.8 Hz) 8.78(1H, s) 8.88(2H, br.s) 10.90(1H, s) 14.03(1H, s) | |

TABLE 41

| Exp. No. | Structural formula/character (solvent) | m.p. | 1H NMR (δ) ppm | MS |
|---|---|---|---|---|
| 121 | 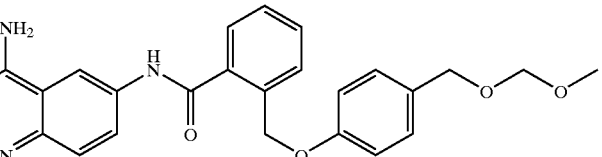<br>•HCl<br>Pale-yellow crystals | 276° C. | DMSO-d6, 300 MHz<br>2.60(3H, s)<br>3.26(3H, s)<br>4.39(2H, s)<br>6.57(2H, s)<br>5.34(2H, s)<br>6.61(1H, s)<br>6.92(2H, d, J=8.5Hz)<br>7.20(2H, d, J=8.5Hz)<br>7.47–7.70(4H, m)<br>7.95(2H, s)<br>8.61(2H, br.s)<br>8.75(1H, s) | FAB–<br>492<br>[M − H]–<br>(100) |
| 122 | <br>•HCl<br>Colorless crystals | 116.0~117.0° C. | DMSO-d6, 300 MHz<br>5.34(2H, s)<br>6.90–6.95(3H, m)<br>7.19–7.26(3H, m)<br>7.52–7.71(5H, m)<br>7.93–7.97(2H, m)<br>8.94(1H, s)<br>9.05(1H, br.s)<br>11.0(1H, s)<br>13.4(1H, br.s) | FAB–<br>405<br>[M − H+]<br>(6) |
| 123 | 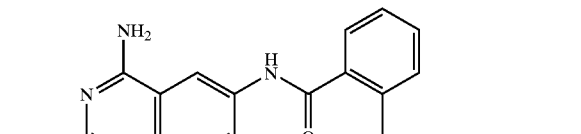<br>•HCl | 283° C. | DMSO-d6, 300 MHz | |

TABLE 42

| Exp. No. | Structural formula/character (solvent) | m.p. | 1H NMR (δ) ppm | MS |
|---|---|---|---|---|
| 124 | 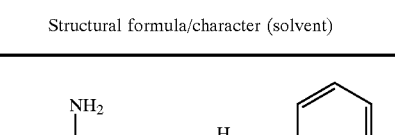<br>•HCl<br>Colorless crystals | 164.0~165.0° C. | DMSO-d6<br>2.21(2H, t, J=7.3Hz)<br>2.89(2H, t, J=7.3Hz)<br>3.18(2H, t, J=7.3Hz)<br>5.35(2H, s)<br>6.97(2H, d, J=9.0Hz)<br>7.27(2H, d, J=9.0Hz)<br>7.50–7.71(4H, m)<br>7.86–7.89(2H, m)<br>8.45(2H, br.s)<br>8.76(1H, s)<br>10.83(1H, s)<br>14.24(1H, br.s) | FAB–<br>479<br>[M − H+]<br>(3) |

TABLE 42-continued

| Exp. No. | Structural formula/character (solvent) | m.p. | 1H NMR (δ) ppm | MS |
|---|---|---|---|---|
| 125 | 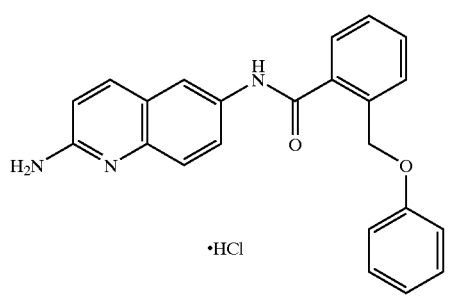<br>Colorless crystals | 190.0~191.0° C. | DMSO-d6<br>5.31(2H, s)<br>6.87–6.93(3H, m)<br>7.09(1H, d, J=9.2Hz)<br>7.20–7.25(2H, m)<br>7.48–7.64(4H, m)<br>7.69(1H, d, J=9.2Hz)<br>7.94(1H, d, J=9.2Hz)<br>8.38(1H, d, J=9.2Hz)<br>8.41(1H, s)<br>10.78(1H, s)<br>14.11(1H, br.s) | |
| 126 | 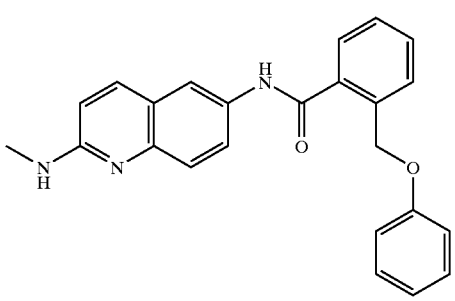<br>Colorless crystals | 172.0~173.0° C. | DMSO-d6, 300 MHz<br>2.88(3H, d, J=4.8Hz)<br>5.31(2H, s)<br>6.73(1H, d, J=8.8Hz)<br>6.88–6.96(4H, m)<br>7.21–7.27(2H, m)<br>7.46–7.56(3H, m)<br>7.62–7.68(3H, m)<br>7.78(3H, d, J=8.8Hz)<br>8.11(1H, d, J=2.2Hz)<br>10.42(1H, s) | FAB+<br>384<br>[M + H+]<br>(100) |

TABLE 43

| Exp. No. | Structural formula/character (solvent) | m.p. | 1H NMR (δ) ppm | MS |
|---|---|---|---|---|
| 127 | 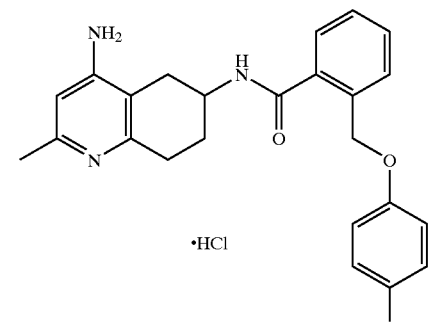<br>Colorless crystals (AcOEt—Et2O) | 153.0~155.0° C. | DMSO-d6, 300 MHz<br>1.68–2.09(2H, m)<br>2.39(3H, s)<br>2.31–2.56(2H, m)<br>2.73–2.98(3H, m)<br>4.21–4.34(1H, m)<br>5.25(2H, dd, J=8.9Hz, J=12.5Hz)<br>6.50(1H, s)<br>6.99(2H, d, J=8.9Hz),<br>7.33(2H, d, J=8.9Hz)<br>7.42–7.57(4H, m)<br>7.90–8.14(2H, m)<br>8.60(1H, d, J=7.6Hz)<br>13.10(1H, s) | FAB−<br>457<br>[M − H+]<br>(58) |
| 128 | 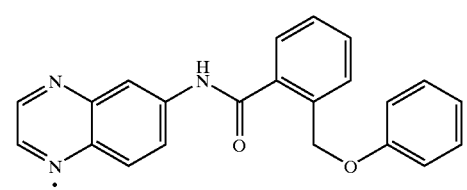 | | DMSO-d6, 300 MHz<br>5.34(2H, s)<br>6.85–6.94(3H, m)<br>7.18–7.25(2H, m)<br>7.50–7.61(4H, m)<br>8.06(1H, d, J=8.7Hz)<br>8.11<br>8.63(1H, J=1.8Hz)<br>8.84(1H, d, J=1.8Hz)<br>8.91(1H, d, J=1.8Hz)<br>10.97(1H, s) | |

TABLE 43-continued

| Exp. No. | Structural formula/character (solvent) | m.p. | 1H NMR (δ) ppm | MS |
|---|---|---|---|---|
| 129 | 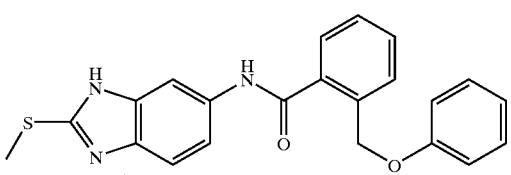 ·HCl Colorless crystals | 191° C. | | |

TABLE 44

| Exp. No. | Structural formula/character (solvent) | m.p. | 1H NMR (δ) ppm | MS |
|---|---|---|---|---|
| 130 | ·HCl Colorless crystals | 237° C. | | |
| 131 | ·HCl | 201° C. | | |
| 132 | ·HCl Colorless crystals | 241° C. | | |

The method for evaluating the analgesic effect of the compound of the present invention is explained in the following.

For in vitro evaluation, ORL-1 receptor binding assay was performed, and μ receptor binding assay was performed for the evaluation of selectivity. For in vivo evaluation, hot plate test and tail flick test known for long as a test method for analgesic effect were performed, and tactile sensation stimulating test was performed using allodynia model for evaluation of allodynia.

Experimental Example [1]
ORL1 Receptor Binding Assay

A cell membrane suspension obtained from human ORL-1 expression cells was adjusted with Tris buffer [50 mM Tris, 2 mM EDTA, 0.1 mM (p-Amidinophenyl) methanesulfonyl Fluoride Hydrochloride (p-APMSF), 2 mg/ml BSA] to membrane protein amount of about 25 μg/ml (2.5 μg/well). This was mixed with [$^3$H]nociceptin (diluted with Tris buffer to a final concentration of 0.5 nM) and test compound (diluted with Tris buffer to a final concentration of 10 nM–10 μM), and the mixture was incubated at room temperature for 60 min. The membrane was recovered on a G/F-B filter (Packard, Unifilter 96GF/B) using a cell harvester and the reaction was stopped. After washing 3 times, the filter was dried at 42° C. for 1 hr. A scintillation solution (Packard, microscint-20) was added and the radioactivity (Packard, Top count A9912V) was assayed.

The nonspecific binding was the binding in the presence of 1 μM nociceptin and the difference between the total binding and nonspecific binding was taken as the specific binding. $IC_{50}$ was calculated from inhibition of specific binding at each concentration of the compound, and Ki value of the test compound was calculated from this value and Kd value of [$^3$H]nociceptin.

Experimental Example [2]

μ Receptor Binding Assay

Rat cerebrum membrane standard sample (final concentration 0.755 mg·protein/ml), [$^3$H]DAMGO (Try-D-Ala-Gly-NMe-Phe-Gly-ol) [diluted with Tris buffer (50 mM Tris-HCl, 0.1 mM p-APMSF, 2 mg/ml BSA (pH=7.4)) to a final concentration of 1 nM] and test compound (diluted with Tris buffer to a final concentration of 10 nM–10 μM) were mixed, and the mixture was incubated at room temperature for 90 min. The membrane was recovered on a G/F-B filter (same as above) using a cell harvester and the reaction was stopped. After washing 3 times, the filter was dried at 42° C. for 1 hr. A scintillation solution (same as above) was added and the radioactivity (same as above) was assayed.

The nonspecific binding was the binding in the presence of 10 μM naloxone and the difference between the total binding and nonspecific binding was taken as the specific binding. $IC_{50}$ was calculated from inhibition of specific binding at each concentration of the compound, and Ki value of the test compound was calculated from this value and Kd value of [$^3$H]DAMGO.

Experimental Example [3]

Hot-plate Test

Mice (Crj, ICR, 4-week-old, male) were placed on a hot-plate (temperature 55.5±0.5° C.) and the time until the mice jumped and tried to run away was recorded. The mice were grouped according to the time and body weight so that the groups were evenly membered. The test compound was suspended in a 0.5% methylcellulose (MC) solution and orally administered to mice. After 60 min, the mice were again placed on a hot-plate and the time until they licked the hindlimb or jumped and tried to run away was recorded. The significant difference from the group administered with solvent was analyzed with ANOVA followed by Dunnett two-tailed test.

Experimental Example [4]

Tail-flick Test

Rats (Crj, SD, 7 or 8-week-old, male) were irradiated with thermal beam at around the base of the tail from below and the time until the rats moved the tail and ran away was measured using a tail-flick analgesic effect measurement device (manufactured by UGO BASILE). Before the administration of the test compound, the measurement was repeated 3 times and the rats were grouped according to the time and body weight so that the groups were evenly membered. The test compound was suspended in a 0.5% MC solution and orally administered to rats. After 30, 60, 90, 120 and 180 minutes from administration, the same measurement was repeated. The significant difference from the group administered with solvent was analyzed with ANOVA followed by Dunnett two-tailed test.

Experimental Example [5]

Allodynia Test

Mice (Crj, ICR, 4-week-old, male) were intrathecally administered with nociceptin (50 pg/5 μl) without anesthesia. For 20 min after administration and at 5 min intervals, an area from lateral region to tail of the mice was rubbed with a brush and the response of the mice was observed. The evaluation followed the criteria of 0; no change, 1; run or cry upon tactile stimulation, and 2; cry loud or dash away upon tactile stimulation. The test compound was suspended in a 0.5% MC solution and orally administered 60 min before nociceptin administration. The significant difference of the score of each administration group at 20 min after nociceptin administration from the group administered with solvent was analyzed with Mann-Whitny U-test.

The results of Experimental Examples [1] to [5] are shown in Tables 45–47.

TABLE 45

| Example No. | ORL-1 binding | | μ binding | | Allodynia | Hot-plate |
|---|---|---|---|---|---|---|
| | $IC_{50}$ (μM) | Ki (μM) | $IC_{50}$ (μM) | Ki (μM) | M.E.D. (mg/kg) | M.E.D. (mg/kg) |
| 1 | 0.12 | 0.007 | 1.52 | 0.570 | 0.3 | 1 |
| 2 | 0.07 | 0.004 | 1.33 | 0.497 | 0.3 | 1 |
| 3 | 1.47 | 0.079 | 1.11 | 0.417 | 3 | 30 |
| 4 | 0.23 | 0.013 | 1.26 | 0.453 | <1 | <3 |
| 5 | 0.52 | 0.028 | 1.34 | 0.505 | 3 | |
| 7 | 0.06 | 0.003 | 0.96 | 0.346 | 0.3 | 3 |
| 8 | 0.94 | 0.050 | 0.49 | 0.183 | 3 | |
| 9 | 0.32 | 0.016 | 2.03 | 0.764 | 1 | <3 |
| 10 | 1.02 | 0.053 | 0.86 | 0.324 | 3 | |
| 11 | 0.06 | 0.003 | 1.12 | 0.424 | 0.3 | 3 |
| 12 | 0.16 | 0.008 | 0.67 | 0.254 | 0.3 | 3 |
| 16 | 0.11 | 0.006 | 0.69 | 0.259 | 0.1 | 3 |
| 17 | 0.13 | 0.007 | 1.02 | 0.385 | 0.3 | 1 |

M.E.D.: minimum effective dose

TABLE 46

| Example No. | ORL-1 binding | | μ binding | | Allodynia | Hot-plate |
|---|---|---|---|---|---|---|
| | $IC_{50}$ (μM) | Ki (μM) | $IC_{50}$ (μM) | Ki (μM) | M.E.D. (mg/kg) | M.E.D. (mg/kg) |
| 18 | 0.09 | 0.004 | 1.04 | 0.393 | 0.3 | |
| 19 | 0.16 | 0.009 | 1.03 | 0.388 | 0.1 | 3 |
| 25 | 0.15 | 0.008 | 1.18 | 0.464 | 0.3< | |
| 26 | 0.08 | 0.004 | 1.22 | 0.479 | 0.3 | 1 |
| 27 | 0.29 | 0.015 | 1.06 | 0.414 | 0.3 | |
| 29 | 0.16 | 0.009 | 1.05 | 0.414 | 0.3< | 3 |
| 32 | 0.09 | 0.005 | 0.58 | 0.227 | 0.3< | — |
| 33 | 0.09 | 0.005 | 1.44 | 0.565 | 0.3 | |
| 34 | 0.14 | 0.008 | 2.37 | 0.888 | 0.3 | 3 |
| 38 | 0.09 | 0.005 | 2.67 | 1.021 | 0.3< | |
| 42 | 0.08 | 0.004 | 1.99 | 0.745 | 0.3 | 1 |
| 43 | 0.11 | 0.005 | 2.10 | 0.785 | 0.3 | 1 |
| 49 | 0.04 | 0.002 | 1.26 | 0.464 | 0.3 | 1 |

M.E.D.: minimum effective dose

TABLE 47

| Example No. | ORL-1 binding | | μ binding | | Allodynia | Hot-plate |
|---|---|---|---|---|---|---|
| | $IC_{50}$ (μM) | Ki (μM) | $IC_{50}$ (μM) | Ki (μM) | M.E.D. (mg/kg) | M.E.D. (mg/kg) |
| 51 | 0.17 | 0.008 | 1.40 | 0.525 | | |
| 61 | 1.22 | 0.063 | 5.35 | 2.012 | 3 | |
| 62 | 2.36 | 0.125 | 2.00 | 0.783 | 3< | |
| 63 | 1.03 | 0.054 | 1.42 | 0.545 | 3< | |
| 64 | 1.39 | 0.073 | 3.61 | 1.382 | 3< | |
| 65 | 1.16 | 0.064 | | | 3< | |
| 66 | 2.00 | 0.108 | | | 3< | |
| 71 | 1.77 | 0.089 | | | 30 | |
| 84 | 2.52 | 0.129 | 1.11 | 0.419 | <3 | 10< |
| 89 | 0.13 | 0.006 | 1.46 | 0.548 | 0.3 | 1 |
| 90 | 0.11 | 0.005 | 1.18 | 0.442 | — | 3 |
| 93 | 0.12 | 0.007 | | | 0.3< | — |

M.E.D.: minimum effective dose

EFFECTS OF THE INVENTION

As is evident from the above test results, the compound of the present invention shows strong analgesic effect due to nociceptin antagonistic action, and a part thereof shows selective action on ORL-1 receptors as compared to opioid receptors (μ, κ, δ receptors) including μ receptor.

Hence, the inventive compound can make a pharmaceutical agent effective against pain, particularly strong pain such as postoperative pain and the like or pain caused by sensory nerve abnormality such as hyperalgesia, allodynia and the like. In addition, since the compound shows selective action on ORL-1 receptor, it can be a safe pharmaceutical agent without marked side effects.

This application is based on application No. 100029/1998 filed in Japan, the content of which is incorporated hereinto by reference.

What is claimed is:

1. A method for treating pain, comprising administering to a host an effective amount of an amide derivative of the formula [1]

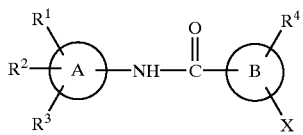

wherein $R^1$ and $R^2$ are the same or different and each is hydrogen atom, lower alkyl optionally substituted by hydroxy, amino, lower alkylamino or di(lower)alkylamino;

$R^3$ and $R^4$ are the same or different and each is hydrogen atom, halogen atom or lower alkyl:

ring A is quinolyl;

ring B is phenyl, thienyl, furyl, pyrrolyl, pyrrolidinyl, oxazolyl or cyclohexenyl; and X is a group of the formula

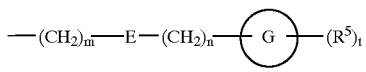

wherein

E is a single bond, carbonyl, sulfinyl, —O—, —S—, —NHCO—, —CH=CR$^6$— wherein R$^6$ is hydrogen atom or aryl or —NR$^7$— wherein R$^7$ is hydrogen atom, lower alkyl or lower alkoxycarbonyl;

ring G is aryl, a heterocyclic group selected from the group consisting of pyrrolyl, thienyl, furyl, imidazolyl, pyrazolyl, oxazolyl, thiazolyl, indolyl, benzofuranyl, benzimidazolyl, imidazolidinyl, indolinyl, pyrrolidinyl, carbazolyl and 2,3-dihydrobenzofuranyl, cycloalkyl or condensed aryl;

$R^5$ is halogen atom, hydroxy, lower alkyl optionally substituted by any of halogen atom, hydroxy, lower alkanoyloxy and lower alkoxy optionally substituted by lower alkoxy, lower alkoxy optionally substituted by lower alkoxy, amino, lower alkylamino, di(lower) alkylamino, nitro, cyano, lower alkanoyl, lower alkanoyloxy, carboxy, lower alkoxycarbonyl, lower alkylsulfonyl or phenyl;

t is 0 or an integer of 1 to 5, which indicates the number of substituents on the ring G, wherein when t is an integer of 2 to 5, each $R^5$ is the same or different;

m is 0 or an integer of 1 to 8; and n is 0 or an integer of 1 to 4, or a pharmaceutically acceptable salt thereof.

2. An amide derivative of the formula [1']

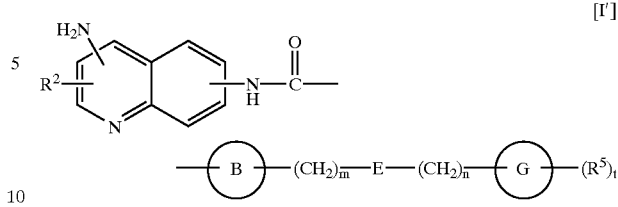

wherein $R^2$, ring B, E, ring G, $R^5$, t, m and n as defined in claim 1, or a pharmaceutically acceptable salt thereof.

3. The amide derivative of claim 2, wherein the ring B is phenyl and $R^2$ is lower alkyl, or a pharmaceutically acceptable salt thereof.

4. The amide derivative of claim 3, wherein the amino substitutes at the 4-position on a quinoline skeleton, $R^2$ is methyl substituting at the 2-position on the quinoline skeleton, E is —O— and the ring B of phenyl has a substituent of the formula

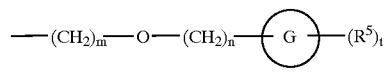

wherein ring G, $R^5$, t, m and n as defined in claim 1, at the 2-position, or a pharmaceutically acceptable salt thereof.

5. The amide derivative of claim 4 or a pharmaceutically acceptable salt thereof, which is selected from the group consisting of N-(4-amino-2-methyl-6-quinolyl)-2-[(4-ethylphenoxy) methyl]benzamide hydrochloride, N-(4-amino-2-methyl-6-quinolyl)-2-[(2,4-dichlorophenoxy)methyl]benzamide hydrochloride, N-(4-amino-2-methyl-6-quinolyl)-2-(phenoxymethyl) benzamide hydrochloride, N-(4-amino-2-methyl-6-quinolyl)-2-[(4-methoxyphenoxy) methyl]benzamide hydrochloride, N-(4-amino-2-methyl-6-quinolyl)-2-[(3,5-dimethylphenoxy)methyl]benzamide hydrochloride, N-(4-amino-2-methyl-6-quinolyl)-2-[(3,4-dimethoxyphenoxy)methyl]benzamide hydrochloride, N-(4-amino-2-methyl-6-quinolyl)-2-[(4-nitrophenoxy) methyl]benzamide, N-(4-amino-2-methyl-6-quinolyl)-2-[(2,3-dimethoxyphenoxy)methyl]benzamide hydrochloride, N-(4-amino-2-methyl-6-quinolyl)-2-[(3-methylphenoxy) methyl]benzamide, N-(4-amino-2-methyl-6-quinolyl)-2-[(3,5-dimethoxyphenoxy)methyl]benzamide hydrochloride, N-(4-amino-2-methyl-6-quinolyl)-2-[(4-chlorophenoxy) methyl]benzamide hydrochloride, N-(4-amino-2-methyl-6-quinolyl)-2-[(4-acetylphenoxy) methyl]benzamide hydrochloride, N-(4-amino-2-methyl-6-quinolyl)-2-[(4-hydroxyphenoxy) methyl]benzamide hydrochloride, N-(4-amino-2-methyl-6-quinolyl)-2-[(4-methoxymethoxyphenoxy)methyl]benzamide hydrochloride, N-(4-amino-2-methyl-6-quinolyl)-2-[(3-methoxyphenoxy) methyl]benzamide hydrochloride, N-(4-amino-2-methyl-6-quinolyl)-2-[(4-cyanophenoxy) methyl]benzamide hydrochloride, N-(4-amino-2-methyl-6-quinolyl)-2-[(4-methylphenoxy) methyl]benzamide hydrochloride, N-(4-amino-2-methyl-6-quinolyl)-2-[(4-trifluoromethylphenoxy)methyl]benzamide hydrochloride, N-(4-amino-2-methyl-6-quinolyl)-2-[(3-nitrophenoxy)methyl]benzamide hydrochloride,
N-(4-amino-2-methyl-6-quinolyl)-2-[(2-nitrophenoxy)methyl]benzamide hydrochloride,
N-(4-amino-2-methyl-6-quinolyl)-2-[(4-acetoxyphenoxy)methyl]benzamide hydrochloride,
N-(4-amino-2-methyl-6-quinolyl)-2-[(2-methoxyphenoxy)methyl]benzamide hydrochloride,
N-(4-amino-2-methyl-6-quinolyl)-2-[(4-aminophenoxy)methyl]benzamide dihydrochloride,
N-(4-amino-2-methyl-6-quinolyl)-2-[(3-chlorophenoxy)methyl]benzamide hydrochloride,
N-(4-amino-2-methyl-6-quinolyl)-2-[(4-fluorophenoxy)methyl]benzamide hydrochloride,
N-(4-amino-2-methyl-6-quinolyl)-2-[(3,4-dichlorophenoxy)methyl]benzamide hydrochloride,
N-(4-amino-2-methyl-6-quinolyl)-2-[(2-chlorophenoxy)methyl]benzamide hydrochloride,
N-(4-amino-2-methyl-6-quinolyl)-2-[(4-dimethylaminophenoxy)methyl]benzamide dihydrochloride,
N-(4-amino-2-methyl-6-quinolyl)-2-[(4-tert-butylphenoxy)methyl]benzamide hydrochloride,
N-(4-amino-2-methyl-6-quinolyl)-2-(4-biphenylyloxymethyl)benzamide hydrochloride,
N-(4-amino-2-methyl-6-quinolyl)-2-[(4-isopropylphenoxy)methyl]benzamide hydrochloride,
N-(4-amino-2-methyl-6-quinolyl)-2-[(4-nitrophenoxy)methyl]benzamide hydrochloride,
N-(4-amino-2-methyl-6-quinolyl)-2-[(4-bromophenoxy)methyl]benzamide hydrochloride,
N-(4-amino-2-methyl-6-quinolyl)-2-[(4-propylphenoxy)methyl]benzamide hydrochloride,
N-(4-amino-2-methyl-6-quinolyl)-2-[(3-fluorophenoxy)methyl]benzamide hydrochloride,
N-(4-amino-2-methyl-6-quinolyl)-2-[(3-trifluoromethylphenoxy)methyl]benzamide hydrochloride,
methyl 4-[2-{N-(4-amino-2-methyl-6-quinolyl)carbamoyl}benyloxy]benzoate hydrochloride,
N-(4-amino-2-methyl-6-quinolyl)-2-[(4-iodophenoxy)methyl]benzamide,
N-(4-amino-2-methyl-6-quinolyl)-2-(3-pyridyloxymethyl)benzamide hydrochloride,
4-[2-{(4-amino-2-methyl-6-quinolyl)carbamoyl}benzyloxy]benzoate hydrochloride,
N-(4-amino-2-methyl-6-quinolyl)-2-[(3-cyanophenoxy)methyl]benzamide hydrochloride,
N-(4-amino-2-methyl-6-quinolyl)-2-[(4-mesylphenoxy)methyl]benzamide hydrochloride,
N-(4-amino-2-methyl-6-quinolyl)-2-[(2chloro-4-ethylphenoxy)methyl]benzamide hydrochloride,
N-(4-amino-2-methyl-6-quinolyl)-2-[(4-chloro-3-methylphenoxy)methyl]benzamide hydrochloride,
N-(4-amino-2-methyl-6-quinolyl)-2-[(2-chloro-4-methylphenoxy)methyl]benzamide hydrochloride,
N-(4-amino-2-methyl-6-quinolyl)-2-[(4-ethylphenoxy)methyl]benzamide,
N-(4-amino-2-methyl-6-quinolyl)-2-[(4-chloro-3-methylphenoxy)methyl]benzamide,
4-[2-{(4-amino-2-methyl-6-quinolyl)carbamoyl}benzyloxy]benzyl acetate hydrochloride,
N-(4-amino-2-methyl-6-quinolyl)-2-[(4-hydroxymethylphenoxy)methyl]benzamide hydrochloride and
N-(4-amino-2-methyl-6-quinolyl)-2-[(4-ethylphenoxy)methyl]benzamide hydrochloride monohydrate.

6. An amide derivative of the formula [1″]

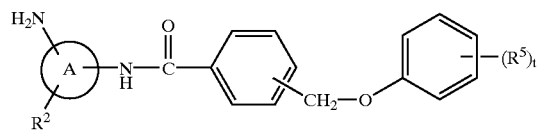

wherein the ring A, $R^2$, $R^5$ and t are as defined in claim 1, or a pharmaceutically acceptable salt thereof.

7. A pharmaceutical composition comprising an effective amount of the amide derivative of claim 2 or a pharmaceutically acceptable salt thereof and a pharmaceutically acceptable carrier.

8. A method for expressing a nociceptin antagonistic action, comprising administering to a host an effective amount of the amide derivative of claim 7 or a pharmaceutically acceptable salt thereof.

9. A method for treating pain, comprising administering to a host an effective amount of the amide derivative of claim 2 or a pharmaceutically acceptable salt thereof.

10. A method for expressing a nociceptin antagonistic action, comprising administering to a host an effective amount of the amide derivative of the formula [1] of claim 1 or a pharmaceutically acceptable salt thereof.

11. The method of claim 1, wherein ring G is aryl, heterocyclic group selected from the group consisting of benzofuranyl and 2,3-dihydrobenzofuranyl, cycloalkyl, or condensed aryl.

12. The amide derivative of claim 2, wherein ring G is aryl, heterocyclic group selected from the group consisting of benzofuranyl and 2,3-dihydrobenzofuranyl, cycloalkyl, or condensed aryl.

* * * * *